US008106035B2

(12) United States Patent     (10) Patent No.: US 8,106,035 B2
Posner et al.     (45) Date of Patent: Jan. 31, 2012

(54) 25-SO$_2$-SUBSTITUTED ANALOGS OF 1μ,25-DIHYDROXYVITAMIN D$_3$

(75) Inventors: Gary H. Posner, Baltimore, MD (US); Jae Kyoo Lee, Andover, MA (US); Qiang Wang, Newark, CA (US); Kenneth R. Crawford, San Mateo, CA (US); Hong Woon Yang, Superior, CO (US); Steven M. Silverman, San Diego, CA (US); Byung-Chul Suh, Cockeysville, MD (US); Jay A. White, Newmarket (CA); Glenville Jones, Kingston (CA); Uttam Saha, Toronto (CA); Heung Bae Jeon, Andover, MA (US)

(73) Assignee: Cytochroma Inc., Markham (CA)

( * ) Notice: Subject to any disclaimer, the term of this patent is extended or adjusted under 35 U.S.C. 154(b) by 169 days.

(21) Appl. No.: 10/738,248

(22) Filed: Dec. 18, 2003

(65) Prior Publication Data

US 2004/0224930 A1    Nov. 11, 2004

Related U.S. Application Data

(60) Provisional application No. 60/433,951, filed on Dec. 18, 2002.

(51) Int. Cl.
*A61K 31/59* (2006.01)
*C07C 401/00* (2006.01)
(52) U.S. Cl. ........................................ 514/167; 552/653
(58) Field of Classification Search .................. 514/167; 552/653
See application file for complete search history.

(56) References Cited

U.S. PATENT DOCUMENTS

| | | | |
|---|---|---|---|
| 4,481,198 A | | 11/1984 | DeLuca et al. |
| 5,411,949 A | * | 5/1995 | Neef et al. ............. 514/167 |
| 5,428,029 A | * | 6/1995 | Doran et al. ............ 514/167 |
| 5,936,105 A | * | 8/1999 | Paaren .................. 552/653 |
| 6,043,386 A | | 3/2000 | Posner et al. |
| 6,380,408 B1 | | 4/2002 | Posner et al. |
| 6,537,980 B1 | * | 3/2003 | Hansen ................. 514/167 |
| 7,166,585 B2 | * | 1/2007 | Posner et al. .......... 514/167 |
| 2003/0004144 A1 | * | 1/2003 | Hansen ................. 514/167 |

FOREIGN PATENT DOCUMENTS

| | | |
|---|---|---|
| EP | 0386793 | 12/1990 |
| WO | WO 9115475 | 10/1991 |
| WO | WO 9410139 | 5/1994 |
| WO | WO 9414766 | 7/1994 |
| WO | WO 00/59513 | * 10/2000 |
| WO | WO 0059513 | 10/2000 |

OTHER PUBLICATIONS

Crawford, Ph.D. Thesis, Johns Hopkins University, 2001.*
Wang, Ph.D Thesis, Johns Hopkins University, 2000.*
Schröder E. et al., "Arznelmitteichemie passage", Arzneimittelchemie Grundlagen Nerven, 1976, pp. 30-33, XP002186820.
Greising, D. M. et al., "A-Ring Analogues of 1,25-(OH)$_2$D$_3$ With Low Affinity for the Vitamin D Receptor Modulate Chondrocytes via Membrane Effects That Are Dependent on Cell Maturation", Journal of Cellular Physiology, 1997, pp. 357-367, vol. 171.
Hartman, R. W. et al., "Synthesis and Evaluation of Novel Steroidal Oxime Inhibitors of P450 17 (17α-Hydroxlase/C17-20-Lyase) and 5α-Reductase Types 1 and 2", Journal of Medical Chemistry, 2000, pp. 4266-4277, vol. 43, No. 22.
Kensler, T. W. et al., "Conceptually new deltanoids (vitamin D analogs) inhibit multistage skin tumorigenesis", Carcinogenesis, 2000, pp. 1341-1345, vol. 21, No. 7.
Posner, G. H. et al., "Sterocontrolled Synthesis of a Trihydroxylated A Ring as an Immediate Precursor to 1α,2α,25-Trihydroxyvitamin D$_3$", J. Org. Chem., 1991, pp. 4339-4341, vol. 56.
Posner, G. H. et al., "New Vitamin D$_3$ Derivatives with Unexpected Antiproliferatve Activity: 1-(Hydroxymethyl)-25-hydroxyvitamin D$_3$ Homologs", J. Med. Chem., 1992, pp. 3280-3287, vol. 35.
Dai H. et al., "Synthetic Approaches to Vitamin D", Synthesis, 1994, pp. 1383-1397.
Posner, G. H. et al., "Sterocontrolled Total Synthesis of Calcitriol Derivatives: 1,25-Dihydroxy-2-(4'-hydroxybutyavitamin D$_3$ Analogs of an Osteoporosis Drug", J. Org. Chem., 1994, pp. 7855-7861. vol. 59.
Posner, G. H. et al., "1α,25-Dihydroxyvitamin D$_3$ Hybrid Analogs with Structural Changes at Both the A-Ring and the C,D-Ring Sidechain. II", Bioorganic & Medicinal Chemistry Letters, 1995, pp. 2163-2168, vol. 5, No. 18.
Posner. G. H. et al., "1α,25-Dihydroxyvitamin D$_3$ Hybrid Analogs with Structural Changes at Both the A-Ring and the C,D-Ring Sidechain", Bioorganic & Medicinal Chemistry Letters, 1994, pp. 2919-2924, vol. 4, No. 24.
Posner, G.H. at al.. "1α,25-Dihydroxyvitamin D$_3$ Analogs Featuring Aromatic and Heteroaromatic Rings: Design, Synthesis and Preliminary Biological Testing", J. Med. Chem., 1995, pp. 4529-4537, vol. 38.
Posner, G. H., "New vitamin D analogues", Nephrol Dial Transplant, 1998, pp. 32-36, vol. 11, Suppl. 3. Peleg, S. et al, "A 20-Epi Side Chain Restores Growth-Regulatory and Transcriptional Activities of an A Ring-Modified Hybrid Analog of 1α,25-Dihydroxyvitamin D$_3$ Without Increasing Its Affinity to the Vitamin D Receptor", Journal of Cellular Biochemistry, 1996, pp. 149-161, vol. 63.
Posner, G. H. et al., "Antiproliferative Hybrid Analogs of the Hormone 1α,25-Dihydroxyvitamin D$_3$ Design, Synthesis, and Preliminary Biological Evaluation", J. Org. Chem., 1997, pp. 3299-3314, vol. 62.
Posner, G. H. et al., "Noncalcemic, Antiproliferative, Transcriptionally Active, 24-Fluroinated Hybrid Analogues of the Hormone 1α,25-Dihydroxyvitamin D$_3$. Synthesis and Preliminary Biological Evaluation", Journal of Medicinal Chemisrty, 1998, pp. 3008-3014, vol. 41. No. 18.
Peleg. S. et al, "Differential Use of Transcription Activation Function 2 Domain of the Vitamin D Receptor by 1,25-Dihydroxyvitamin D$_3$ and It's A Ring-Modified Analogs", Molecluar Endocrinology, 1998, pp. 525-535, vol. 12, No. 4.

(Continued)

*Primary Examiner* — Barbara P Badio
(74) *Attorney, Agent, or Firm* — Marshall, Gerstein & Borun LLP

(57) ABSTRACT

The present invention provides novel D-ring and side-chain analogs of 1α,25-dihydroxyvitamin D$_3$, compositions comprising these compounds and methods of using these compounds as selective inhibitors of CYP24. In particular, the compounds of the invention are useful for treating diseases which benefit from a modulation of the levels of 1α,25-dihydroxyvitamin D$_3$, for example, cell-proliferative disorders.

21 Claims, 13 Drawing Sheets

OTHER PUBLICATIONS

Posner, G. H. et al., "Vitamin D Endocrine System Structural, Biological, Genetic and Clinical Aspects", Proceedings of Eleventh Workshop on Vitamin D, Nashville, Tennessee, May 27-Jun. 1, 2000, pp. 3-10, Norman, A. W. et al. Eds. Printing and Reprographics, University of California, Riverside, USA.

Posner. G. H. et al., "A Non-Calcemic Sulfone Version of the Vitamin $D_3$ Analogue Seocatcitol (EB 1089): Chemical Synthesis, Biological Evaluation and Potency Enhancement of the Anticancer Drug Adramycin", Bioorganic & Medicinal Chemistry, 2001, pp. 2385-2371, vol. 9.

Hofer, H. et al., "Biological Effects of 1α-Hydroxy-and 1β-(Hydroxymethyl)-Vitamin D Compounds Relevant for Potential Colorectal Cancer Therapy", The Journal of Pharmacology and Experimental Therapeutics, 1999, pp. 450-455, vol. 291, No. 2.

Boyan, B. D. et al., "1,25-$(OH)_2D_3$ modulates growth plate chondrocytes via membrane receptor-rneiated protein kinase C by a mechanism that involves changes in phospholipid metabolism and the action of arachidonic acid and $PGE_2$", Steroids, 1999, pp. 129-138, vol. 84.

Posner, G. H. et al, "2,2-Disubstituted Analouges of the Natural Hormone 1α,25-Dihydroxyvitamin $D_3$ Chemistry and Biology", Bioorganic & Medicinal Chemistry, 2002, pp. 2353-2385, vol. 10.

Hatcher, M. A. et al., "(3,3)-Sigmatropic rearrangements: short, stereocontrolled syntheses of functionalized vitamin $D_3$ side-chain units", Tetrahedron Letters, 2002, pp. 5009-5012, vol. 43.

Guyton, K. Z. et al., "Vitamin D and Vitamin D Analogs as Cancer Chemopreventive Agents", Nutrition Reviews, 2003, pp. 1-12, vol. 81, No. 7.

Hilpert, H. et al, "Novel versatile approach to an enantiopure 19-*nor*, *des*-C,D vitamin $D_3$ derivative", Tetrahedron, 2001, pp. 881-894, vol. 57.

Posner, G. H. et al., "2-Fluoroalkyl A-Ring Analogs of 1,25-Dihydroxyvitamin $D_3$-Sterocontrolled Total Synthesis via Intramolecular and Intermolecular Diels-Alder Cycloadditions. Preliminary Biological Testing", J. Org. Chem., 1995, pp. 4817-4828, vol. 60.

Peleg, S. et al, "Vitamin D Analogs as Modulators of Vitamin D Receptor Action", Current Topics in Medicinal Chemistry, 2003, pp. 1-20, vol. 3.

Guyton, K. Z. et al, "Cancer Chemoprevention Using Natural Vitamin D and Synthetic Analogs". Annu. Rev. Pharmacol. Toxicol., 2001, pp. 421-442, vol. 41.

Posner. G. H. et al., "Conceptually New Sulfone Analogues of the Hormone 1α,25-Dihydroxyvitamin $D_3$: Synthesis and Preliminary Biological Evaluation", Journal of Medicinal Chemistry, 1999, pp. 3425-3435, vol. 42, No. 18.

Posner, G. H. et al., "Conceptually New 20-epi-22-Oxa Sulfone Analogues of the Hormone 1α, 25-Dihydroxyvitamin $D_3$ Synthesis and Biological Evaluation", Journal of Medicinal Chemistry, 2000, pp. 3581-3588, vol. 43, No. 19.

Posner, G. H. et al., "Conceptually New Low-Calcemic Oxime Analogues of the Hormone 1α,25-Dthydroxyvitamin $D_3$ Synthesis and Biological Testing", J. Med. Chem., 2002, pp. 1723-1730, vol. 45.

Crawford, K. R., "Design, Synthesis, and Preliminary Biological Evaluation of Analogs of 1α,25-Dihydroxyvitamin $D_3$ Modifications to the A-Ring and C,D-Ring Side Chain", Ph.D. Thesis, Johns Hopkins University, 2001, pp. 13-56 and 51-55.

Wang, Q., "Part I: Noncalcemic, Antiproliferative, Transcriptionally Active Hybrid Analogs of the Hormone 1α,25-Dihydroxyvitamin $D_3$: Design, Synthesis, and Preliminary Biological Evaluation", Ph.D. Thesis, Johns Hopkins University, 2000, pp. 39-57.

Shuster et al. "Selective Inhibition of Vitamin D Hydroxylases in Human Keratinocytes", Steroids, 2001, pp. 409-422, vol. 66.

Haider, S., et al. "Synthesis and Evaluation of Steroidal Hydroxamic Acids as Inhibitiors of P450 17 (17 α-Hydroxylase/C17-20-Lyase)", Arch. Pharm. Pharm. Med. Chem., 2001, pp. 138-140, vol. 334.

* cited by examiner

25-$SO_2$-SUBSTITUTED ANALOGS OF 1μ,25-DIHYDROXYVITAMIN $D_3$

This invention was made with government support under NIH Grant Number CA44530. The government has certain rights in the invention. This application claims the benefit under 35 USC §119(e) from U.S. provisional patent application Ser. No. 60/433,951, filed Dec. 18, 2002

FIELD OF THE INVENTION

The present invention relates to novel analogs of the hormone 1α,25-dihydroxyvitamin $D_3$ that show selective inhibition of the enzyme CYP24, to pharmaceutical and diagnostic compositions containing them and to their medical use, particularly in the treatment and/or prevention of cancer, dermatological disorders, bone disorders, thyroid disorders, wound healing and osteoporosis.

BACKGROUND OF THE INVENTION

The vitamin D metabolic pathway is part of a vital endocrine system that is highly regulated at certain stages and produces metabolites that control the secretion of the parathyroid gland hormones (Beckman, M., and DeLuca, H. (1997) *Methods in Enzymol.* 282, 200-223; Jones, G., Strugnell, S., and DeLuca, H. (1998) *Physiol. Rev.* 78, 1193-1231). 1α,25-Dihydroxyvitamin $D_3$, also known as calcitriol (see below), a hormone produced in the vitamin D pathway, regulates phosphate and calcium levels in the blood which in turn control bone mass, the state of bones, and affects cellular differentiation in the skin and the immune system (Armbrecht, H. J., Okuda, K., Wongsurawat, N., Nemani, R., Chen, M., and Boltz, M. (1992) *J. Steroid Biochem. Molec. Biol.* 43, 1073-1081). In the vitamin D pathway, cytochrome P450s are enzymes that introduce functional groups by hydroxylation, usually at positions 1, 25, and 24, of vitamin $D_3$ (Beckman, M., and DeLuca, H. (1997) *Methods in Enzymol.* 282, 200-223).

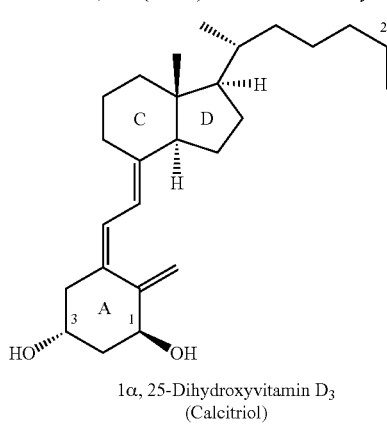

1α, 25-Dihydroxyvitamin $D_3$
(Calcitriol)

1α,25-Dihydroxyvitamin $D_3$ is converted to 1α,24,25-trihydroxy-$D_3$ by a mitochondrial P450 known as CYP24 (Bell, N. H., (1998) *J. Bone Miner. Res.* 13, 350-352). CYP24 is induced by 1α,25-dihydroxy-$D_3$ and is found in the kidney as well as other vitamin D target tissues such as the parathyroid cells, keratinocytes, osteoblasts, and enteroctyes (Jones, G., Strugnell, S., and DeLuca, H. (1998) *Physiol. Rev.* 78, 1193-1231).

The biological effects of 1α,25-dihydroxyvitamin $D_3$ (calcitriol) and its synthetic analogs are mediated by the nuclear vitamin D receptor (VDR). Calcitriol has an important role in the antiproliferative and growth regulatory effects on normal and neoplastic cells (for e.g. prostate cancer cells). VDR ligands have potential widespread clinical application, however in many cases, hypercalcemia develops as a side effect which prevents sustained systemic administration. Inhibiting the catabolism of calcitriol and its analogs is expected to lengthen the biological lifetime of these compounds and thus to allow smaller amounts of them to be used for effective human chemotherapy. Such smaller dosing will avoid, or at least minimize, the hypercalcemic toxicity associated with medicinal use of these compounds. Further inhibition of the catabolism of 1α,25-dihydroxyvitamin $D_3$ increases the endogenous levels of this hormone, which will also have beneficial therapeutic effects.

There is a need for compounds that mimic and modulate the activity of calcitriol, and analogs thereof, yet do not possess undesirable side effects, for example, hypercalcemia.

SUMMARY OF THE INVENTION

It has been found that certain 25-$SO_2$-substituted analogs of 1α,25-dihydroxyvitamin $D_3$ show desirable therapeutic activity as analogs of calcitriol.

The present invention therefore includes compounds selected from one or more of compounds of Formulae Ia and Ib, and pharmaceutically acceptable salts, solvates and prodrugs thereof:

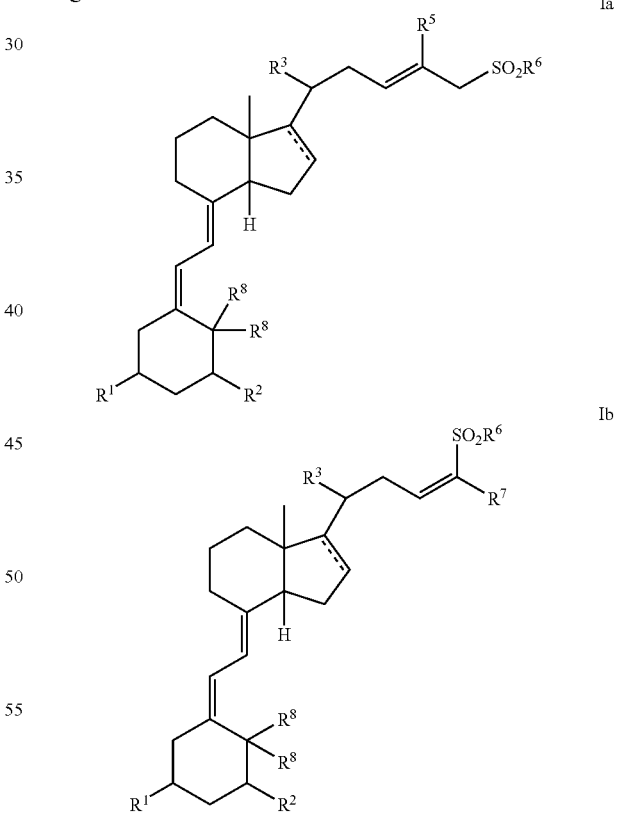

wherein
$R^1$ and $R^2$ are independently selected from the group consisting of OH, $OC_{1-4}$alkyl, and halo;
$R^3$ is $C_{1-4}$alkyl;
$R^5$ is selected from the group consisting of H, Cl, F, $C_{1-4}$alkyl, $OC_{1-4}$alkyl, $SC_{1-4}$alkyl, $SO_2C_{1-4}$alkyl, $P(O)(OC_{1-4}alkyl)_2$ and SCN;

$R^6$ is selected from the group consisting of $C_{1-4}$alkyl, unsubstituted Ph and Ph substituted with 1-2 groups independently selected from $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl$)(C_{1-4}$alkyl$)$ and CN;

$R^7$ is selected from the group consisting of H, Cl, F, $C_{1-4}$alkyl, $OC_{1-4}$alkyl, $SC_{1-4}$alkyl, $SO_2C_{1-4}$alkyl, $P(O)(OC_{1-4}$alkyl$)_2$ and SCN;

$R^8$ are either both H or together form $=CH_2$; and

==== represents a single or a double bond, with the proviso that when $R^5$ is F, ==== is a single bond.

The present invention also includes compounds selected from one or more of compounds of Formula II, and pharmaceutically acceptable solvates and prodrugs thereof:

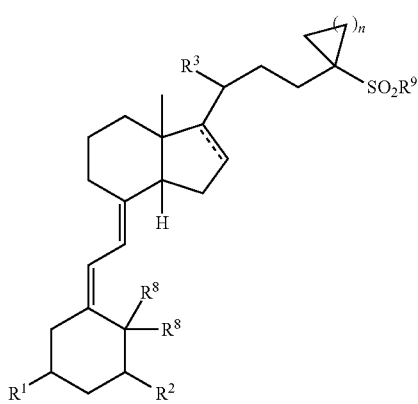

II wherein $R^1$ and $R^2$ are independently selected from the group consisting of OH, $OC_{1-4}$alkyl, and halo;

$R^3$ is $C_{1-4}$alkyl;

$R^8$ are either both H or together form $=CH_2$;

$R^9$ is $C_{1-4}$alkyl;

n is 1-3; and

==== represents a single or a double bond, with the proviso that when n is 1 and ==== represents a double bond, $R^9$ is not t-butyl.

Also included within the scope of the present invention are compounds selected from one or more of compounds of Formula III, and pharmaceutically acceptable salts, solvates and prodrugs thereof:

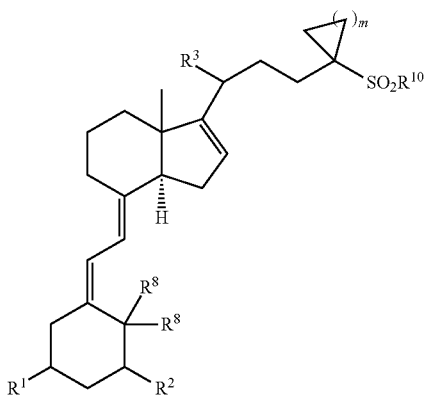

III wherein $R^1$ and $R^2$ are independently selected from the group consisting of OH, $OC_{1-4}$alkyl, and halo;

$R^3$ is $C_{1-4}$alkyl;

$R^8$ are either both H or together form $=CH_2$;

$R^{10}$ is selected from the group consisting of unsubstituted Ph and Ph substituted with 1-2 groups independently selected from $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl$)(C_{1-4}$alkyl$)$ and CN; and m is 1-3.

The present invention also involves compounds selected from one or more of compounds of Formula IV, and pharmaceutically acceptable solvates and prodrugs thereof:

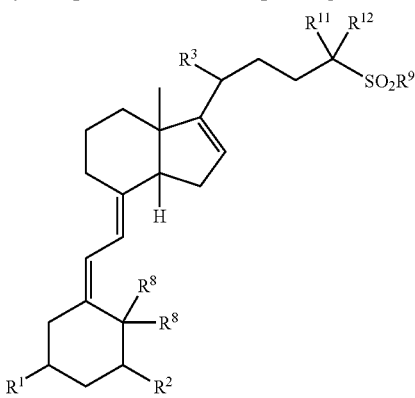

IV wherein $R^1$ and $R^2$ are independently selected from the group consisting of OH, $OC_{1-4}$alkyl, and halo;

$R^3$ is $C_{1-4}$alkyl;

$R^8$ are either both H or together form $=CH_2$;

$R^9$ is $C_{1-4}$alkyl; and $R^{11}$ and $R^{12}$ are independently, $C_{1-2}$alkyl.

Also included within the scope of the present application are compounds selected from one or more of compounds of Formula V, and pharmaceutically acceptable salts, solvates and prodrugs thereof:

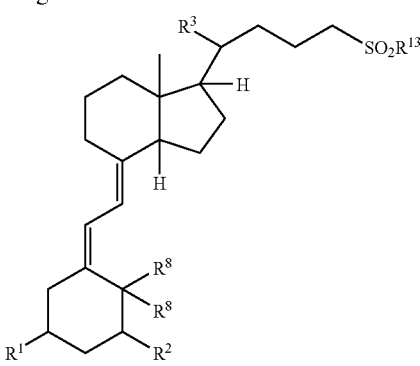

V wherein $R^1$ and $R^2$ are independently selected from the group consisting of OH, $OC_{1-4}$alkyl, and halo;

$R^3$ is $C_{1-4}$alkyl;

$R^8$ are either both H or together form $=CH_2$; and $R^{13}$ is Ph substituted with 1-2 groups independently selected from the group consisting of $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl$)(C_{1-4}$alkyl$)$ and CN.

According to another aspect of the present invention, there is provided a pharmaceutical composition comprising a compound of the invention and a pharmaceutically acceptable carrier or diluent.

The compounds of the invention are selective modulators of CYP24, the enzyme that metabolizes 1α,25-dihydroxyvitamin $D_3$. By selectively modulating CYP24, the levels of $1\alpha,25$-dihydroxyvitamin $D_3$ (either endogenous or administered as part of a chemotherapeutic regimen), or an analog of $1\alpha,25$-dihydroxyvitamin $D_3$, will also be modulated. Diseases that benefit from a modulation of the levels of $1\alpha,25$-dihydroxyvitamin $D_3$ can therefore be treated using a modulator of CYP24. By acting preferentially on CYP24, side effects caused by interaction with other enzymes and receptors will be reduced. Accordingly, the present invention provides a method for treating a disease which benefits from a modulation of the levels of $11\alpha,25$-dihydroxyvitamin $D_3$, or an analog of $1\alpha,25$-dihydroxyvitamin $D_3$, comprising administering an effective amount of a compound of the invention to a cell or animal in need thereof. The invention also includes the use of a compound of the invention to treat a disease which benefits from a modulation of the levels of $1\alpha,25$-dihydroxyvitamin $D_3$, or an analog of $1\alpha,25$-dihydroxyvitamin $D_3$. Further, the invention includes a use of a compound of the invention to prepare a medicament to treat a disease which benefits from a modulation of the levels of $1\alpha,25$-dihydroxyvitamin $D_3$, or an analog of $1\alpha,25$-dihydroxyvitamin $D_3$.

Inhibition of CYP24 will inhibit the catabolism of $1\alpha,25$-dihydroxyvitamin $D_3$, or its analogs, which will lengthen the biological lifetime of these compounds and thus allow smaller amounts of them to be used for effective disease treatment. Such smaller dosing will avoid, or at least minimize, the hypercalcemic toxicity associated with medicinal use of $1\alpha,25$-dihydroxyvitamin $D_3$ and its analogs. Further, by inhibiting the catabolism of $1\alpha,25$-dihydroxyvitamin $D_3$, the compounds of the invention will increase the endogenous levels of this hormone, which will result in similar beneficial therapeutic effects. Therefore, in an embodiment, the present invention provides a method for treating a disease which benefits from inhibiting the catabolism of $1\alpha,25$-dihydroxyvitamin $D_3$, or an analog of $1\alpha,25$-dihydroxyvitamin $D_3$, comprising administering an effective amount of a compound of the invention to a cell or animal in need thereof. The invention also includes the use of a compound of the invention to treat a disease which benefits from inhibiting the catabolism of $1\alpha,25$-dihydroxyvitamin $D_3$, or an analog of $1\alpha,25$-dihydroxyvitamin $D_3$. Further, the invention includes a use of a compound of the invention to prepare a medicament to treat a disease which benefits from inhibiting the catabolism of $1\alpha,25$-dihydroxyvitamin $D_3$, or an analog of $1\alpha,25$-dihydroxyvitamin $D_3$.

Diseases which will benefit from a modulation in the levels of $1\alpha,25$-dihydroxyvitamin $D_3$ or its analogs, include, but are not limited to, one or more of the following:
(i) in the parathyroid—hyper- and hypo-parathyroidism, pseudohypo-parathyroidism, Secondary hyperparathyroidism;
(ii) in the pancreas—diabetes;
(iii) in the thyroid—medullary carcinoma;
(iv) in the skin—psoriasis; wound healing;
(v) in the lung—sarcoidosis and tuberculosis;
(vi) in the kidney—chronic renal disease, hypophosphtatemic VDRR, vitamin D dependent rickets;
(vii) in the bone—anticonvulsant treatment, fibrogenisis imperfecta ossium, osteitits fibrosa cystica, osteomalacia, osteoporosis, osteopenia, osteosclerosis, renal osteodytrophy, rickets;
(viii) in the intestine—glucocorticoid antagonism, idopathic hypercalcemia, malabsorption syndrome, steatorrhea, tropical sprue; and
(ix) autoimmune disorders.

In embodiments of the invention, the disease that benefits from a modulation in the levels of $1\alpha,25$-dihydroxyvitamin $D_3$, or an analog of $1\alpha,25$-dihydroxyvitamin $D_3$, is selected from one or more of cancer, dermatological disorders (for example psoriasis), parathyroid disorders (for example hyperparathyroidism and secondary hyperparathyroidism), bone disorders (for example osteoporosis) and autoimmune disorders.

In accordance with a further aspect of the present invention, the disease that benefits from a modulation in the levels of $1\alpha,25$-dihydroxyvitamin $D_3$, or an analog of $1\alpha,25$-dihydroxyvitamin $D_3$, is a cell proliferative disorder. Accordingly, there is provided a method treating a cell proliferative disorder, comprising administering an effective amount of a compound of the invention to a cell or animal in need thereof. The invention also includes a use of a compound of the invention to treat a cell proliferative disorder. The invention further includes a use of a compound of the invention to prepare a medicament to treat a cell proliferative disorder. In an embodiment of the invention, the compounds of the invention are able to treat a cell proliferative disorder by inhibiting cell proliferation and/or promoting cell differentiation.

In another embodiment of the present invention, the disease that benefits from a modulation in the levels of $1\alpha,25$-dihydroxyvitamin $D_3$, or an analog of $1\alpha,25$-dihydroxyvitamin $D_3$, is cancer, Accordingly, the present invention provides a method of treating cancer comprising administering an effective amount of a compound of the invention to a cell or animal in need thereof. The invention also includes a use of a compound of the invention to treat cancer. The invention further includes a use of a compound of the invention to prepare a medicament to treat cancer. In embodiments of the invention, the cancer is selected from one or more of breast cancer, lung cancer, prostate cancer, colon and colorectal cancer, kidney cancer, head and neck cancer, pancreatic cancer, skin cancer, Kaposi's sarcoma and leukemia.

In another aspect, the invention provides a method of modulating CYP24 activity in a cell by administering an effective amount of a compound of the invention to a cell in need thereof. In a further aspect, the invention provides a method of inhibiting CYP24 activity in a cell by administering an effective amount of a compound of the invention to a cell in need thereof. The present invention also provides a use of a compound of the invention to modulate, preferably to inhibit, CYP24 activity. The present invention further provides a use of a compound of the invention to prepare a medicament to modulate CYP24 activity, preferably to inhibit CYP24 activity.

The compounds of the invention can be used alone or in combination with other agents that modulate CYP24 activity, or in combination with other types of treatment (which may or may not modulate CYP24) for diseases that benefit from a modulation in the levels of $1\alpha,25$-dihydroxyvitamin $D_3$, or an analog thereof, and/or an inhibition of the catabolism of $1\alpha,25$-dihydroxyvitamin $D_3$, or an analog thereof. Preferably the compounds of the invention are administered in combination with $1\alpha,25$-dihydroxyvitamin $D_3$ (calcitriol), an analog of $1\alpha,25$-dihydroxyvitamin $D_3$ or other vitamin D receptor agonists. Inhibiting catabolism of vitamin D receptor agonists such as $1\alpha,25$-dihydroxyvitamin $D_3$, or analogs thereof, will lengthen the biological lifetime or efficacy of these therapies and thus to allow smaller amounts of the drug to be used for effective human chemotherapy; such smaller dosing will avoid, or at least to minimize, the hypercalcemic toxicity associated with medicinal use of these compounds. The present invention therefore provides a method of increasing the efficacy of a vitamin D receptor agonist, preferably $1\alpha,25$-dihydroxyvitamin $D_3$, or an analog thereof, comprising co-administering an effective amount of a compound of the invention and an effective amount of the vitamin D receptor agonist, preferably 1α,25-dihydroxyvitamin $D_3$, or an analog thereof. Further the invention includes the use of a compound of the invention to increase the efficacy of a vitamin D receptor agonist, preferably 1α,25-dihydroxyvitamin $D_3$, or an analog thereof, and a use of a compound of the invention to prepare a medicament to increase the efficacy of a vitamin D receptor agonist, preferably 1α,25-dihydroxyvitamin $D_3$, or an analog thereof.

Also included within the scope of the present invention are uses and methods as defined above for a compound of Formula VI:

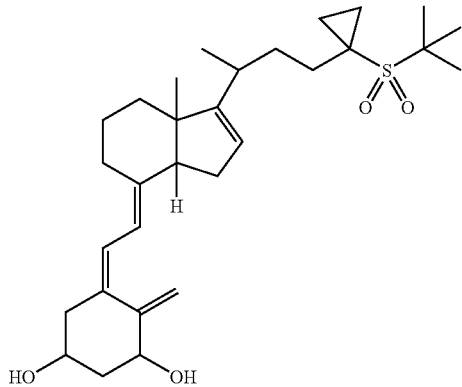

VI

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

I. Definitions

Figure 1:
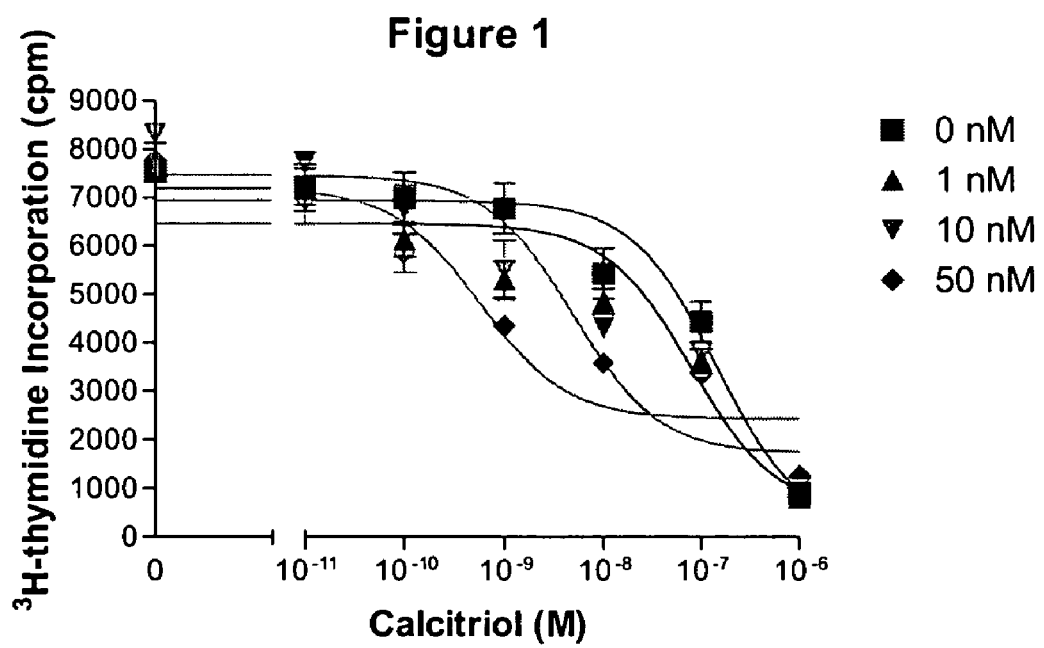
FIG. 1 is a graph showing that compound Va and calcitriol act to inhibit normal human epidermal keratinocytes (NHEK). NHEK were treated with specified concentrations of calcitriol and compound Va for three days. Cells were then incubated with [$^3$H]-thymidine for 18 h at 37° C. in a humidified atmosphere containing 5% $CO_2$. Plates were harvested and radioactivity measured. Dose response curves in the absence of Va, 1 nM Va, 10 nM Va and 50 nM Va are shown.

The term "$C_{1-4}$alkyl" as used herein means straight and/or branched chain alkyl groups containing from one to four carbon atoms and includes methyl, ethyl, propyl, isopropyl, t-butyl and the like.

The term "$C_{1-4}$alkoxy" as used herein means straight and/or branched chain alkoxy groups containing from one to four carbon atoms and includes methoxy, ethoxy, propyoxyl, isopropyloxy, t-butoxy and the like.

The term "$C_{3-5}$cycloalkyl as used herein means a 3-5-membered saturated carbon ring.

The term "halo" as used herein means halogen and includes chloro, flouro, bromo, iodo and the like.

The term "pharmaceutically acceptable" means compatible with the treatment of animals, in particular, humans.

The term "pharmaceutically acceptable salt" means an acid addition salt which is suitable for or compatible with the treatment of patients.

The term "pharmaceutically acceptable acid addition salt" as used herein means any non-toxic organic or inorganic salt of any base compound of the invention, or any of its intermediates. Basic compounds of the invention that may form an acid addition salt include those having a basic nitrogen, for example $NH_2$ and $NHC_{1-4}$alkyl. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of the compounds of the invention are more soluble in water and various hydrophilic organic solvents, and generally demonstrate higher melting points in comparison to their free base forms. The selection of the appropriate salt will be known to one skilled in the art. Other non-pharmaceutically acceptable salts, e.g. oxalates, may be used, for example, in the isolation of the compounds of the invention, for laboratory use, or for subsequent conversion to a pharmaceutically acceptable acid addition salt.

The term "solvate" as used herein means a compound of the invention, or a pharmaceutically acceptable salt of a compound of the invention, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate".

The term "compound(s) of the invention" as used herein means compound(s) of Formulae I, II, III, IV and/or V, and/or pharmaceutically acceptable salts (where applicable), solvates and/or prodrugs thereof.

It is to be clear that the present invention includes pharmaceutically acceptable salts (where applicable), solvates and prodrugs of compounds of the invention and mixtures comprising two or more of compounds the compounds of the invention, pharmaceutically acceptable salts of the compounds of the invention (where applicable), pharmaceutically acceptable solvates of compounds of the invention and prodrugs of compounds of the invention.

The term an "effective amount" or a "sufficient amount" of an agent as used herein is that amount sufficient to effect beneficial or desired results, including clinical results, and, as such, an "effective amount" depends upon the context in which it is being applied. For example, in the context of administering an agent that inhibits cancer cell proliferation, an effective amount of an agent is, for example, an amount sufficient to achieve such a reduction in cancer cell proliferation as compared to the response obtained without administration of the agent.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder.

The term "modulate" as used herein includes the inhibition or suppression of a function or activity (such as cell proliferation) as well as the enhancement of a function or activity.

To "inhibit" or "suppress" or "reduce" a function or activity, such as cancer cell proliferation, is to reduce the function or activity when compared to otherwise same conditions except for a condition or parameter of interest, or alternatively, as compared to another conditions.

The term "animal" as used herein includes all members of the animal kingdom including human. The animal is preferably a human.

The term "a cell" as used herein includes a plurality of cells. Administering a compound to a cell includes in vivo, ex vivo and in vitro treatment.

The term "cancer cells" as used herein includes all forms of cancer or neoplastic disease.

II. Compounds of the Invention

Novel compounds showing selective inhibition of the enzyme CYP24 have been prepared. As such, the compounds of the invention are useful for treating cell proliferative diseases, such as cancer.

Accordingly, the present invention provides compounds selected from one or more of compounds of Formula Ia and Ib, and pharmaceutically acceptable salts, solvates and prodrugs thereof:

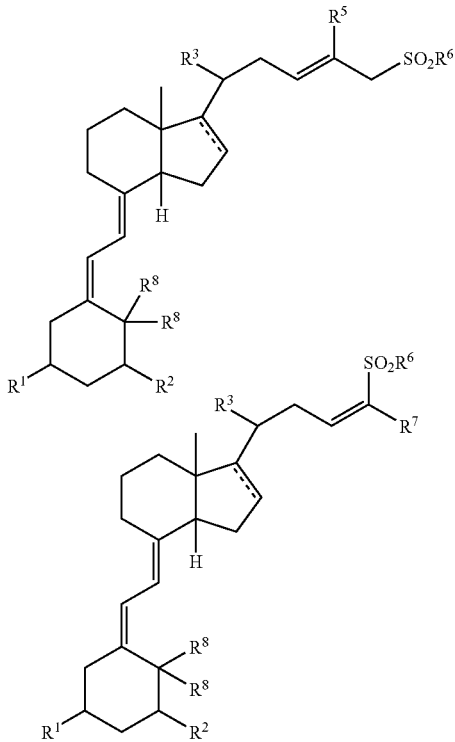

wherein
$R^1$ and $R^2$ are independently selected from the group consisting of OH, $OC_{1-4}$alkyl, and halo;
$R^3$ is $C_{1-4}$alkyl;
$R^5$ is selected from the group consisting of H, Cl, F, $C_{1-4}$alkyl, $OC_{1-4}$alkyl, $SC_{1-4}$alkyl, $SO_2C_{1-4}$alkyl, $P(O)(OC_{1-4}alkyl)_2$ and SCN;
$R^6$ is selected from the group consisting of $C_{1-4}$alkyl, unsubstituted Ph and Ph substituted with 1-2 groups independently selected from $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}alkyl)(C_{1-4}alkyl)$ and CN;
$R^7$ is selected from the group consisting of H, Cl, F, $C_{1-4}$alkyl, $OC_{1-4}$alkyl, $SC_{1-4}$alkyl, $SO_2C_{1-4}$alkyl, $P(O)(OC_{1-4}alkyl)_2$ and SCN;
$R^8$ are either both H or together form $=CH_2$; and
==== represents a single or a double bond,
with the proviso that when $R^5$ is F, ==== is a single bond.

The compounds of Formula Ia and Ib include those in which $R^1$ and $R^2$ are independently selected from the group consisting of OH, $OC_{1-4}$alkyl, and halo. In an embodiment of the invention, $R^1$ and $R^2$ are independently selected from the group consisting of OH, $OCH_3$, and fluoro. In another embodiment, $R^1$ and $R^2$ are both OH.

The present invention includes compounds of Formula Ia and Ib wherein $R^3$ is $C_{1-4}$alkyl. An embodiment of the invention is where $R^3$ is $CH_3$.

The present invention also includes compounds of the Formula Ia wherein $R^5$ is selected from the group consisting of H, F, Cl, $C_{1-4}$alkyl, $OC_{1-4}$alkyl, $SC_{1-4}$alkyl, $SO_2C_{1-4}$alkyl, $P(O)(OC_{1-4}alkyl)_2$ and SCN. In embodiments of the invention, $R^5$ is selected from the group consisting of H, F, Cl, $CH_3$, $OCH_3$, $SCH_3$ and SCN. Further embodiments include those compounds of Formula Ia where $R^5$ is $CH_3$ or Cl.

The present invention includes compounds of the Formula Ia and Ib wherein $R^6$ is selected from the group consisting of $C_{1-4}$alkyl, unsubstituted Ph and Ph substituted with 1-2 groups independently selected from $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}alkyl)(C_{1-4}alkyl)$ and CN. In embodiments of the invention the compounds of the Formula Ia and Ib include those wherein $R^6$ is selected from the group consisting of $C_{1-4}$alkyl, unsubstituted Ph and Ph substituted with 1-2 groups independently selected from $CH_3$, $OCH_3$, OH, $CF_3$, $OCF_3$, halo, SH, $SCH_3$, $NH_2$, $NHCH_3$, $N(CH_3)_2$ and CN. Further embodiments of the invention include compounds of the Formula Ia and Ib wherein $R^6$ is $C_{1-4}$alkyl or an unsubstituted Ph. A still further embodiment is where $R^6$ is t-butyl or unsubstituted Ph.

The present invention includes compounds of the Formula Ib wherein $R^7$ is selected from the group consisting of H, Cl, F, $C_{1-4}$alkyl, $OC_{1-4}$alkyl, $SC_{1-4}$alkyl, $SO_2C_{1-4}$alkyl, $P(O)(OC_{1-4}alkyl)_2$ and SCN. In embodiments of the present invention, $R^7$ is selected from the group consisting of H, Cl, F, $CH_3$, $OCH_3$, $SCH_3$, $SO_2CH_3$ and SCN. Further embodiments include those compounds of Formula Ib where $R^7$ is Cl, F, $CH_3$ or $OCH_3$.

Also included within the scope of the present invention are compounds of Formula Ia and Ib wherein $R^8$ are either both H or together form $=CH_2$. In embodiments of the invention $R^8$ together form $=CH_2$.

In the compounds of Formula Ia and Ib, ==== represents a single or a double bond. In embodiments of the invention ==== represents a double bond. It is a further embodiment of the invention that when ==== represents a single bond in a compound of Formula Ia, $R^5$ is F.

The present invention also includes compounds selected from one or more of compounds of Formula II, and pharmaceutically acceptable solvates and prodrugs thereof:

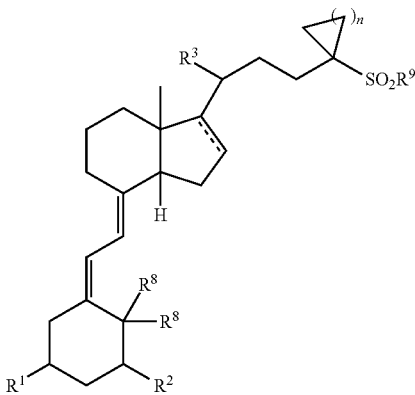

wherein
$R^1$ and $R^2$ are independently selected from the group consisting of OH, $OC_{1-4}$alkyl, and halo;
$R^3$ is $C_{1-4}$alkyl;
$R^8$ are either both H or together form $=CH_2$;
$R^9$ is $C_{1-4}$alkyl;
n is 1-3; and
==== represents a single or a double bond,
with the proviso that when n is 1 and ==== represents a double bond, $R^9$ is not t-butyl.

The compounds of Formula II include those in which $R^1$ and $R^2$ are independently selected from the group consisting of OH, $OC_{1-4}$alkyl, and halo. In an embodiment of the invention, $R^1$ and $R^2$ are independently selected from the group consisting of OH, $OCH_3$, and fluoro. In another embodiment, $R^1$ and $R^2$ are both OH.

The present invention includes compounds of Formula II wherein $R^3$ is $C_{1-4}$alkyl. In an embodiment of the invention, $R^3$ is $CH_3$.

Also included within the scope of the present invention are compounds of Formula II wherein $R^8$ are either both H or together form $=CH_2$. In embodiments of the invention $R^8$ together form $=CH_2$.

The present invention also includes compounds of Formula II wherein $R^9$ is $C_{1-4}$alkyl; and n is 1-3. In an embodiment of the invention, $R^9$ is t-butyl and n is 2.

In the compounds of Formula II, ==== represents a single or a double bond. In embodiments of the invention ==== represents a double bond. It is a further embodiment of the invention that when ==== represents a single bond in a compound of Formula II, $R^9$ is t-butyl.

Also included within the scope of the present invention is a compound selected from one or more of compounds of Formula III, and pharmaceutically acceptable salts, solvates and prodrugs thereof

III

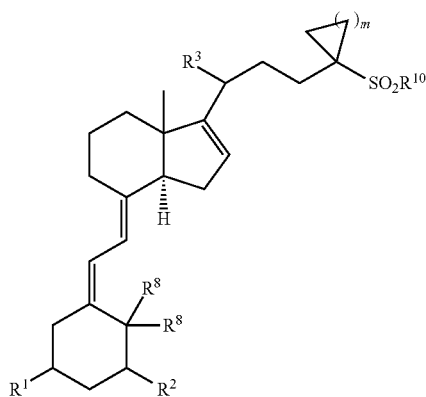

$R^1$ and $R^2$ are independently selected from the group consisting of OH, $OC_{1-4}$alkyl, and halo;
$R^3$ is $C_{1-4}$alkyl;
$R^8$ are either both H or together form $=CH_2$;
$R^{10}$ is selected from the group consisting of unsubstituted Ph and Ph substituted with 1-2 groups independently selected from $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl$)(C_{1-4}$alkyl$)$ and CN; and
m is 1-3.

The compounds of Formula III include those in which $R^1$ and $R^2$ are independently selected from the group consisting of OH, $OC_{1-4}$alkyl, and halo. In an embodiment of the invention, $R^1$ and $R^2$ are independently selected from the group consisting of OH, $OCH_3$, and fluoro. In another embodiment, $R^1$ and $R^2$ are both OH.

The present invention includes compounds of Formula III wherein $R^3$ is $C_{1-4}$alkyl. In an embodiment of the invention, $R^3$ is $CH_3$.

Also included within the scope of the present invention are compounds of Formula III wherein $R^8$ are either both H or together form $=CH_2$. In embodiments of the invention $R^8$ together form $=CH_2$.

The present invention also includes compounds of Formula III wherein $R^{10}$ is selected from the group consisting of unsubstituted Ph and Ph substituted with 1-2 groups independently selected from $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl$)(C_{1-4}$ alkyl) and CN. In embodiments of the invention, $R^{10}$ is either unsubstituted Ph or substituted Ph and the substituent is located at a position other than that ortho to the $SO_2$ group. Further embodiments of the invention include compounds of the Formula III wherein $R^{10}$ is either an unsubstituted Ph or a Ph substituted with 1-2 groups independently selected from methyl, methoxy, OH, $CF_3$, $OCF_3$, halo, $NH_2$ and $N(CH_3)_2$. In another embodiment, $R^{10}$ is either unsubstituted Ph or Ph substituted with 1-2 groups independently selected from methyl, Cl and F. In still further embodiments of the invention, $R^{10}$ is selected from the group consisting of phenyl, 4-chlorophenyl, 3,4-dichloropheny, 4-fluorophenyl, 4-methoxyphenyl and 4-methylphenyl.

The present invention includes compounds of the Formula III wherein m is 1-3. In embodiments of the invention, m is 1 or 2.

The present invention also involves a compound selected from one or more of compounds of Formula IV, and pharmaceutically acceptable solvates and prodrugs thereof:

IV

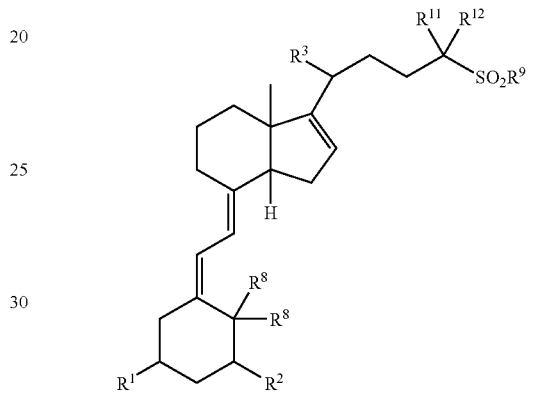

wherein
$R^1$ and $R^2$ are independently selected from the group consisting of OH, $OC_{1-4}$alkyl, and halo;
$R^3$ is $C_{1-4}$alkyl;
$R^8$ are either both H or together form $=CH_2$;
$R^9$ is $C_{1-4}$alkyl; and
$R^{11}$ and $R^{12}$ are independently, $CH_{1-2}$alkyl.

The compounds of Formula IV include those in which $R^1$ and $R^2$ are independently selected from the group consisting of OH, $OC_{1-4}$alkyl, and halo. In an embodiment of the present invention, $R^1$ and $R^2$ are independently selected from the group consisting of OH, $OCH_3$, and fluoro. In another embodiment, $R^1$ and $R^2$ are both OH.

The present invention includes compounds of Formula IV wherein $R^3$ is $C_{1-4}$alkyl. In an embodiment of the invention, $R^3$ is $CH_3$.

Also included within the scope of the present invention are compounds of Formula IV wherein $R^8$ are either both H or together form $=CH_2$. In embodiments of the invention $R^8$ together form $=CH_2$.

The present invention includes compounds of Formula IV wherein $R^9$ is $C_{1-4}$alkyl. In embodiments of the invention $R^9$ is t-butyl.

The present invention also includes compounds of Formula IV wherein $R^{11}$ and $R^{12}$ are independently, $C_{1-2}$alkyl. In embodiments of the invention, both $R^{11}$ and $R^{12}$ are methyl. When $R^1$ and $R^{12}$ are different, the carbon to which they are attached is chiral. The invention extends to both R and S stereoisomers at this center and mixtures thereof.

Also included within the scope of the present application are compounds selected from one or more of compounds of Formula V, and pharmaceutically acceptable salts, solvates and prodrugs thereof:

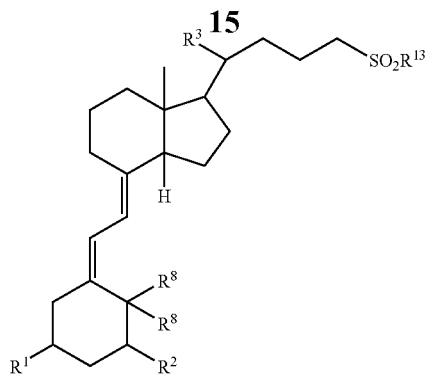

wherein
R¹ and R² are independently selected from the group consisting of OH, $OC_{1-4}$alkyl, and halo;
R³ is $C_{1-4}$alkyl;
R⁸ are either both H or together form =$CH_2$; and
R¹³ is Ph substituted with 1-2 groups independently selected from the group consisting of $C_{1-4}$alkyl, $OC_{1-4}$alkyl; OH, $CF_3$, $OCF_3$, halo, SH, $SC_{1-4}$alkyl, $NH_2$, $NHC_{1-4}$alkyl, $N(C_{1-4}$alkyl$)(C_{1-4}$alkyl$)$ and CN.

The compounds of Formula V include those in which R¹ and R² are independently selected from the group consisting of OH, $OC_{1-4}$alkyl, and halo. In an embodiment of the invention, R¹ and R² are independently selected from the group consisting of OH, $OCH_3$, and fluoro. In another embodiment, R¹ and R² are both OH.

The present invention includes compounds of Formula V wherein R³ is $C_{1-4}$alkyl. In an embodiment of the invention, R³ is $CH_3$.

Also included within the scope of the present invention are compounds of Formula V wherein R⁸ are either both H or together form =$CH_2$. In embodiments of the invention R⁸ together form =$CH_2$.

The present invention includes compounds of Formula V wherein R¹³ is Ph substituted with 1-2 groups independently selected from the group consisting of $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl$)(C_{1-4}$alkyl$)$ and CN. In an embodiment of the invention, R¹³ is a substituted Ph wherein the substituent is located at a position other than ortho to the $SO_2$ group. Further embodiments of the invention include compounds of the Formula V wherein R¹³ is Ph substituted with 1-2 groups independently selected from methyl, methoxy, OH, $CF_3$, $OCF_3$, halo, $NH_2$ and $NMe_2$. In another embodiment, R¹³ is Ph substituted with 1-2 groups independently selected from methoxy, Cl and F. In specific embodiments of the invention, R¹³ is selected from the group consisting of 4-chlorophenyl, 3,4-dichloropheny, 4-fluorophenyl, 4-methoxyphenyl and 4-methylphenyl. In another embodiment, R¹³ is 4-methoxyphenyl or 4-fluorophenyl.

All of the compounds of the invention have more than one asymmetric centre. Where the compounds according to the invention possess more than one asymmetric centre, they may exist as diastereomers. It is to be understood that all such isomers and mixtures thereof in any proportion are encompassed within the scope of the present invention. The stereochemistry of the compounds of the invention is preferably that of natural 1α,25-dihydroxyvitamin $D_3$. Therefore, in a preferred embodiment, the present invention provides compounds of Formulae Ia, Ib, II, III, IV and V with the relative stereochemistry as shown below, and pharmaceutically acceptable salts (where appropriate) solvates and prodrugs thereof:

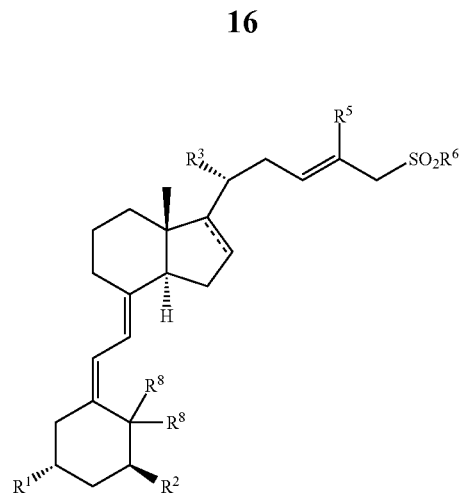

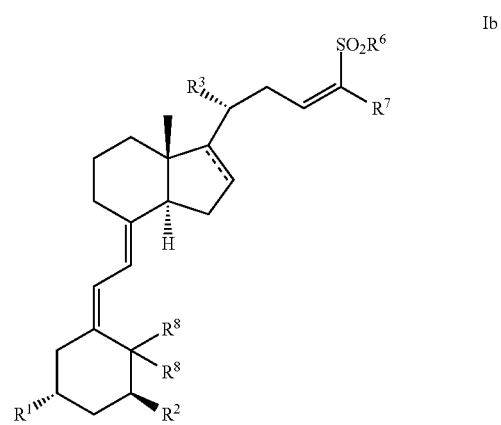

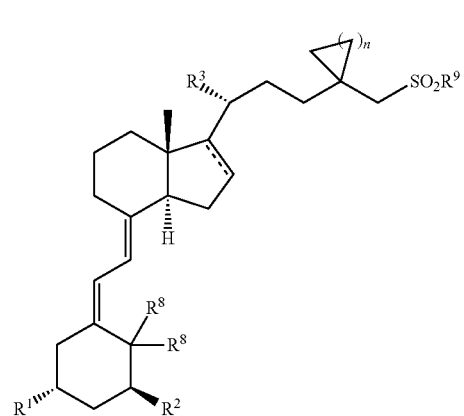

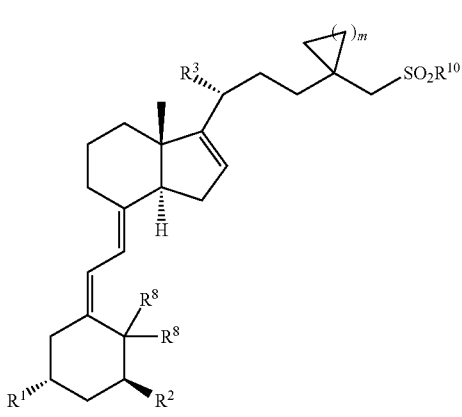

IV

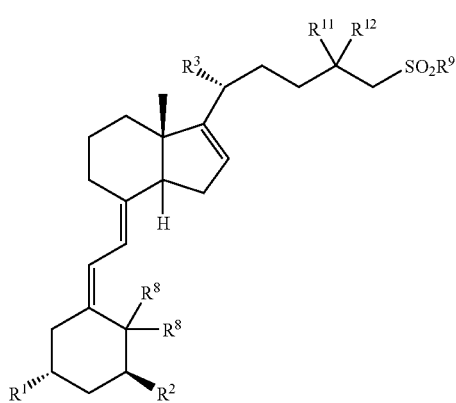

V

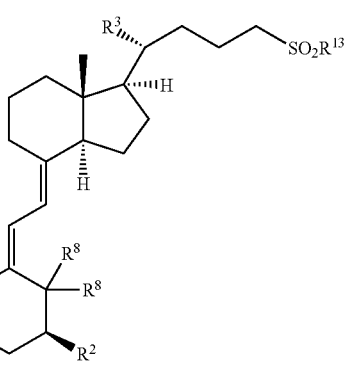

wherein $R^1$-$R^3$, $R^5$-$R^{13}$, ====, m and n are as previously defined above. When ==== is a single bond in the compounds of Formulae Ia, Ib and II, it is an embodiment of the invention that the stereochemistry at carbon 17 is that of natural 1α,25-dihydroxyvitamin $D_3$ (i.e. R).

It is to be understood that while the relative stereochemistry of the compounds of the invention is preferably as shown above, such compounds of the invention may also contain certain amounts (e.g. less than 20%, preferably less than 10%, more preferably less than 5%) of compounds of the invention having alternate stereochemistry. For example, a compound of the invention having the 1α,30β-stereochemistry of natural 1α,25-Dihydroxyvitamin $D_3$, shown above, may contain less then 20%, preferably less then 10%, more preferably less then 5%, of a compound of the invention having the unnatural 1β,3α-stereochemistry.

In specific embodiments of the present invention, the compounds of the invention are selected from one or more of:

Ia(i)

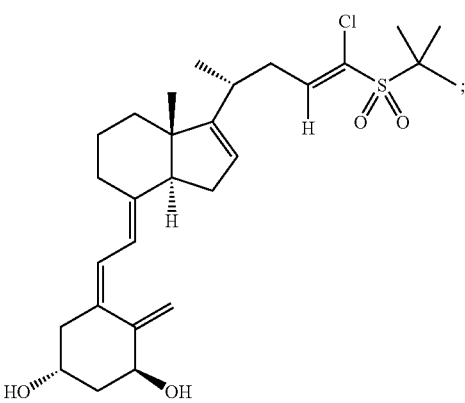

Ia(ii)

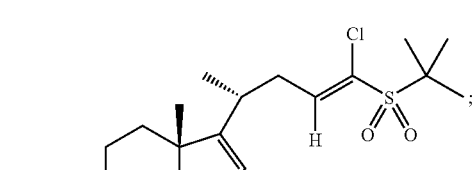

Ia(iii)

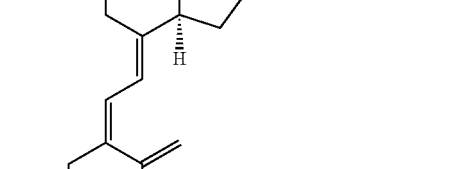

Ia(iv)

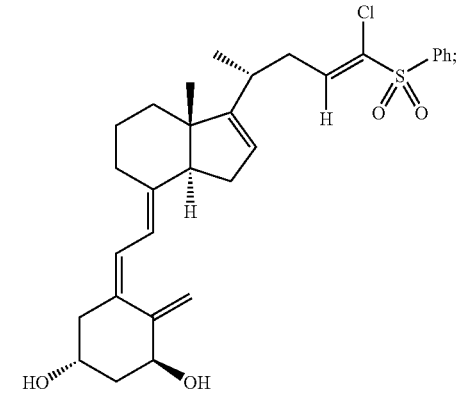

Ib(i)

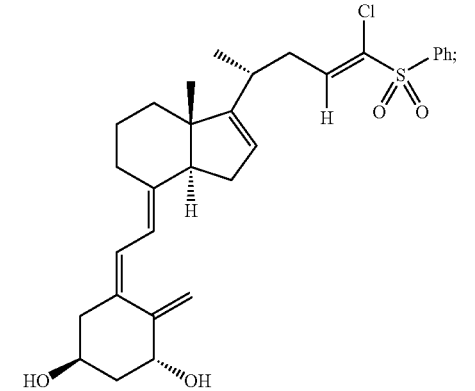

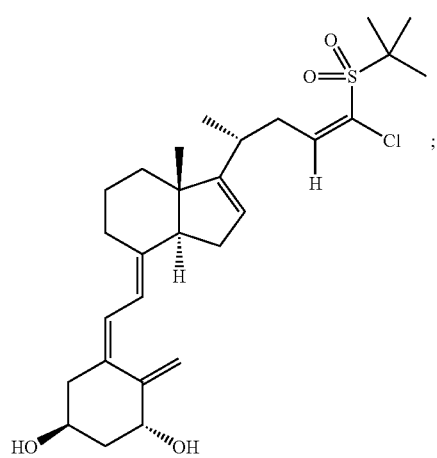 Ib(ii)
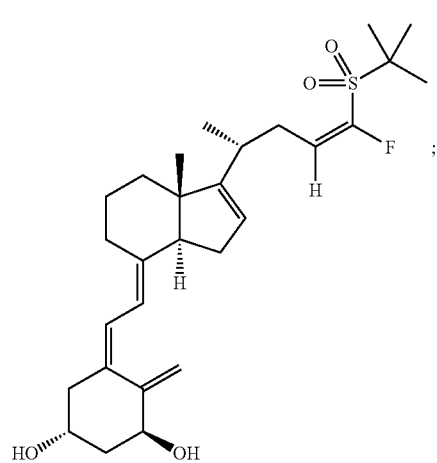 Ib(v)
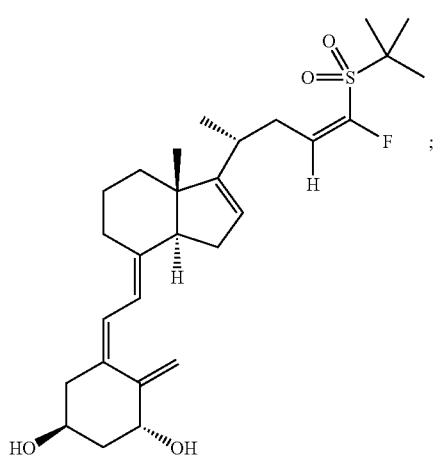 Ib(vi)
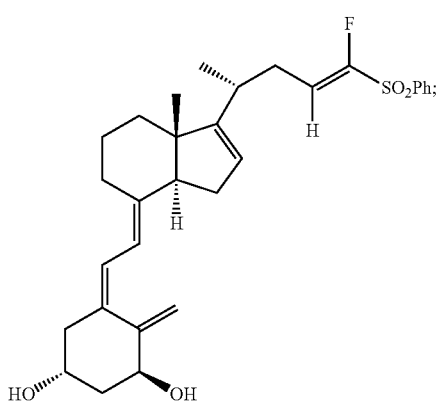 Ia(vii)
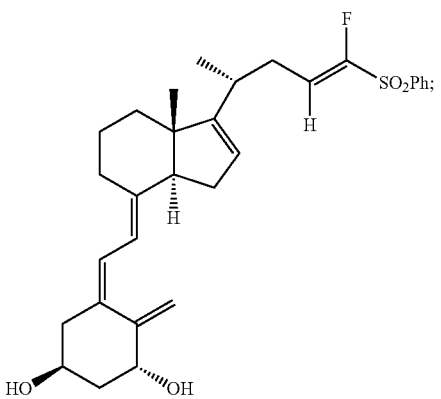 Ia(viii)
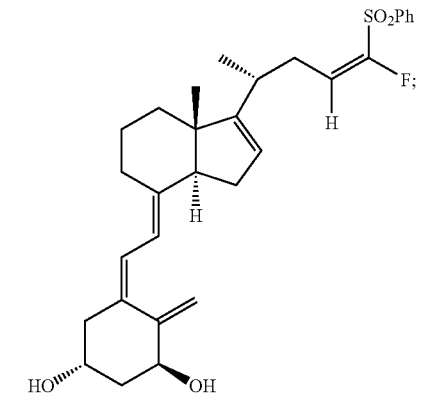 Ib(vii)
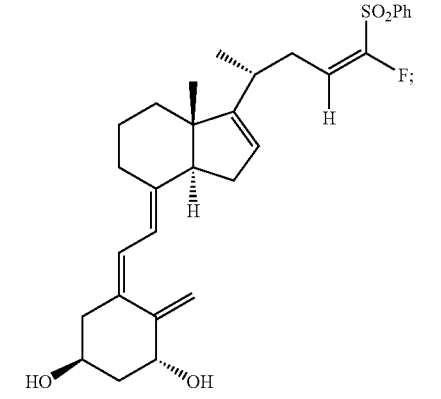 Ib(viii)

-continued
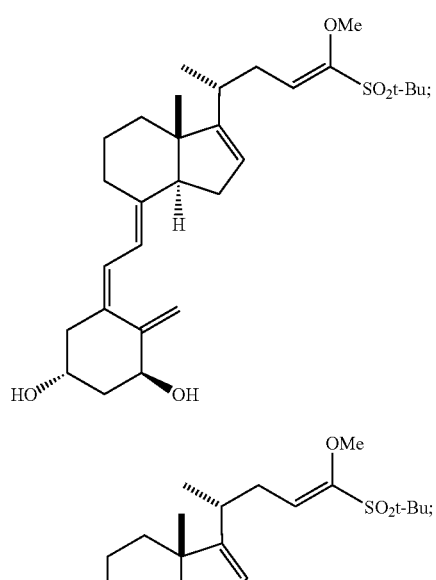
Ia(ix)
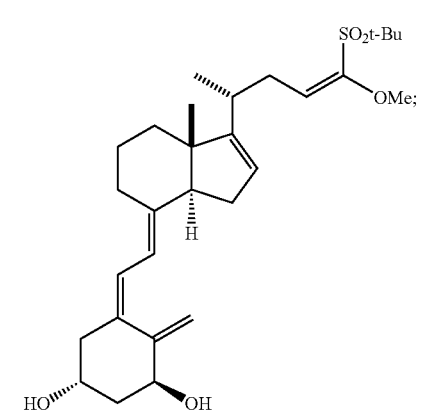
Ia(x)
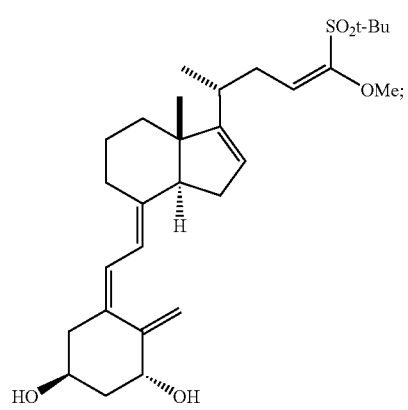
Ib(ix)
Ib(x)
-continued
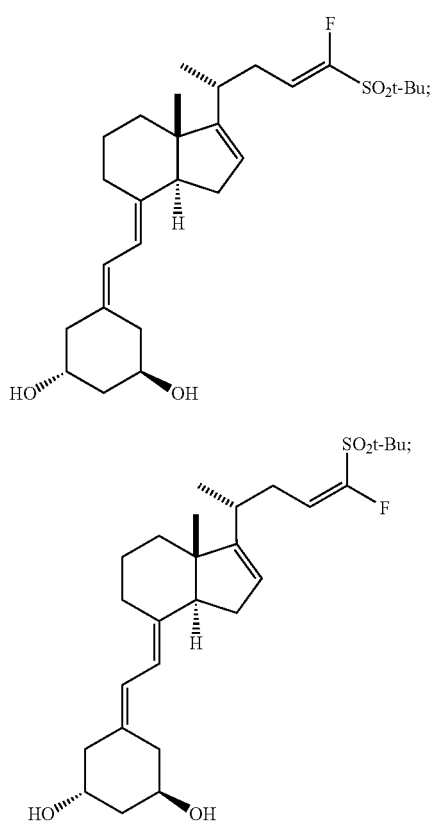
Ia(xi)
Ib(xi)
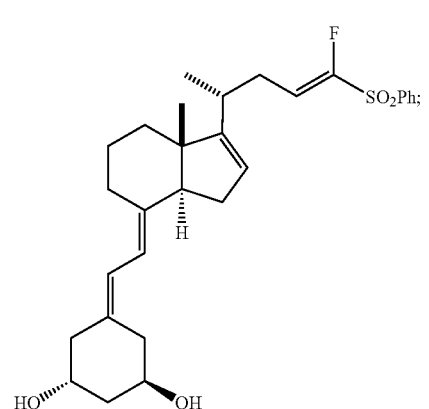
Ia(xii)
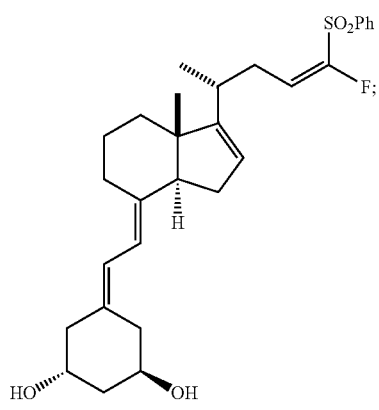
Ib(xii)

Ia(xiii)
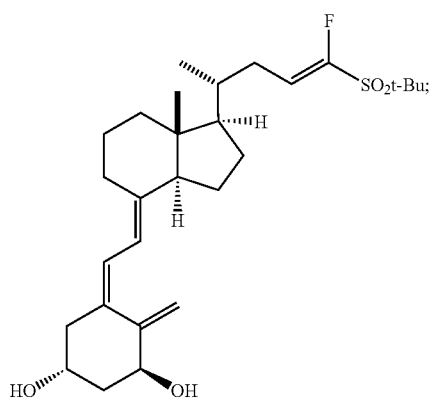
Ib(xiii)
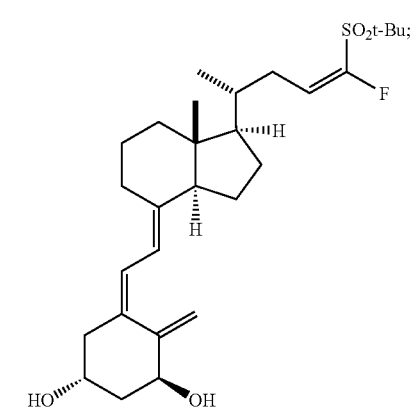
Ia(xiv)
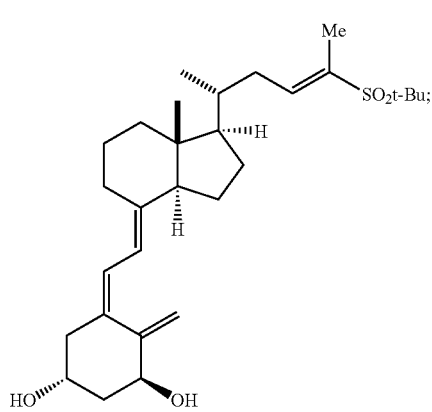
Ia(xv)
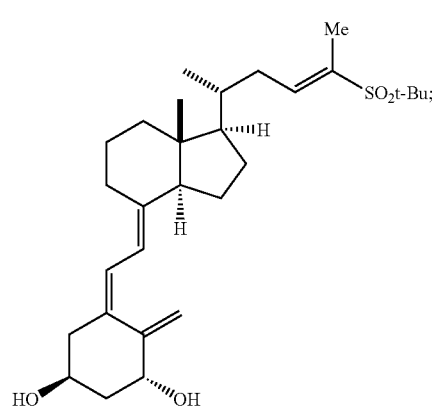
IIa
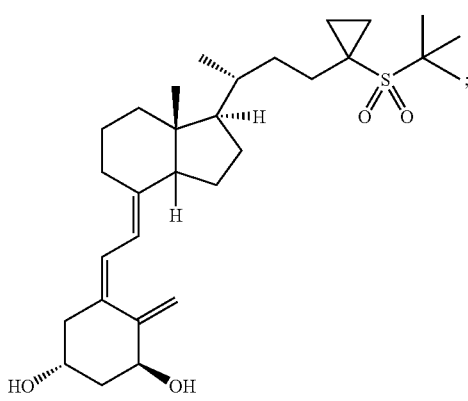
IIb
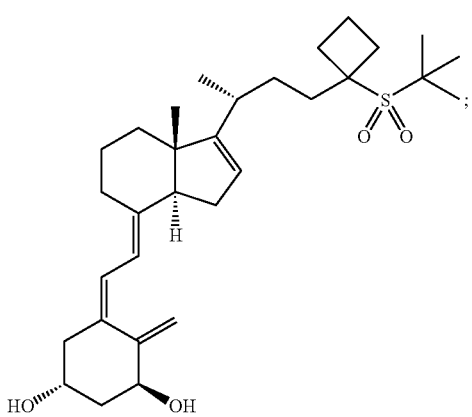
IIc
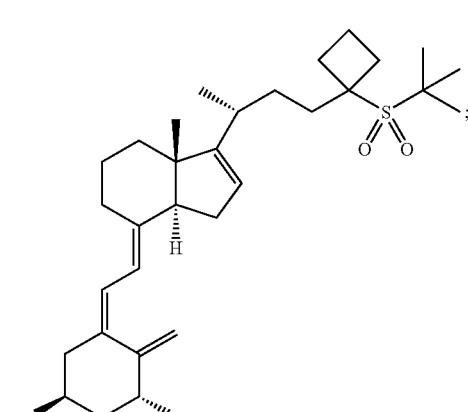
IVa
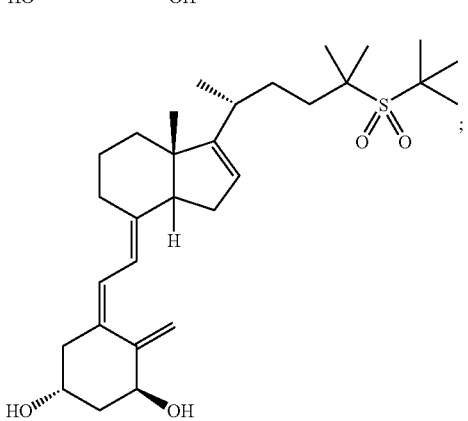

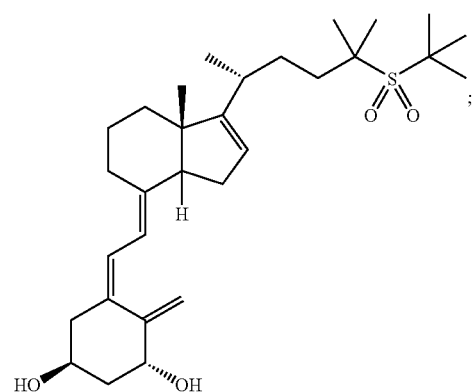

IVb

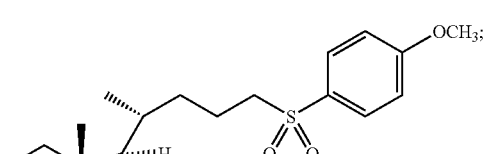

Vc

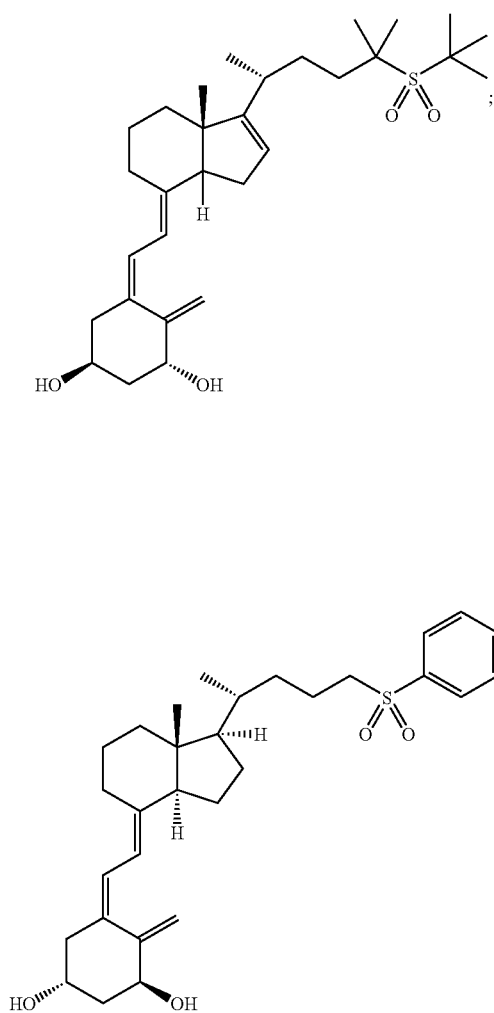

Va, Vb

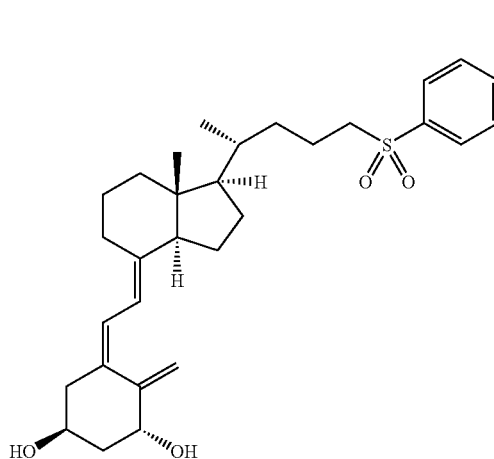

Vd and pharmaceutically acceptable solvates and prodrugs thereof. In embodiments of the present invention, the compounds of the invention are selected from one or more of compound Ia(i), Ia(iii), Ib(i), Ib(v), Ia(vii), Ib(viii), Ia(ix), Ib(ix), Ia(xi), Ib(xi), Ia(xii), Ib(xii), Ia(xiii), Ib(xiii), Ia(xiv), Ia(xv), Ia, IIc, IVa, Va and Vc as shown above and pharmaceutically acceptable solvates and prodrugs thereof. In further embodiments of the invention, the compounds of the invention are selected from one or more of Ia(i), Ib(v), Ib(viii), Ib(ix), Ia(xi), Ia(xiv), IIb, IVa, Va and Vc as shown above and pharmaceutically acceptable solvates and prodrugs thereof.

The present invention includes within its scope, prodrugs of the compounds of the invention. In general, such prodrugs will be functional derivatives of a compound of the invention which are readily convertible in vivo into the compound from which it is notionally derived.

The present invention includes radiolabeled forms of compounds of the invention, for example, compounds of the invention labeled by incorporation within the structure $^3H$ or $^{14}C$ or a radioactive halogen such as $^{125}I$.

III. Methods of Preparing Compounds of the Invention

In accordance with another aspect of the present invention, the compounds of the invention can be prepared by processes analogous to those established in the art. Therefore, compounds of the invention may be prepared, for example, by the reaction sequence shown in Scheme 1:

Scheme 1

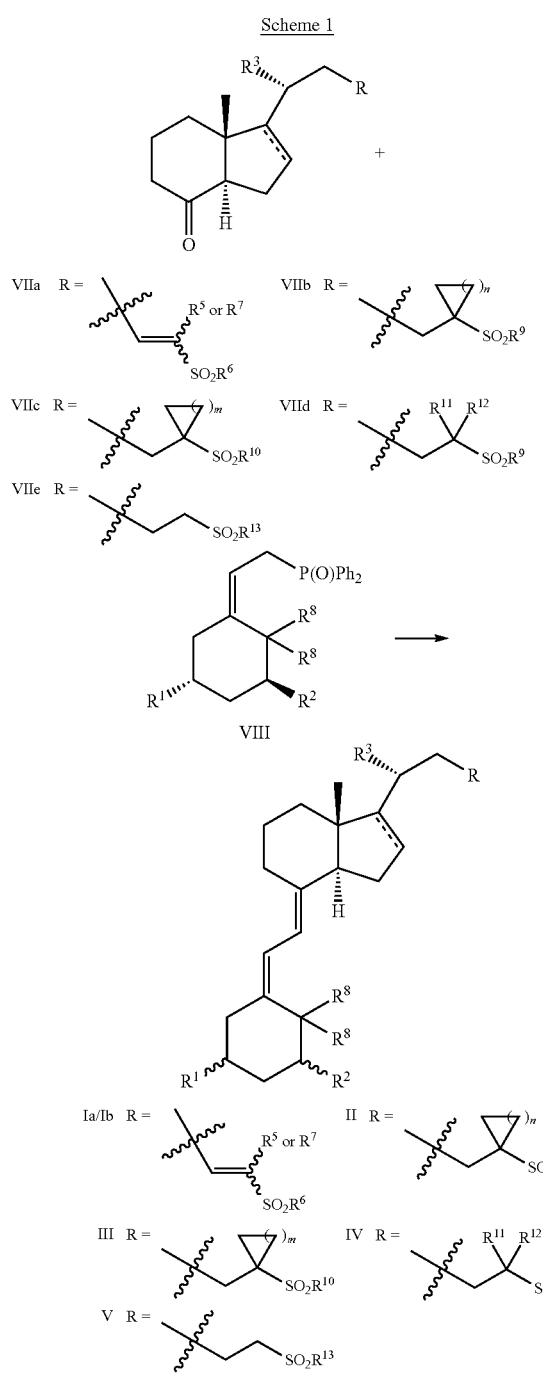

Ketones of Formulae VIIa-VIIe, wherein $R^3$ is as defined in Formulae I-V, ==== represents a single or double bond (as appropriate), $R^5$-$R^7$ are as defined in Formulae Ia and Ib, $R^9$ is as defined in Formulae II and IV, n is as defined in Formula II, $R^{10}$ and m are as defined in Formula III, $R^{11}$ and $R^{12}$ are as defined in Formula IV and $R^{13}$ is as defined in Formula V, may be reacted with phosphine oxides of Formula VIII, wherein $R^1$, $R^2$ and $R^9$ are as defined in Formulae I-V, under standard Homer-Wadsworth-Emmons (HWE) coupling conditions. Therefore azeotropically dried phosphine oxides VIII are treated with a strong base, for example an alkyl lithium such as n-butyl lithium, under anhydrous conditions in an inert atmosphere and solvent, for example tetrahydrofuran (THF), at temperatures in the range of about –60° C. to about –90° C., suitably at about –78° C. To the resulting intermediate phosphine oxide anion is added a cold, suitably at about –78° C., solution of one of azeotropically dried ketones VIIa-e in an inert solvent such as THF while maintaining the anhydrous conditions. After removal of any protecting groups using standard chemistries (if needed), compounds of Formulae Ia, Ib, II, III, IV and V may be obtained, typically as a mixture of the 1α,3β and 1β,3α diasteromers, with the 1α, 3β diastereomer as the major product. These diasteromers may be separated using chromatography, for example using high performance liquid chromatography (HPLC).

The preparation of compounds of Formula VIII, wherein $R^1$, $R^2$ and $R^8$ are as defined in Formulae I-V is known in the art. Therefore compounds of Formula IV may be prepared, for example, as described in Posner, G. H. et al. *J. Med. Chem.* 1992, 35, 3280-3287, the contents of which are incorporated herein by reference.

Ketones of Formulae VIIa-e, wherein $R^3$ is as defined in Formulae I-V, ==== represents a single or double bond (as appropriate), $R^5$-$R^7$ are as defined in Formulae Ia and Ib, $R^9$ is as defined in Formulae II and IV, n is as defined in Formula II, $R^{10}$ and m are as defined in Formula III, $R^{11}$ and $R^{12}$ are as defined in Formula IV and $R^{13}$ is as defined in Formula V, may be prepared, for example, as shown in Scheme 2:

Scheme 2

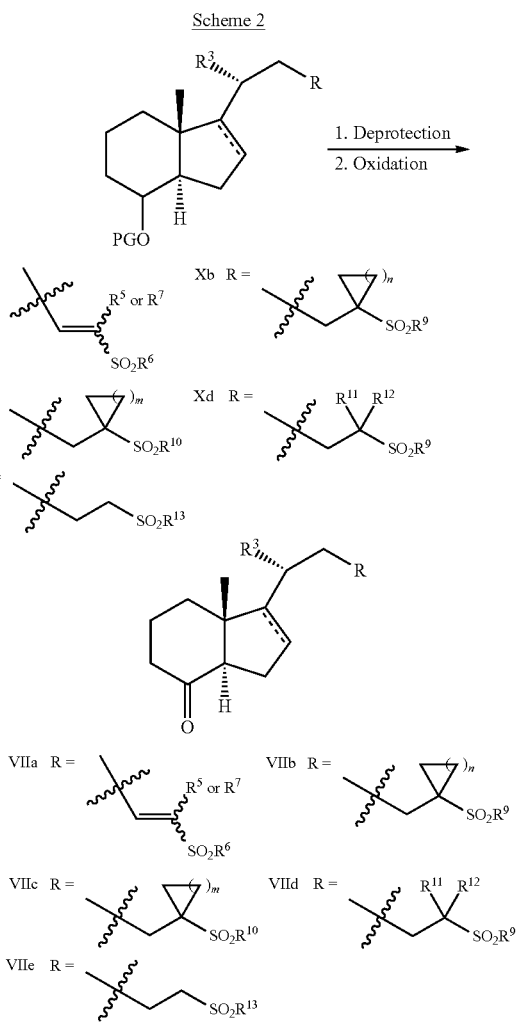

Suitably protected compounds of Formulae Xa-e, wherein $R^3$ is as defined in Formulae I-V, ---- represents a single or double bond (as appropriate), $R^5$-$R^7$ are as defined in Formulae Ia and Ib, $R^9$ is as defined in Formulae II and IV, n is as defined in Formula II, $R^{10}$ and m are as defined in Formula III, $R^{11}$ and $R^{12}$ are as defined in Formula IV, $R^{13}$ is as defined in Formula V and PG is a suitable protecting group, are first deprotected and then oxidized to provide ketones VIIa-e. For example, when PG is trialkyl silyl, such as triethyl silyl, deprotection may be affected by reacting compounds of Formula Xa-e with hydrofluoric acid in an alcoholic solvent such as ethanol, and in an inert atmosphere, suitably at about room temperature. Oxidation of the resulting alcohol may be performed, for example, using pyridinium dichromate (PDC), or any other suitable oxidizing agent, in an inert solvent such as methylene chloride, under standard conditions.

Compounds of Formula Xa, wherein $R^3$ and $R^5$-$R^7$ are as defined in Formulae Ia and Ib, ---- represents a single or a double bond and PG is a suitable protecting group, may be obtained, for example, as shown in Scheme 3:

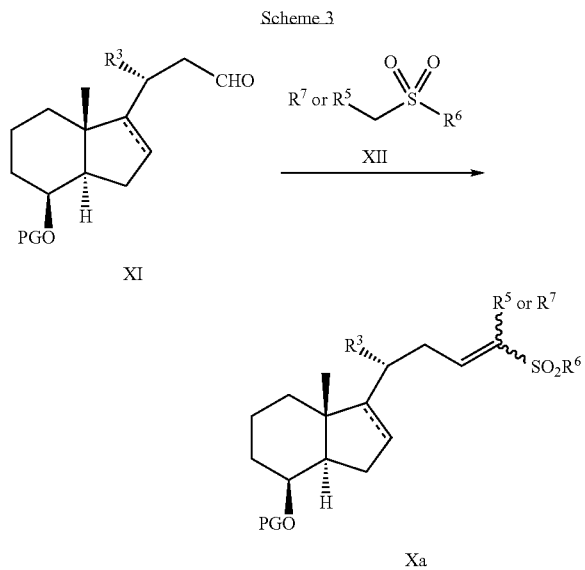

Compounds of Formula XI, wherein $R^3$ and ---- are as defined in Formulae I-V and PG is a suitable protecting group may be reacted with the anion of compounds of Formula XII, wherein $R^6$ and $R^5$ (or $R^7$) are as defined in Formulae Ia and Ib, under anhydrous conditions at temperatures in the range of about −60° C. to about −90° C., suitably at about −78° C. The anions of Formula XII may be prepared by treating compounds of Formula XII with a strong base, for example an alkyl lithium such as lithium diisopropylamine (LDA), under inert conditions and, in the presence of, for example, diethylchlorophosphate.

Compounds of Formula XII, wherein $R^6$ and $R^5$ (or $R^7$) are as defined in Formulae Ia and Ib may be prepared, for example, by the reaction of formaldehyde with a thiol of the Formula XIII, wherein $R^6$ is as defined in Formula Ia and Ib, in the presence of, for example, TMS-$R^5$ or TMS-$R^7$, wherein $R^5$ and $R^7$ are as defined in Formulae Ia and Ib (preferably when $R^5$ and $R^7$ are Cl), to form the corresponding sulfide XIV which is then oxidized to the corresponding sulfone XII as shown in Scheme 4. Alternatively, compounds of Formula XIII, wherein $R^6$ is as defined in Formula Ia and Ib, may be reacted with a reagent of the Formula LGCH$_2$—$R^5$ (or LGCH$_2$—$R^7$), wherein LG is any suitable leaving group such as halogen and $R^5$ and $R^7$ are as defined in Formulae Ia and Ib (preferably when $R^5$ and $R^7$ are other than Cl or F), in the presence of a strong base, such as sodium hydride, in an inert solvent at reduced temperatures, for e.g. 0° C., to form the corresponding sulfide XIV which is then oxidized to the corresponding sulfone XII as shown in Scheme 4.

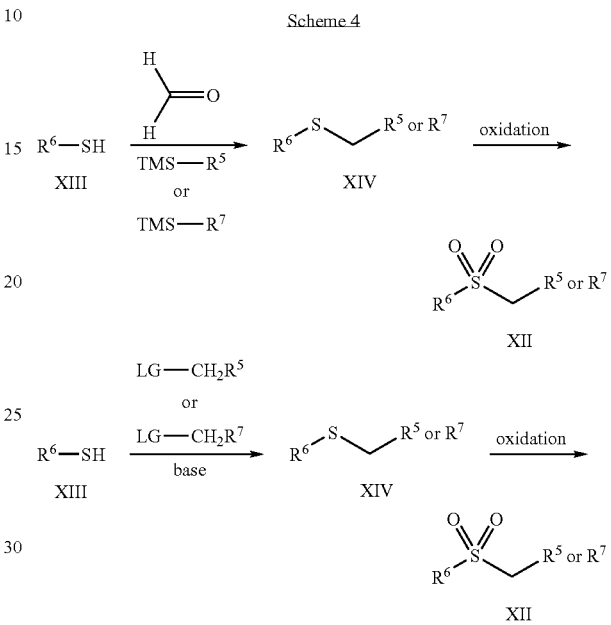

Examples of oxidizing agents include hydrogen peroxide, m-chloroperbenzoic acid and Oxone®, with hydrogen peroxide being preferred. In the case where $R^7$ is F, compounds of Formula XII, wherein $R^6$ is as defined in Formula Ib, may be prepared, for example, by the oxidation of sulfide XV to the corresponding sulfone XVI, which is then treated with base and is reacted with N-fluorobenzenesulfonimide (NFSI) as shown in Scheme 5:

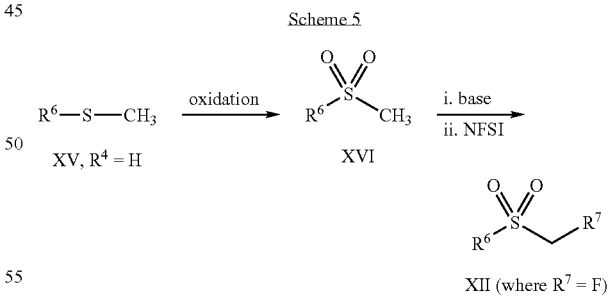

The preparation of compounds of Formula XI, wherein $R^3$ is as defined in Formulae I-V, ---- is a double bond and PG is a suitable protecting group, is known in the art. Therefore compounds of Formula XI may be prepared, for example, as described in Posner, G. H. et al. *J. Med. Chem.* 1998, 41, 3008-3014, the contents of which are incorporated herein by reference. Compounds of Formula XI, wherein $R^3$ is as defined in Formulae I-V, ---- is a single bond and PG is a suitable protecting group, may be prepared for example, by reduction, for example hydride reduction, of the corresponding cyano compound, which in turn is available from the corresponding iodo compound by reaction with, for example KCN (as described in Example 12(a) and 12(b) hereinbelow).

Compounds of Formula Xb, wherein $R^9$ and m are as defined in Formula II, PG is a suitable protecting group and ==== is a double bond; compounds of Formula Xc, wherein $R^{10}$ and m are as defined in Formula III, PG is a suitable protecting group and ==== is a double bond; compounds of Formula Xd, wherein $R^9$, $R^{11}$ and $R^{12}$ are as defined in Formula IV, PG is a suitable protecting group and ==== is a double bond; and compounds of Formula Xe, wherein $R^{13}$ is as defined in Formula V, PG is a suitable protecting group and ==== is a single bond, may all be prepared as shown in Scheme 6:

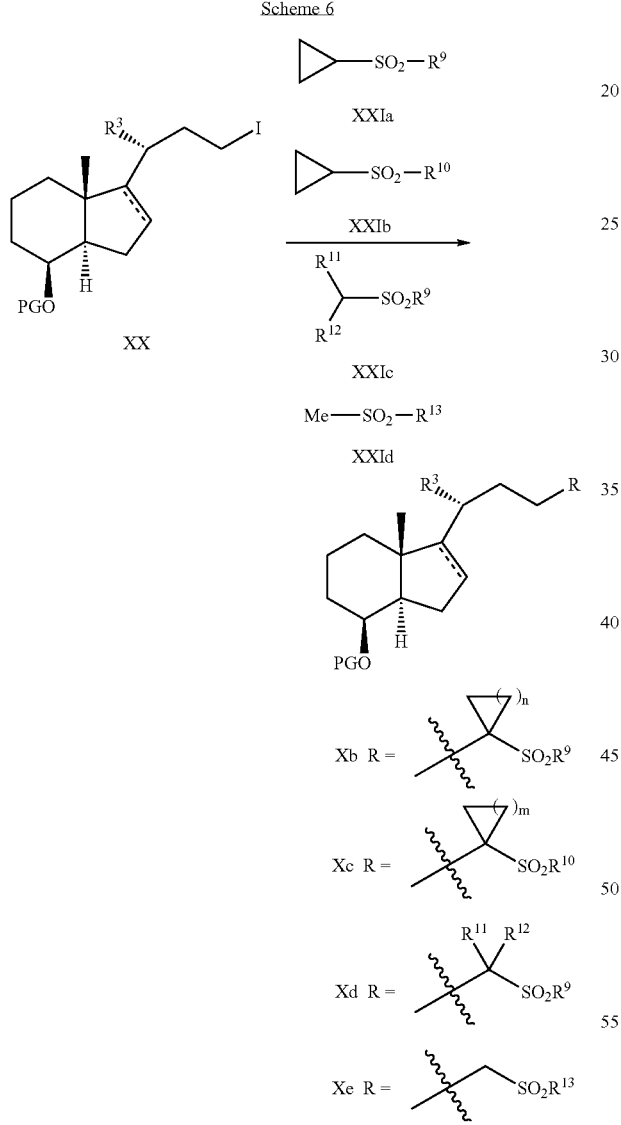

Compounds of Formula XX, wherein $R^3$ is as defined in any one of the Formulae II-V, ==== is a single or double bond (as appropriate) and PG is a suitable protecting group, may be reacted with the anion of compounds of Formula XXIa-d, wherein $R^9$ is as defined in Formulae II and IV, m is as defined in Formula II, $R^{10}$ and m are as defined in Formula III, $R^{11}$ and $R^{12}$ are as defined in Formula IV and $R^{13}$ is as defined in Formula V, under anhydrous conditions at temperatures in the range of about −60° C. to about −90° C., suitably at about −78° C. The anions of compounds of Formula XXIa-d may be prepared by treating compounds of Formula XXIa-d with a strong base, for example an alkyl lithium such as n-butyl-lithium in anhydrous tetrahydrofuran (THF) under inert conditions and, in the presence of, for example, hexamethyl phosphoramide (HMPA) or N,N,N',N'-tetramethy ethylene-diamine (TMEDA).

Compounds of Formula XXIa-d, wherein $R^9$ is as defined in Formulae II and IV, m is as defined in Formula II, $R^{10}$ and m are as defined in Formula III, $R^{11}$ and $R^{12}$ are as defined in Formula IV and $R^{13}$ is as defined in Formula V, are either commercially available, or may be prepared, for example, by the reaction of a thiol XXIIa-c with a reagent of the Formula XXIIIa-d, wherein X is a suitable leaving group such as halogen, in the presence of base, such as sodium methoxide, followed by oxidation to provide the corresponding sulfones XXIa-d as shown in Scheme 7.

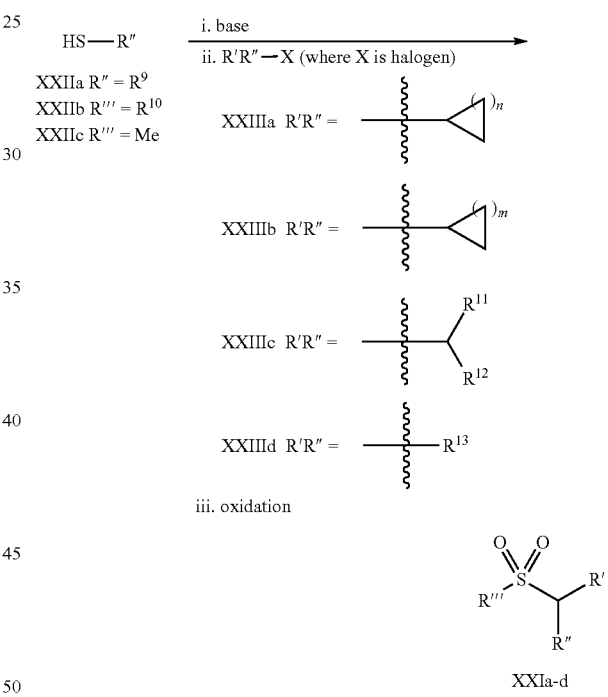

Examples of oxidizing agents include m-chloroperbenzoic acid and Oxone®, with Oxone® being preferred.

The preparation of compounds of Formula XX, wherein $R^3$ is as defined in any one of the Formulae II-V, ==== is a single or a double bond and PG is a suitable protecting group, is known in the art. For example, compounds of Formula XX may be prepared, for example, as described in Posner, G. H. et al. *J. Med. Chem.* 1992, 42, 3425-3435, the contents of which are incorporated herein by reference.

Compounds of Formula Xa are also available by the reaction of compounds of Formula XI under standard Wittig or HWE coupling conditions with, for example a phosphorane of the Formula XXIV, wherein $R^5$-$R^7$ are as defined in Formulae Ia and Ib as shown in Scheme 8.

Scheme 8

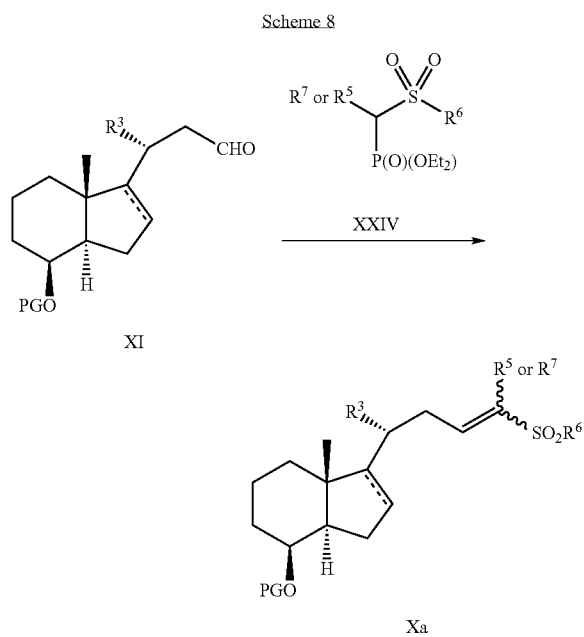

In some cases the chemistries outlined above may have to be modified, for instance by use of protective groups, to prevent side reactions due to reactive groups, such as reactive groups attached as substituents. This may be achieved by means of conventional protecting groups, for example as described in "Protective Groups in Organic Chemistry" McOmie, J. F. W. Ed., Plenum Press, 1973 and in Greene, T. W. and Wuts, P. G. M., "Protective Groups in Organic Synthesis", John Wiley & Sons, 1991.

The formation of a desired compound salt is achieved using standard techniques. For example, the neutral compound is treated with an acid or base in a suitable solvent and the formed salt is isolated by filtration, extraction or any other suitable method.

The formation of solvates of the compounds of the invention will vary depending on the compound and the solvate. In general, solvates are formed by dissolving the compound in the appropriate solvent and isolating the solvate by cooling or using an antisolvent. The solvate is typically dried or azeotroped under ambient conditions.

Prodrugs of the compounds of the invention may be conventional esters formed with available hydroxy, thiol, amino or carboxyl group. For example, when $R^1$ and/or $R^2$ is OH and/or $R^6$, $R^{10}$, $R^{10}$ and/or $R^{14}$ are substituted with one or more OH or $NH_2$ in a compound of the invention, it may be acylated using an activated acid in the presence of a base, and optionally, in inert solvent (e.g. an acid chloride in pyridine). Some common esters which have been utilized as prodrugs are phenyl esters, aliphatic ($C_8$-$C_{24}$) esters, acyloxymethyl esters, carbamates and amino acid esters. In further embodiments, the prodrugs of the compounds of the invention are those in which one or more of the hydroxy groups in the compounds is masked as groups which can be converted to hydroxy groups in vivo. Conventional procedures for the selection and preparation of suitable prodrugs are described, for example, in "Design of Prodrugs" ed. H. Bundgaard, Elsevier, 1985.

A radiolabeled compound of the invention may be prepared using standard methods known in the art. For example, tritium may be incorporated into a compound of the invention using standard techniques, for example by hydrogenation of a suitable precursor to a compound of the invention using tritium gas and a catalyst. Alternatively, a compound of the invention containing radioactive iodo may be prepared from the corresponding trialkyltin (suitably trimethyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halo, suitably iodo, compound using standard palladium-catalyzed stannylation conditions, for example hexamethylditin in the presence of tetrakis(triphenylphosphine) palladium (0) in an inert solvent, such as dioxane, and at elevated temperatures, suitably 50-100 C.

IV. Uses

As hereinbefore mentioned, novel compounds of the Formulae Ia, Ib, II, III, IV and V have been prepared. Accordingly, the present invention includes all uses of the compounds of the invention including their use in therapeutic methods and compositions for modulating cell proliferation, their use in diagnostic assays and their use as research tools.

Selectively inhibiting the cytochrome P450 enzymatic pathway, through which 1α,25-dihydroxyvitamin $D_3$ is catabolized (mainly via C-24 hydroxylation), is one important way to prolong the lifetime of this hormone, or analogs thereof. Therefore, the compounds of Formula I were tested in vitro, using a standard protocol, for their ability to inhibit specifically CYP24, an enzyme responsible for 24-hydroxylation of 1α,25-dihydroxyvitamin $D_3$. Antimycotic ketoconazole, a drug used clinically for chemotherapy of human prostate cancer (Trachtenberg, J. et al. J. Urol. 1984, J32, 61-63), was used as a control standard for inhibition of CYP24. Certain compounds of the invention have been shown to selectively inhibit the CYP24. By "selectively inhibit" it is meant that the compounds show preferential inhibition of the enzyme CYP24, in particular, in comparison to other enzymes in the cytochrome P450 enzymatic pathway, for example, CYP27A1 and CYP27B1. In an embodiment of the invention, the $IC_{50}$ for a compound of the invention for CYP24 is at least about 10-fold less than that for CYP27A1 and/or CYP27B1.

By selectively modulating CYP24, the enzyme that metabolizes 1α,25-dihydroxyvitamin $D_3$, the levels of 1α,25-dihydroxyvitamin $D_3$ (either endogenous or administered as part of a chemotherapeutic regimen), or analogs thereof, are also be modulated. Diseases that benefit from a modulation, in particular an increase, of the levels of 1α,25-dihydroxyvitamin $D_3$ can therefore be treated using a modulator of CYP24. By acting preferentially on CYP24, side effects caused by interaction with other enzymes and receptors are reduced. Accordingly, the present invention provides a method for treating a disease which benefits from a modulation, preferably an increase, of the levels of 1α,25-dihydroxyvitamin $D_3$, or an analog of 1α,25-dihydroxyvitamin $D_3$, comprising administering an effective amount of a compound of the invention to a cell or animal in need thereof. The invention also includes the use of a compound of the invention to treat a disease which benefits from a modulation, preferably an increase, of the levels of 1α,25-dihydroxyvitamin $D_3$, or an analog of 1α,25-dihydroxyvitamin $D_3$. Further, the invention includes a use of a compound of the invention to prepare a medicament to treat a disease which benefits from a modulation, preferably an increase, of the levels of 1α,25-dihydroxyvitamin $D_3$, or an analog of 1α,25-dihydroxyvitamin $D_3$.

Inhibition of CYP24 will inhibit the catabolism of 1α,25-dihydroxyvitamin $D_3$, or its analogs, which is expected to lengthen the biological lifetime of these compounds and thus allow smaller amounts of them to be used for effective disease treatment. Such smaller dosing is expected to avoid, or at least minimize, the hypercalcemic toxicity associated with medicinal use of 1α,25-dihydroxyvitamin $D_3$ and its analogs. Further, by inhibiting the catabolism of 1α,25-dihydroxyvitamin $D_3$, the compounds of the invention will increase the endogenous levels of this hormone, which will have similar beneficial therapeutic effects. Therefore, in an embodiment, the present invention provides a method for treating a disease which benefits from inhibiting the catabolism of 1α,25-dihydroxyvitamin $D_3$, or an analog of 1α,25-dihydroxyvitamin $D_3$, comprising administering an effective amount of a compound of the invention to a cell or animal in need thereof. The invention also includes the use of a compound of the invention to treat a disease which benefits from inhibiting the catabolism of 1α,25-dihydroxyvitamin $D_3$, or an analog of 1α,25-dihydroxyvitamin $D_3$. Further, the invention includes a use of a compound of the invention to prepare a medicament to treat a disease which benefits from inhibiting the catabolism of 1α,25-dihydroxyvitamin $D_3$, or an analog of 1α,25-dihydroxyvitamin $D_3$.

Diseases which will benefit from a modulation in the levels of 1α,25-dihydroxyvitamin $D_3$ include, but are not limited to, one or more of the following:
  i. in the parathyroid—hyper- and hypo-parathyroidism, pseudohypo-parathyroidism, Secondary hyperparathyroidism;
  ii. in the pancreas—diabetes;
  iii. in the thyroid—medullary carcinoma;
  iv. in the skin psoriasis, wound healing;
  v. in the lung—sarcoidosis and tuberculosis;
  vi. in the kidney—chronic renal disease, hypophosphatemic VDRR, vitamin D dependent rickets;
  vii. in the bone—anticonvulsant treatment, fibrogenisis imperfecta ossium, osteitits fibrosa cystica, osteomalacia, osteoporosis, osteopenia, osteosclerosis, renal osteodytrophy, rickets;
  viii. in the intestine—glucocorticoid antagonism, idopathic hypercalcemia, malabsorption syndrome, steatorrhea, tropical sprue; and
  ix. autoimmune disorders.

In embodiments of the invention, the disease that benefits from a modulation in the levels of 1α,25-dihydroxyvitamin $D_3$, or an analog of 1α,25-dihydroxyvitamin $D_3$, is selected from one or more of cancer, dermatological disorders (for example psoriasis), parathyroid disorders (for example hyperparathyroidism and secondary hyperparathyroidism), bone disorders (for example osteoporosis) and autoimmune disorders.

In accordance with a further aspect of the present invention, the disease that benefits from a modulation, in particular an increase, in the levels of 1α,25-dihydroxyvitamin $D_3$, or an analog of 1α,25-dihydroxyvitamin $D_3$, is a cell proliferative disorder. Accordingly, there is provided a method treating a cell proliferative disorder, comprising administering an effective amount of a compound of the invention to a cell or animal in need thereof. The invention also includes a use of a compound of the invention to treat a cell proliferative disorder. The invention further includes a use of a compound of the invention to prepare a medicament to treat a cell proliferative disorder. In an embodiment of the invention, the compounds of the invention are able to treat a cell proliferative disorder by inhibiting cell proliferation and/or promoting cell differentiation.

In particular, the method of the invention is useful in inhibiting the proliferation of abnormal but not normal cells. Abnormal cells include any type of cell that is causative of or involved in a disease or condition and wherein it is desirable to modulate or to inhibit the proliferation of the abnormal cell, or to promote its differentiation, in order to treat the disease or condition. Examples of abnormal cells include malignant or cancerous cells as well as cells that over-proliferate in inflammatory conditions such as psoriasis.

In another embodiment of the present invention, the disease that benefits from a modulation, in particular an increase, in the levels of 1α,25-dihydroxyvitamin $D_3$, or an analog of 1α,25-dihydroxyvitamin $D_3$, is cancer. Accordingly, the present invention provides a method of treating cancer comprising administering an effective amount of a compound of the invention to a cell or animal in need thereof. The invention also includes a use of a compound of the invention to treat cancer. The invention further includes a use of a compound of the invention to prepare a medicament to treat cancer. In embodiments of the invention, the cancer is selected from the group consisting of breast cancer, lung cancer, prostate cancer, colon and colorectal cancer, kidney cancer, head and neck cancer, pancreatic cancer, skin cancer, Kaposi's sarcoma and leukemia.

In another aspect, the invention provides a method of modulating CYP24 activity in a cell by administering an effective amount of a compound of the invention to a cell in need thereof. In a further aspect, the invention provides a method of inhibiting CYP24 activity in a cell by administering an effective amount of a compound of the invention. The present invention also provides a use of a compound of the invention to modulate, preferably to inhibit, CYP24 activity. The present invention further provides a use of a compound of the invention to prepare a medicament to modulate CYP24 activity, preferably to inhibit, CYP24 activity.

The present invention also provides various uses and methods involving known compound of Formula VI:

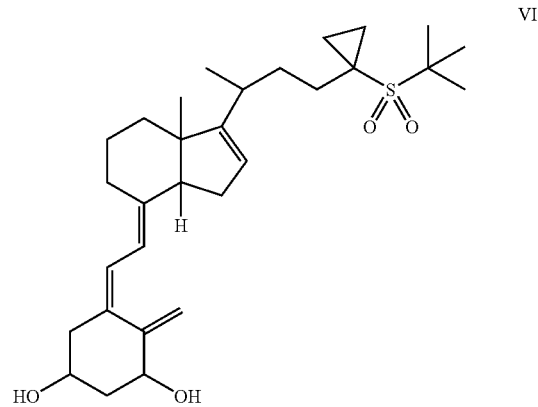

It is to be understood that while the relative stereochemistry of the compound of Formula VI is preferably as shown above, such a compound of Formula VI may also contain certain amounts (e.g. less than 20%, preferably less than 10%, more preferably less than 5%) of a compound of Formula VI having alternate stereochemistry. For example, a compound of Formula VI having the 1α,3β-stereochemistry of natural 1α,25-Dihydroxyvitamin $D_3$, shown above, may contain less then 20%, preferably less then 10%, more preferably less then 5%, of a compound of Formula VI having the unnatural 1β,3α-sterochemistry.

The preparation of the compound of Formula VI was previously reported (Wang, Q. PhD Thesis, 2000, Johns Hopkins University). The ability of the compound of Formula VI to selectively modulate CYP24 activity has not been reported. Further, it was reported that the compound of Formula VI was not antiproliferative (Wang, Q. PhD Thesis, 2000, p. 54, Johns Hopkins University) accordingly a person skilled in the art would not have been motivated by the teaching in Wang to test a compound of Formula VI for modulation of CYP24. In the present invention, it has been shown that the compound of Formula VI shows selective inhibition of CYP24 activity (see Table 1) and that it does have antiproliferative activity. Accordingly, the present invention is the first to find that the compound of Formula VI is useful in the methods of the invention.

In light of the above, the present invention further relates to a method of treating a disease which benefits from modulating CYP24 activity by administering an effective amount of a compound of Formula VI to a cell or animal in need thereof. In a further aspect, the invention provides a method of treating a disease which benefits from inhibiting CYP24 activity by administering an effective amount of a compound of Formula VI to a cell or animal in need thereof. Also provided is a use of a compound of Formula VI to treat a disease which benefits from inhibition of CYP24 activity and to prepare a medicament to treat a disease which benefits from inhibition of CYP24 activity. The present invention also provides a method for treating a disease which benefits from a modulation of the levels of 1α,25-dihydroxyvitamin $D_3$ comprising administering an effective amount of a compound of Formula VI to a cell or animal in need thereof. The invention also includes the use of a compound of Formula VI treat a disease which benefits from a modulation of the levels of 1α,25-dihydroxyvitamin $D_3$. Further, the invention includes a use of a compound of Formula VI to prepare a medicament to treat a disease which benefits from a modulation in the levels of 1α,25-dihydroxyvitamin $D_3$. In a further embodiment, the present invention provides a method for treating a disease which benefits from inhibiting the catabolism of 11α,25-dihydroxyvitamin $D_3$ comprising administering an effective amount of a compound of Formula VI to a cell or animal in need thereof. The invention also includes the use of a compound of Formula VI to treat a disease which benefits from inhibition of the catabolism of 1α,25-dihydroxyvitamin $D_3$. Further, the invention includes a use of a compound of Formula VI to prepare a medicament to treat a disease which benefits from inhibition of the catabolism of 1α,25-dihydroxyvitamin $D_3$. The present invention also provides a method of treating a cell proliferative disorder comprising administering an effective amount of a compound of Formula VI to a cell or animal in need thereof. The invention also includes the use of a compound of Formula VI to treat a cell proliferative disorder and to prepare a medicament to treat a cell proliferative disorder. The invention also provides a method of inhibiting cell proliferation comprising administering an effective amount of a compound of Formula VI to a cell or animal in need thereof. The present invention also includes a use of a compound Formula VI in order to inhibit cell proliferation, preferably cancer cell proliferation. The present invention further includes a use of a compound Formula VI to prepare a medicament to inhibit cell proliferation, preferably cancer cell proliferation.

In embodiments of the invention, the stereochemistry of the compounds of Formula VI is preferably that of natural 1α,25-dihydroxyvitamin $D_3$. Therefore, in a preferred embodiment, the present invention provides uses as described above of a compound of Formula VI with the relative stereochemistry as shown below, and pharmaceutically acceptable solvates and prodrugs thereof:

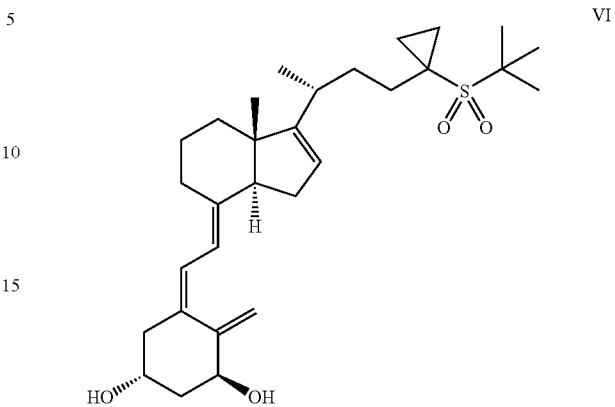

The compounds of the invention and/or a compound of Formula VI can be used alone or in combination with other agents that modulate CYP24 activity, or in combination with other types of treatment (which may or may not modulate CYP24) for diseases that benefit from a modulation, preferably an increase, in the levels of 1α,25-dihydroxyvitamin $D_3$, or analogs thereof, and/or an inhibition of the catabolism of 1α,25-dihydroxyvitamin $D_3$, or an analog thereof. Preferably the compounds of the invention and/or a compound of Formula VI are administered in combination with 1α,25-dihydroxyvitamin $D_3$ (calcitriol), an analog of 1α,25-dihydroxyvitamin $D_3$ or other vitamin D receptor agonists. Inhibiting catabolism of vitamin D receptor agonists such as 1α,25-dihydroxyvitamin $D_3$, or analogs thereof, will lengthen the biological lifetime or efficacy of these therapies and thus allow smaller amounts of the drug to be used for effective human chemotherapy; such smaller dosing will avoid, or at least minimize, the side effects, for example the hypercalcemic toxicity, associated with medicinal use of these compounds. The present invention therefore provides a method of increasing the efficacy of a vitamin D receptor agonist comprising co-administering an effective amount of a compound of the invention and/or a compound of Formula VI, and an effective amount of the vitamin D receptor agonist. Further the invention includes the use of a compound of the invention and/or a compound of Formula VI to increase the efficacy of a vitamin D receptor agonist and a use of a compound of the invention and/or a compound of Formula VI to prepare a medicament to increase the efficacy of a vitamin D receptor agonist. In embodiments of the invention, the vitamin D receptor agonist is 1α,25-dihydroxyvitamin $D_3$, or an analog thereof. By analog of 1α,25-dihydroxyvitamin $D_3$, it is meant a chemically modified analog of 1α,25-dihydroxyvitamin $D_3$ which is a vitamin D receptor agonist and therefore exhibits a therapeutic profile similar to 1α,25-dihydroxyvitamin $D_3$. Examples of such compounds can be found in the following review articles, the contents of which are incorporated herein by reference: Pinette, K. V et al. "Vitamin D Receptor as a Drug Discovery Target", Mini Reviews in Med. Chem. 2003, 3:193-204; Mathieu, C. and Adorini, L. "The Coming of Age of 1,25-Dihydroxyvitamin $D_3$ Analogs as Immunomodulatory Agents", Trends in Mol. Med. 2002, 8:174-179; Carlberg, C. "Molecular Basis of the Selective Activity of Vitamin D Analogues", J. Cell. Bio. 2003, 88:274-281; Stein, M. S. and Wark, J. D. "An update on the therapeutic potential of vitamin D analogues", Expert Opin. Invest. Drugs 2003, 12:825-840; Bouillon, R. et al. "Structure-Function Relationships in the Vitamin D Endocrine System" Endocr. Rev. 1995, 16:200-257; and Nagpal, S. et al. "Vitamin D Analogs: Mechanism of Action and Therapeutic Applications", Current Med. Chem. 2001, 8:1661-1679.

It is to be understood that the compounds of the invention and/or a compound of Formula VI may also work by mechanisms other than CYP24 modulation. For example, the compounds of the invention and a compound of Formula VI, as analogs of $1\alpha,25$-dihydroxyvitamin $D_3$, also possess some of the intrinsic activity of $1\alpha,25$-dihydroxyvitamin $D_3$. For example, the compounds of the present invention have been shown to be able to activate the transcription of the CYP24 gene (see example 28).

Treatments used in combination with the compounds of the present invention and/or a compound of Formula VI may be based on the disease type and do not have to specifically target CYP24 activity or the VDR. In a particular aspect of the present invention, the compounds of the invention and/or a compound of Formula VI are used in combination with other therapies and therapeutics to treat dermatological disorders, bone disorders, cancer and autoimmune disorders. Such therapies include, but are not limited to the following: for cancer: surgery, radiation, chemotherapies and biotherapies; for psoriasis: ultraviolet B radiation, chemotherapy and biotherapies.

One skilled in the art can determine which compounds of the invention would have therapeutic utility, for example, in inhibiting cell proliferation in any type of cancer or cell proliferative disorder. Compounds may be examined for their potency in inhibiting cell growth in cell proliferation assays such as inhibition of growth of murine keratinocyte cells (cell line PE) and for the inhibition of TPA-induced ornithine decarboxylase (ODC) activity as described in U.S. Pat. No. 5,830,885, the contents of which are incorporated herein by reference.

In addition to cancer, the compounds of the invention and/or a compound of Formula VI are useful in treating other conditions involving aberrant or abnormal cell proliferation. Other cell proliferative disorders that may be treated by the present invention include inflammatory diseases, allergies, autoimmune disease, graft rejection, psoriasis, restenosis, artherosclerosis, and any other disorder wherein it is desirable to inhibit, prevent or suppress cell growth. Compounds of the invention and/or a compound of Formula VI may be tested for their potency in a particular cell proliferation disorder using assays and techniques known to those of skill in the art. For example, the following references provide assays for various conditions: Rheumatoid Arthritis: "Regulation of IL-15—Simulated TNF-alpha Production by Rolipram", Journal of Immunology (1999) volume 163 page 8236 by C. S. Kasyapa et al.; Allergy: "A novel Lyn-Binding Peptide Inhibitor Blocks Eosinophil Differentiation, Survival, and Airway eosinophilic inflammation". Journal of Immunology (1999) volume 163 page 939 by T. Adachi et al.; Psoriasis: Journal of Immunology (2000) volume 165 page 224 "Inhibition of Keratinocyte apoptosis by IL-15: a new parameter in the pathegenosis of psoriasis" by R. Üchert; and Psoriasis: International Archives of allergy and Immunology (2000) Volume 123 page 275. "T-cell receptor mimic peptides and their potential application in T-cell mediated disease" by A. H. Erik.

The compounds of the invention and/or a compound of Formula VI are preferably formulated into pharmaceutical compositions for administration to human subjects in a biologically compatible form suitable for administration in vivo. Accordingly, in another aspect, the present invention provides a pharmaceutical composition comprising a compound of the invention and/or a compound of Formula VI in admixture with a suitable diluent or carrier. The present invention further comprises a pharmaceutical composition comprising a compound of the invention and/or a compound of Formula VI and a vitamin D receptor agonist in admixture with a suitable diluent or carrier. In embodiments of the invention, the vitamin D receptor agonist is $1\alpha,25$-dihydroxyvitamin $D_3$, or an analog thereof.

The compositions containing the compounds of the invention and/or a compound of Formula VI can be prepared by known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

The compounds of the invention and/or a compound of Formula VI may be used in the form of the free base, in the form of salts, solvates and/or prodrugs. All forms are within the scope of the invention.

In accordance with the methods of the invention, the described compounds, salts, prodrugs or solvates thereof may be administered to a patient in a variety of forms depending on the selected route of administration, as will be understood by those skilled in the art. The compositions of the invention may be administered, for example, by oral, parenteral, buccal, sublingual, nasal, rectal, patch, pump or transdermal (topical) administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

A compound of the invention and/or a compound of Formula VI thereof may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compound of the invention and/or a compound of Formula VI may be incorporated with excipient and used in the form of ingestible tablets, buccal tablets, troches, capsules, elixirs, suspensions, syrups, wafers, and the like.

A compound of the invention and/or a compound of Formula VI may also be administered parenterally. Solutions of a compound of the invention and/or a compound of Formula VI can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (1990-18th edition) and in The United States Pharmacopeia: The National Formulary (USP 24 NF 19) published in 1999.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists. Ampoules are convenient unit dosages.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Compositions for topical administration may include, for example, propylene glycol, isopropyl alcohol, mineral oil and glycerin. Preparations suitable for topical administration include liquid or semi-liquid preparations such as liniments, lotions, applicants, oil-in-water or water-in-oil emulsions such as creams, ointments or pastes; or solutions or suspensions such as drops. In addition to the aforementioned ingredients, the topical preparations may include one or more additional ingredients such as diluents, buffers, flavouring agents, binders, surface active agents, thickeners, lubricants, preservatives, e.g. methyl hydroxybenzoate (including antioxidants), emulsifying agents and the like.

Sustained or direct release compositions can be formulated, e.g. liposomes or those wherein the active compound is protected with differentially degradable coatings, such as by microencapsulation, multiple coatings, etc. It is also possible to freeze-dry the compounds of the invention and use the lypolizates obtained, for example, for the preparation of products for injection.

The compounds of the invention and/or a compound of Formula VI may be administered to an animal alone or in combination with pharmaceutically acceptable carriers, as noted above, the proportion of which is determined by the solubility and chemical nature of the compound, chosen route of administration and standard pharmaceutical practice.

The dosage of the compounds and/or compositions of the invention and/or a compound of Formula VI can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the animal to be treated. One of skill in the art can determine the appropriate dosage based on the above factors. For example, in the topical treatment, ointments, creams, or lotions containing from 1-1000 µg/g of a compound of the invention may be administered. Oral preparations may be formulated, preferably as tablets, capsules, or drops, containing from 0.5-1000 µg of a compound of the invention and/or a compound of Formula VI, per dosage unit. The compounds of the invention and/or a compound of Formula VI may be administered initially in a suitable dosage that may be adjusted as required, depending on the clinical response. For ex vivo treatment of cells over a short period, for example for 30 minutes to 1 hour or longer, higher doses of compound may be used than for long term in vivo therapy.

In addition to the above-mentioned therapeutic uses, the compounds of the invention and a compound of Formula VI are also useful in diagnostic assays, screening assays and as research tools.

In diagnostic assays the compounds of the invention and/or a compound of Formula VI may be useful in identifying or detecting a cell proliferative disorder. In such an embodiment, the compounds of the invention may be radiolabelled (as hereinbefore described) and contacted with a population of cells. The presence of the radiolabel on the cells may indicate a cell proliferative disorder.

In screening assays, the compounds of the invention and/or a compound of Formula VI may be used to identify other compounds that modulate cell proliferation or CYP24 activity. As research tools, the compounds of the invention and/or a compound of Formula VI may be used in receptor binding assays and assays to study the localization of CYP24. In such assays, the compounds may also be radiolabelled.

The following non-limiting examples are illustrative of the present invention:

EXAMPLES

Materials and Methods

Unless otherwise noted, all reactions were performed in oven-dried glassware stirred under an atmosphere of ultra-high-purity argon. THF was distilled from Na/benzophenone ketyl and $CH_2Cl_2$ distilled from $CaH_2$ immediately prior to use. Organolithiums were titrated prior to use following known methods (Suffert, J. *J. Org. Chem.* 1989, 54, 509-510). All other reagents were used as received from commercial suppliers. Analytical TLC analysis was conducted on pre-coated glass-backed silica gel plates (Merck Kieselgel 60 $F_{254}$, 250 mm thickness) and visualized with p-anisaldehyde or $KMnO_4$ stains. Column chromatography was performed using short path silica gel (particle size<230 mesh) or flash silica gel (particle size 230-400 mesh). Preparative-plate chromatography was performed using silica-gel-coated glass preparative plates (500-1000 µm) from Analtech and analyzed by UV. HPLC was carried out using a Rainin HPLX™ system equipped with two 25-mL/min preparative pump heads using (1) a Chiral Technologies CHIRALCEL® OJ 10-mm×250-mm (semipreparative) column packed with cellulose tris(4-methylbenzoate) on a 10 µm silica-gel substrate or (2) a Phenomenex LUNA™ 10-mm×250-mm (semi-preparative) column packed with 110 Å silica gel (5 µm pore size) as C-18-bonded silica and a Rainin Dynamax™ UV-C dual-beam variable-wavelength detector set at 254 nm. Yields are reported for pure products (>95% based on their chromatographic and spectroscopic homogeneity) and are unoptimized. Melting points were determined in open capillaries using a Mel-Temp metal-block apparatus and are uncorrected. Optical rotations were measured at the Na line using a Perkin-Elmer 141 Polarimeter. NMR spectra were obtained on a Varian XL-400 spectrometer operating at 400 MHz for $^1H$, 376 MHz for $^{19}F$, and 100 MHz for $^{13}C$ and a Bruker 300 AMX spectrometer operating at 300 MHz for $^1H$. Chemical shifts are reported in ppm (δ) and are referenced to $CDCl_3$ (7.26 ppm for $^1H$ and 77.0 ppm for $^{13}C$), tetramethylsilane (TMS, 0.00 ppm for $^1H$), and $CFCl_3$ (0.00 ppm for $^{19}F$). IR spectra were obtained using a Perkin Elmer 1600 Series FT-IR instrument. HRMS were obtained at the mass spectrometry facility at the Ohio State University on a Micromass QTOF Electrospray mass spectrometer. Elemental analyses were performed by Atlantic Microlab Inc., Norcross, Ga.

Examples for Compounds of Formulae Ia and Ib

Example 1

Preparation of tert-butyl chloromethyl sulfone XII(i)

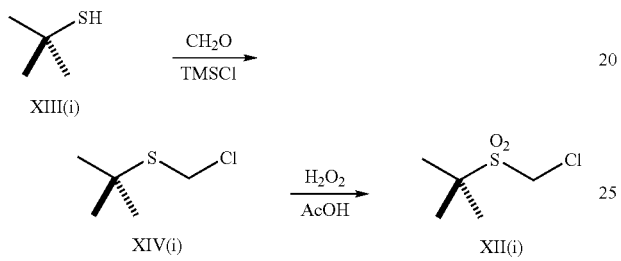

To a suspension of TMSCl (15.9 mL, 125 mmol) and paraformaldehyde (1.5 g, 50 mmol) at room temperature was added tert-butyl thiol XIII(i)(5.64 mL, 50 mmol). The reaction mixture was allowed to stir for 2 hours at which time the crude mixture was dissolved in acetic acid (30 mL). Hydrogen peroxide (25 mL) was added dropwise over the course of 1 h and the reaction mixture was gently heated for 5 minutes. The mixture was extracted with $CH_2Cl_2$ (3×20 mL) and the combined organic layers washed with aqueous sodium bicarbonate, dried over $MgSO_4$ and concentrated. The desired product precipitated from the concentrate upon standing and was purified by recrystalization to afford 4.72 g (55%) of XII(i) as a white solid: $^1H$ NMR (400 MHz, $CDCl_3$) δ 4.55 (s, 2H), 1.52 (s, 9H); $^{13}C$ NMR (100 MHz, $CDCl_3$) d 61.49, 52.52, 21.13; IR (thin film) 3037, 2966, 1467, 1296, 1120, 908, 732 $cm^{-1}$; HRMS [M+Na] calcd 193.0066. Found 193.0068.

Example 2

Preparation of C/D Ring Ketones (+)-Z-VIIa(i) and (iii) and (+)-E-VIIa(ii) and (iv)

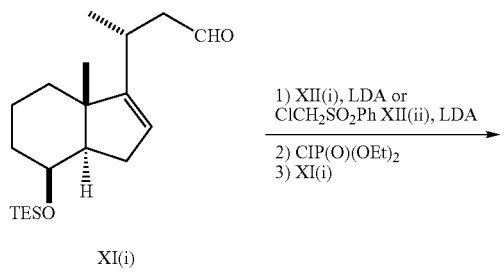

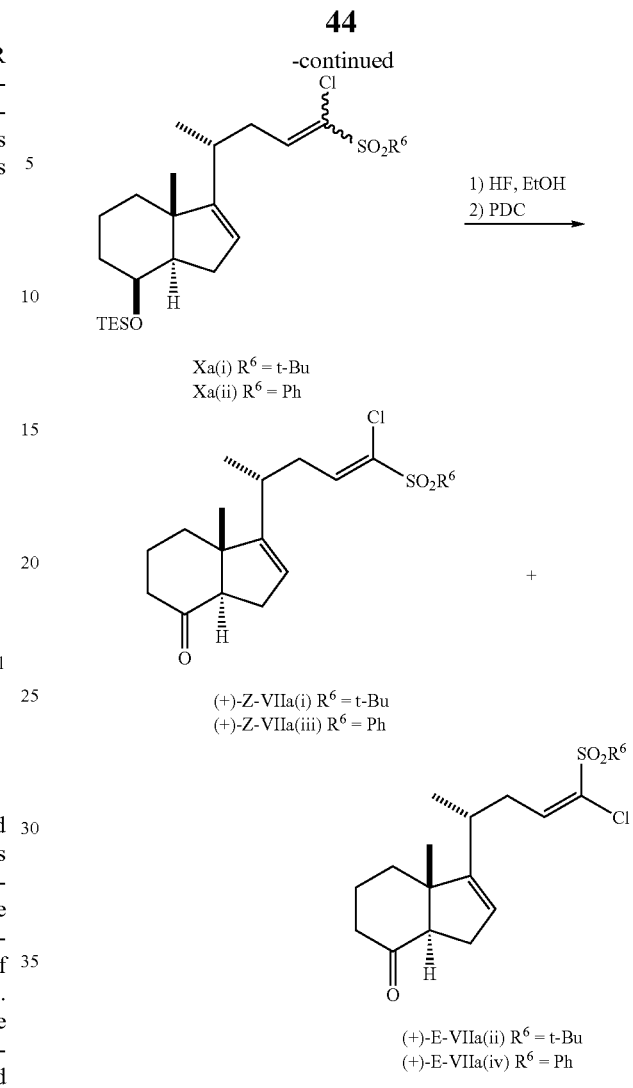

(a) Preparation of Xa(i): A solution of lithium diisopropylamide (0.596 mmol) was generated at −78 C by dropwise addition of n-Butyllithium (1.14 M in hexanes, 523 µL, 0.596 mmol) to diisopropylamine (83.5 µL, 0.596 mmol). A precooled (−78 C) solution of tert-butyl chloromethyl sulfone XII(i) (54.4 mg, 0.319 mmol) was added via cannula as a solution in THF (2 mL) and the reaction mixture stirred at −78 C for 10 minutes. Diethylchlorophosphate (46.1 µL, 0.319 mmol) was added neat and the reaction mixture stirred at −78 C for 1 h. A precooled (−78 C) solution of TES-protected aldehyde XI(i) (71.6 mg, 0.213 mmol) in THF (2 mL) was added via cannula. The reaction mixture was allowed to stir at −78 C for 30 minutes and then warmed to room temperature and allowed to stir overnight. The mixture was quenched with water (5 mL), extracted with $CH_2Cl_2$ (3×10 mL), dried over $MgSO_4$ and concentrated in vacuo. A mixture of geometrical isomers Xa(i) (77.8 mg, 75%, E:Z 1:1) was isolated by column chromatography (2%-4%-10% EtOAc/hexanes) as a clear oil. $^1H$ NMR (400 MHz, $CDCl_3$) δ 6.93 (dd, J=6.8, 7.2), 6.66 (dd, J=6.8, 8.4 Hz, 1H), 5.35 (m, 1H), 5.31 (m, 1H), 4.12 (m, 2H), 2.9-2.2 (m, 8H), 1.97-1.82 (m, 4H), 1.78-1.56 (m, 12H), 1.47 (s, 9H), 1.42 (s, 9H), 1.10-0.92 (m, 12H).

(b) Preparation of C/D Ring Ketones (+)-Z-VII(i) and (+)-E-VII(ii):

To a solution of Xa(i) (75.8 mg, 0.153 mmol) in ethanol (5 mL) was added 49% aq. HF (0.4 mL) dropwise at room temperature. The mixture was stirred for 3 h, quenched with saturated aqueous sodium bicarbonate (10 mL), dried over $MgSO_4$ and concentrated to afford a crude product mixture of alcohols as a clear oil (62 mg). This mixture was dissolved in anhydrous $CH_2Cl_2$ (5 mL) and combined with celite (75 mg) and PDC (124.4 mg, 0.331 mmol). The reaction mixture was stirred overnight at room temperature, passed through a 2 cm pad of flash silica gel and washed with EtOAc. The filtrate was concentrated and purified by column chromatography (70% diethyl ether in hexanes) to provide a mixture of (+)-Z-VII(i) and (+)-E-VII(ii) as a colorless oil. Preparative TLC provided (+)-Z-VII(i) (24.0 mg, 42%, 2 steps) as a clear oil and (+)-E-VII(ii) as a white solid (15.5 mg, 27%, 2 steps).

(+)-Z-VII(i): $[\alpha]_D$ +31.3 (c 2.1, $CHCl_3$); $^1H$ NMR (400 MHz, $CDCl_3$) δ 6.92 (t, J=6.4 Hz, 1H), 5.36 (m, 1H), 2.89-2.84 (m, 1H), 2.66-2.59 (m, 1H) 2.52-2.40 (m, 3H), 2.32-2.27 (m, 2H), 2.18-1.90 (m, 4H), 1.81 (dt, J=12.8, 5.2 Hz, 1H), 1.42 (s, 9H), 1.15 (d, J=6.8 Hz, 3H), 0.82 (s, 3H); $^{13}C$ NMR (100 MHz, $CDCl_3$) d 211.5, 157.3, 145.2, 130.3, 122.9, 63.9, 62.3, 54.7, 41.4, 37.0, 35.4, 32.7, 28.1, 25.1, 24.9, 22.5, 18.3; IR (thin film) 2919, 1719, 1461, 1367, 1278, 1120, 1073 $cm^{-1}$; HRMS [M+Na] calcd 395.1424. Found 395.1404.

(+)-E-VII(ii): $[\alpha]_D$ +15.3 (c 6.1, $CHCl_3$); $^1H$ NMR (400 MHz, $CDCl_3$) δ 6.63 (t, J=7.6 Hz, 1H), 5.40 (m, 1H), 2.89-2.83 (m, 1H), 2.81-2.74 (m, 2H), 2.52-2.44 (m, 1H), 2.35-2.27 (m, 3H), 2.15-2.09 (m, 2H), 2.05-2.01 (m, 1H), 1.95-1.89 (m, 1H), 1.82-1.77 (m, 1H), 1.46 (s, 9H), 1.12 (d, J=6.8 Hz, 3H), 0.83 (s, 3H); $^{13}C$ NMR (100 MHz, $CDCl_3$) d 211.5, 157.3, 147.6, 128.0, 123.2, 64.0, 63.2, 54.7, 41.4, 37.0, 35.2, 33.9, 31.3, 24.9, 24.8, 22.4, 18.3; IR (thin film) 2932, 1720, 1314, 1126, 679 $cm^{-1}$; HRMS [M+Na] calcd 395.1424. Found 395.1424.

(c) Preparation of Xa(ii): A solution of lithium diisopropylamide (0.710 mmol) was generated at −78 C by dropwise addition of n-butyllithium (2.5 M in hexanes, 284 μL, 0.710 mmol) to diisopropylamine (99.5 μL, 0.710 mmol). A precooled (−78 C) solution of chloromethyl phenyl sulfone XII (ii) (72.4 mg, 0.380 mmol) was added via cannula as a solution in THF (2 mL) and the reaction mixture stirred at −78 C for 15 minutes. Diethylchlorophosphate (54.9 μL, 0.380 mmol) was added neat and the reaction mixture stirred at −78 C for 1 h. A precooled (−78 C) solution of TES-protected aldehyde XI(i) (85.3 mg, 0.253 mmol) in THF (2 mL) was added via cannula. The reaction mixture was allowed to stir at −78 C for 30 minutes and then warmed to room temperature and allowed to stir overnight. The mixture was quenched with water (5 mL), extracted with $CH_2Cl_2$ (3×15 mL), dried over $MgSO_4$ and concentrated in vacuo. A mixture of geometrical isomers Xa(ii) (97.0 mg, 75%, E:Z 2:3) was isolated by column chromatography (12% $Et_2O$/hexanes) as a clear oil. $^1H$ NMR (400 MHz, $CDCl_3$) δ 7.98-53 (m, phenyl protons, both isomers), 7.16 (t, J=7.2 Hz, 1.5H, side chain vinyl proton, Z isomer), 6.36 (t, J=7.6 Hz, 1H, side chain vinyl proton, E isomer), 5.34 (m, 1H, D ring vinyl proton, E isomer), 5.26 (m, 1.5H, D ring vinyl proton, Z isomer), 4.12 (m, 2.5H, C8 proton, both isomers).

(d) Preparation of CD-ring ketones (+)-E-VII(iv) and (+)-Z-VII(iii): To a solution of C24-Chloro-C25-sulfones Xa(ii) (81.0 mg, 0.159 mmol) in ethanol (5 mL) was added 49% aq. HF (0.45 mL) dropwise at room temperature. The mixture was stirred for 3 h, quenched with saturated aqueous sodium bicarbonate (5 mL), dried over $MgSO_4$ and concentrated to afford a crude product mixture of alcohols as a clear oil (71.3 mg). This mixture was dissolved in anhydrous $CH_2Cl_2$ (5 mL) and combined with celite (120 mg) and PDC (135.8 mg, 0.361 mmol). The reaction mixture was stirred overnight at room temperature, passed through a 1 cm pad of flash silica gel and washed with EtOAc. The filtrate was concentrated and purified by column chromatography (50% diethyl ether in hexanes) to provide ketones E-VIIa(iv) (17.1 mg, 27%, 2 steps) and Z-VIIa(iii) (26.2 mg, 42%, 2 steps) as colorless oils. A fraction consisting of a 1:2 E:Z mixture of the isomers (15.6 mg, 25%, 2 steps) was also obtained. (+)-Z-VIIa(iii): $[\alpha]_D$ +20.8 (c 1.55, $CHCl_3$); $^1H$ NMR (400 MHz, $CDCl_3$) δ 7.91-7.89 (m, 2H), 7.67 (tt, J=7.6, 1.2 Hz, 1H), 7.59-7.52 (m, 2H), 7.13 (dd, J=7.2, 6.8 Hz, 1H), 5.31 (m, 1H), 2.83 (dd, J=10.4, 6.0 Hz, 1H), 2.55-2.48 (m, 1H) 2.45-2.37 (m, 3H), 2.31-2.29 (m, 2H), 2.15-1.97 (m, 3H), 1.89 (ddd, J=12.8, 4.8, 1.6 Hz, 1H), 1.77 (dt, J=12.8, 5.6 Hz, 1H), 1.12 (d, J=6.8 Hz, 3H), 0.79 (s, 3H); $^{13}C$ NMR (100 MHz, $CDCl_3$) δ 210.4, 156.1, 139.2, 137.3, 134.1, 133.3, 129.1, 128.8, 121.9, 62.8, 53.7, 40.4, 35.4, 34.3, 31.7, 27.1, 23.9, 21.5, 17.4; IR (thin film) 3060, 2942, 2919, 2849, 1713, 1449, 1326, 1155, 1085, 720, 568 $cm^{-1}$; HRMS [M+Na] calcd 415.1105. Found 415.1088. (+)-E-VIIa(iv): $[\alpha]_D$ +17.5 (c 0.85, $CHCl_3$); $^1H$ NMR (400 MHz, $CDCl_3$) δ 7.97-7.95 (m, 2H), 7.69 (tt, J=7.6, 1.6 Hz, 1H), 7.61-7.56 (m, 2H), 6.34 (t, J=7.6 Hz, 1H), 5.40 (m, 1H), 2.96 (t, J=7.6 Hz, 2H) 2.87 (dd, J=10.8, 6.4 Hz, 1H), 2.46 (ddt, J=16.0, 10.8, 1.6 Hz, 1H) 2.39-2.27 (m, 3H), 2.17-1.97 (m, 3H), 1.95-1.90 (m, 1H), 1.79 (dt, J=12.8, 5.2 Hz, 1H), 1.14 (d, J=6.8 Hz, 3H), 0.81 (s, 3H); $^{13}C$ NMR (100 MHz, $CDCl_3$) δ 210.6, 156.2, 142.7, 138.4, 134.2, 130.4, 129.2, 128.5, 122.2, 63.0, 53.7, 40.4, 35.0, 34.2, 33.0, 27.1, 23.9, 21.5, 17.3; IR (thin film) 2943, 2919, 2849, 1713, 1460, 1378, 1326, 1155 $cm^{-1}$; HRMS [M+Na] calcd 415.1105. Found 415.1102.

Example 3

Preparation of Compounds of the Formulae Ia(i), Ia(ii), Ia(iii), Ia(iv), Ib(i) and Ib(ii)

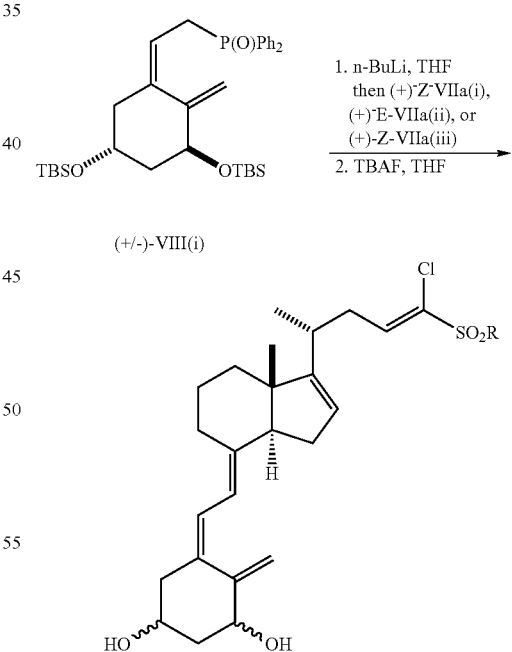

Ia(i) 16-E-23-Z-diene-24-Cl-25-$SO_2$-tBu, [1α,3β]-diol, R = t-Bu
Ia(ii) 16-E-23-Z-diene-24-Cl-25-$SO_2$-tBu, [1β,3α]-diol, R = t-Bu
Ia(iii) 16-E-23-Z-diene-24-Cl-25-$SO_2$-Ph, [1α,3β]-diol, R = Ph
Ia(iv) 16-E-23-Z-diene-24-Cl-25-$SO_2$-Ph, [1β,3α]-diol, R = Ph

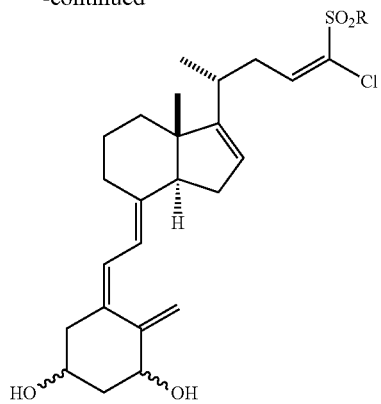

Ib(i) 16-E-23-E-diene-24-Cl-
25-SO₂-tBu, [1α,3β]-diol, R = t-Bu
Ib(ii) 16-E-23-E-diene-24-Cl-
25-SO₂-tBu, [1β,3α]-diol, R = t-Bu (a) Preparation of the compounds of the Formula Ia(i) and Ia(ii): To a solution of azeotropically dried A-ring phosphine oxide VIII(i) (79.9 mg, 0.137 mmol) in THF (2 mL) was added 0.0685 mL of n-BuLi (2.01 M in hexane, 0.137 mmol) at −78° C. The solution was stirred for 10 min at the same temperature. A pre-cooled (−78° C.) solution of azeotropically dried C24-chloro C/D ring ketone (+)-Z-VIIa(i) (22.4 mg, 0.0601 mmol) in THF (2 mL) was added to the above solution at −78° C. via cannula. The resulting solution was stirred for 3.5 hrs at −78° C. The reaction was quenched with 2 mL of pH 7 buffer, then warmed to room temperature, extracted with EtOAc, washed with brine, dried over MgSO₄, filtered, concentrated in vacuo, and purified by flash chromatography (EtOAc:Hexane=1:9 to 1:6 to 1:1) to give 21.0 mg (47%) of a diastereomeric mixture of bis TBS protected Ia(i) and Ia(ii). A solution of the above mixture of bis TBS protected Ia(i) and Ia(ii) (21 mg, 0.0285 mmol) in EtOH (2 mL) was treated with 0.25 mL of 49% aq HF. The crude desilylated mixture was purified by flash chromatography (EtOAc:Hex=1:1 to EtOAc only) to afford quantitatively a diastereomeric mixture of Ia(i) and Ia(ii). The diastereomers were separated by reverse phase HPLC (Phenomenex Luna 5u C18 semipreparative column, 60% MeCN/water, 3 mL/min, 254 nm) to afford 3.1 mg of (+)-Ia(i) (1α,3β, $t_R$ 48.3 min) as a viscous oil and 2.1 mg of (+)-Ia(ii) (1β,3α, $t_R$ 44.2 min) as a viscous oil.

(+)-Ia(i): $R_f$ 0.66 (EtOAc); $[\alpha]_D^{26}$ +13.2 (c 0.33, CHCl₃); ¹H NMR (400 MHz, CDCl₃) δ 6.94 (t, J=6.8, 1H), 6.37 (d, J=10.8 Hz, 1H), 6.10 (d, J=11.2 Hz, 1H), 5.37 (m, 1H), 5.34 (t, J=2.0 Hz, 1H), 5.01 (m, 1H), 4.45 (m, 1H), 4.25 (m, 1H), 2.82 (dd, J=4.8, 12.8 Hz, 1H), 2.57-2.64 (m, 2H), 2.30-2.51 (m, 4H), 2.20 (m, 1H), 1.99-2.08 (m, 2H), 1.91 (m, 1H), 1.73-1.84 (m, 3H), 1.42-1.70 (m, 4H), 1.42 (s, 9H), 1.12 (d, J=6.8 Hz, 3H), 0.70 (s, 3H); ¹³C NMR (100 MHz, CDCl₃) δ 158.0, 147.6, 144.8, 141.8, 133.3, 128.9, 124.8, 122.0, 117.2, 111.7, 70.7, 66.8, 61.2, 58.3, 50.0, 45.2, 42.9, 36.1, 35.3, 31.8, 29.4, 28.7, 24.1, 23.5, 21.4, 17.0; IR (thin film) 3362, 2926, 2849, 1456, 1313, 1122, 1054, 756, 668 cm⁻¹.

(+)-Ia(ii): $R_f$ 0.66 (EtOAc); $[\alpha]_D^{26}$ +2.8 (c 0.21, CHCl₃); ¹H NMR (400 MHz, CDCl₃) δ 6.94 (t, J=6.8 Hz, 1H), 6.38 (d, J=11.2 Hz, 1H), 6.09 (d, J=11.2 Hz, 1H), 5.37 (m, 1H), 5.33 (m, 1H), 5.01 (m, 1H), 4.46 (m, 1H), 4.22 (m, 1H), 2.83 (dd, J=4.4, 12.4 Hz, 1H), 2.57-2.64 (m, 2H), 2.28-2.51 (m, 4H), 2.20 (m, 1H), 2.00-2.05 (m, 2H), 1.94 (m, 1H), 1.77-1.84 (m, 3H), 1.50-1.72 (m, 4H), 1.43 (s, 9H), 1.12 (d, J=6.4 Hz, 3H), 0.70 (s, 3H); ¹³C NMR (100 MHz, CDCl₃) δ 158.0, 147.2, 144.8, 141.9, 133.2, 128.9, 124.8, 122.0, 117.2, 112.8, 71.4, 66.7, 61.3, 58.3, 50.0, 45.5, 42.8, 36.1, 35.3, 31.8, 29.5, 28.7, 24.1, 23.5, 21.4, 17.0; IR (thin film) 3375, 2928, 1454, 1313, 1122, 1054, 754, 668, 570 cm⁻¹.

(b) Preparation of the compounds of the Formula Ia(iii) and Ia(iv): To a solution of A-ring phosphine oxide VIII(i) (36.9 mg, 0.063 mmol) in THF (3 mL) was added 37.2 μL of n-BuLi (1.70 M in Hexane, 0.063 mmol) at −78° C. The reddish solution was stirred for 10 min at the same temperature. A precooled (−78° C.) solution of C24-chloro C/D ring ketone (+)-Z-VIIa(iii) (21.0 mg, 0.053 mmol) in THF (2.5 mL) was added to the above solution at −78° C. via cannula. The resulting reddish orange solution was stirred for 3 hrs at −78° C. The reaction was quenched with 3 mL of pH 7 buffer, then warmed to room temperature, extracted with EtOAc (3×20 mL), dried over MgSO₄, filtered, concentrated in vacuo, and purified by flash chromatography (6% EtOAc in hexanes) to give 11.5 mg (28%) of a diastereomeric mixture of bis TBS protected Ia(iii) and Ia(iv). A solution of the above mixture of bis TBS protected Ia(iii) and Ia(iv) (11.5 mg, 0.015 mmol) in EtOH (2 mL) was treated with 0.3 mL of 49% aq HF. The crude desilylated mixture was purified by flash chromatography (70% EtOAc in hexanes) to afford (7.9 mg, 99%) of a diastereomeric mixture of Ia(iii) and Ia(iv) as a white solid. The diastereomers were separated by reverse phase HPLC (Phenomenex Luna 5u C18 semipreparative column, 55% MeCN/water, 3 mL/min, 254 nm) to afford 5.4 mg of (+)-Ia(iii) (1α,3β, 19%, 2 steps, $t_R$ unknown due to HPLC flow rate variations) as a white solid and 1.4 mg of Ia(iv) (1β,3α, 5%, 2 steps, $t_R$ unknown) as a viscous oil. (+)-Ia(iii): $[\alpha]_D$ +2.6 (c 0.5, CHCl₃); ¹H NMR (400 MHz, CDCl₃) δ 7.92-7.89 (m, 2H), 7.66 (tt, J=7.6, 1.2 Hz, 1H), 7.58-7.53 (m, 2H), 7.15 (t, J=6.8 Hz, 1H), 6.37 (d, J=11.2 Hz, 1H), 6.11 (d, J=11.2 Hz, 1H), 5.37 (m, 1H), 5.34 (m, 1H), 5.03 (m, 1H), 4.46 (m, 1H), 4.26 (m, 1H), 2.82 (dd, J=12.0, 4.0 Hz, 1H), 2.63-2.59 (m, 1H), 2.53-2.47 (m, 1H), 2.43-2.31 (m, 4H), 2.21-2.14 (m, 1H), 2.09-1.97 (m, 2H), 1.94-1.88 (m, 1H), 1.79-1.48 (m, 5H), 1.09 (d, J=6.8 Hz, 3H), 0.68 (s, 3H). ¹³C NMR (100 MHz, CDCl₃) δ 158.0, 147.9, 142.1, 140.0, 137.6, 134.1, 133.5, 133.0, 129.3, 129.0, 124.9, 122.2, 117.3, 111.7, 70.8, 67.0, 58.4, 50.2, 45.3, 43.1, 35.6, 35.4, 32.0, 29.6, 28.8, 23.7, 21.7, 17.2; UV (MeOH) $\lambda_{max}$ 261 nm (ε 14,800); IR (thin film) 3378, 3049, 2931, 2849, 1725, 1619, 1449, 1326, 1155, 1085, 1055, 756 cm⁻¹; HRMS [M+Na] calcd 551.1993. Found 551.2004.

(c) Preparation of the compounds of the Formula Ib(i) and Ib(ii): To a solution of azeotropically dried A-ring phosphine oxide VIII(i) (60.7 mg, 0.104 mmol) in THF (2 mL) was added 0.0465 mL of n-BuLi (2.24 M in hexane, 0.104 mmol) at −78° C. The solution was stirred for 10 min at the same temperature. A pre-cooled (−78° C.) solution of azeotropically dried C24-chloro C/D ring ketone (+)-E-VIIa(ii) (19.2 mg, 0.0515 mmol) in THF (2 mL) was added to the above solution at −78° C. via cannula. The resulting solution was stirred for 3.5 hrs at −78° C. The reaction was quenched with 2 mL of pH 7 buffer, then warmed to room temperature, extracted with EtOAc, washed with brine, dried over MgSO₄, filtered, concentrated in vacuo, and purified by flash chromatography (EtOAc:Hexane=1:9 to 1:6 to 1:1) to give 18.9 mg (50%) of a diastereomeric mixture of bis TBS protected Ib(i) and Ib(ii). A solution of the above mixture of bis TBS protected Ib(i) and Ib(ii) (18.9 mg, 0.0256 mmol) in EtOH (2 mL) was treated with 0.20 mL of 49% aq HF. The crude desilylated mixture was purified by flash chromatography (EtOAc:Hex=1:1 to EtOAc only) to afford quantitatively a diastereomeric mixture of Ib(i) and Ib(ii). The diastereomers were separated by reverse phase HPLC (Phenomenex Luna 5u C18 semipreparative column, 50% MeCN/water, 3 mL/min, 254 nm) to afford 4.4 mg of (−)-Ib(i) (1α,3β $t_R$ 102.4 min) as a viscous oil and 1.5 mg of (−)-Ib(ii) (1β,3α, $t_R$ 94.6 min) as a viscous oil.

(−)-Ib(i): $R_f$ 0.67 (EtOAc); $[\alpha]_D^{26}$ −8.3 (c 0.38, CHCl$_3$); $^1$H NMR (400 MHz, CDCl$_3$) δ 6.64 (t, J=7.6, 1H), 6.37 (d, J=11.6 Hz, 1H), 6.11 (d, J=11.2 Hz, 1H), 5.41 (m, 1H), 5.34 (t, J=1.6 Hz, 1H), 5.02 (m, 1H), 4.44 (m, 1H), 4.24 (m, 1H), 2.72-2.84 (m, 3H), 2.61 (dd, J=3.2, 13.2 Hz, 1H), 2.20-2.41 (m, 4H), 2.00-2.07 (m, 2H), 1.91 (m, 1H), 1.74-1.85 (m, 3H), 1.51-1.71 (m, 4H), 1.46 (s, 9H), 1.09 (d, J=6.8 Hz, 3H), 0.70 (s, 3H); $^{13}$C NMR (100 MHz, CDCl$_3$) δ 157.9, 147.6, 147.2, 142.0, 133.2, 126.4, 124.8, 122.3, 117.1, 111.7, 70.7, 66.9, 62.2, 58.3, 50.0, 45.2, 42.8, 35.9, 35.2, 32.8, 29.5, 28.7, 23.8, 23.5, 21.4, 16.9; IR (thin film) 3370, 2926, 2852, 1454, 1312, 1124, 1054, 756, 678 cm$^{-1}$.

(−)-Ib(ii): $R_f$ 0.67 (EtOAc); $[\alpha]_D^{26}$ −13.5 (c 0.25, CHCl$_3$); $^1$H NMR (400 MHz, CDCl$_3$) δ 6.64 (t, J=7.6, 1H), 6.39 (d, J=11.6 Hz, 1H), 6.10 (d, J=11.2 Hz, 1H), 5.41 (m, 1H), 5.33 (m, 1H), 5.02 (m, 1H), 4.45 (m, 1H), 4.22 (m, 1H), 2.76-2.85 (m, 3H), 2.63 (m, 1H), 2.21-2.40 (m, 4H), 2.01-2.06 (m, 2H), 1.93 (m, 1H), 1.74-1.85 (m, 3H), 1.51-1.70 (m, 4H), 1.46 (s, 9H), 1.09 (d, J=6.8 Hz, 3H), 0.69 (s, 3H); $^{13}$C NMR (100 MHz, CDCl$_3$) δ 157.9, 147.2, 147.1, 142.1, 133.1, 126.4, 124.8, 122.3, 117.1, 112.8, 71.4, 66.8, 62.2, 58.3, 50.0, 45.5, 42.8, 35.9, 35.1, 32.8, 29.5, 28.7, 23.8, 23.5, 21.4, 17.0; IR (thin film) 3368, 2926, 2853, 1454, 1312, 1124, 1053, 678 cm$^{-1}$.

Example 4

Preparation of tert-butyl fluoromethyl sulfone XII(ii)

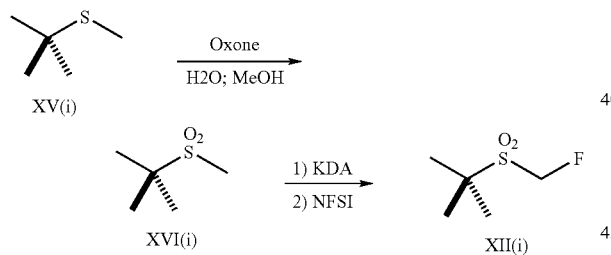

(a) Preparation of tert-Butyl methyl sulfone XVI(i): To a solution of tert-butyl methyl sulfide XV(i) (5.0 g, 0.048 mol) in methanol (125 ml) was added oxone (21.9 g, 0.144 mol) in H$_2$O (125 ml) at 0 C. The mixture was warmed to ambient temperature and allowed to stir overnight. The mixture was concentrated to constant volume, diluted with water (150 mL), extracted with CH$_2$Cl$_2$ (6×50 mL), dried over MgSO$_4$ and concentrated in vacuo to provide sulfone XVI(i) (6.20 g, 95%) as a white solid. $^1$H NMR (400 MHz, CDCl$_3$) δ 2.82 (s, 3H), 1.44 (s, 9H); $^{13}$C NMR (100 MHz, CDCl$_3$) δ 59.62, 35.10, 24.37.

(b) Preparation of tert-Butyl fluoromethyl sulfone XII(ii): A solution of potassium tert-butoxide (700 mg, 6.24 mmol) in THF (7 ml) was cooled to −78 C. Diisopropylamine (875 μL, 6.24 mmol) was added and the mixture was allowed to stir for 15 minutes. n-BuLi (5.01 ml, 1.1 M in hexanes, 5.51 mmol) was added and a color change to orange was observed. tert-Butyl methyl sulfone XVI(i) (500 mg, 3.67 mmol) in THF (5 ml) was added via cannula and the solution was allowed to stir for one hour. A color change to a pale orange was observed. NFSI (1.74 g, 5.51 mmol) in THF (10 ml) was added via cannula and the mixture was allowed to warm to room temperature and stirred for 1.5 hours. The mixture was diluted with water (10 ml mL), extracted with CH$_2$Cl$_2$ (3×15 mL), dried over MgSO$_4$ and concentrated in vacuo. Purification by column chromatography (1:6 EtOAc/hexanes) provided XII (ii) a pale orange oil (312 mg, 55%). $^1$H NMR (400 MHz, CDCl$_3$) δ 5.22 (s, J=47.6 Hz, 2H), 1.48 (d, J=1 Hz, 9H); $^{13}$C NMR (100 MHz, CDCl$_3$) δ 88.78 (d, J=222.1 Hz), 60.91, 24.37 (d, J=1.5 Hz; HRMS [M+Na] calcd 177.0361. Found 177.0366.

Example 5

Preparation of C/D Ring Ketones (+)-E-VIIa(v) and (vii) and (+)-Z-VIIa(vi) and (viii)

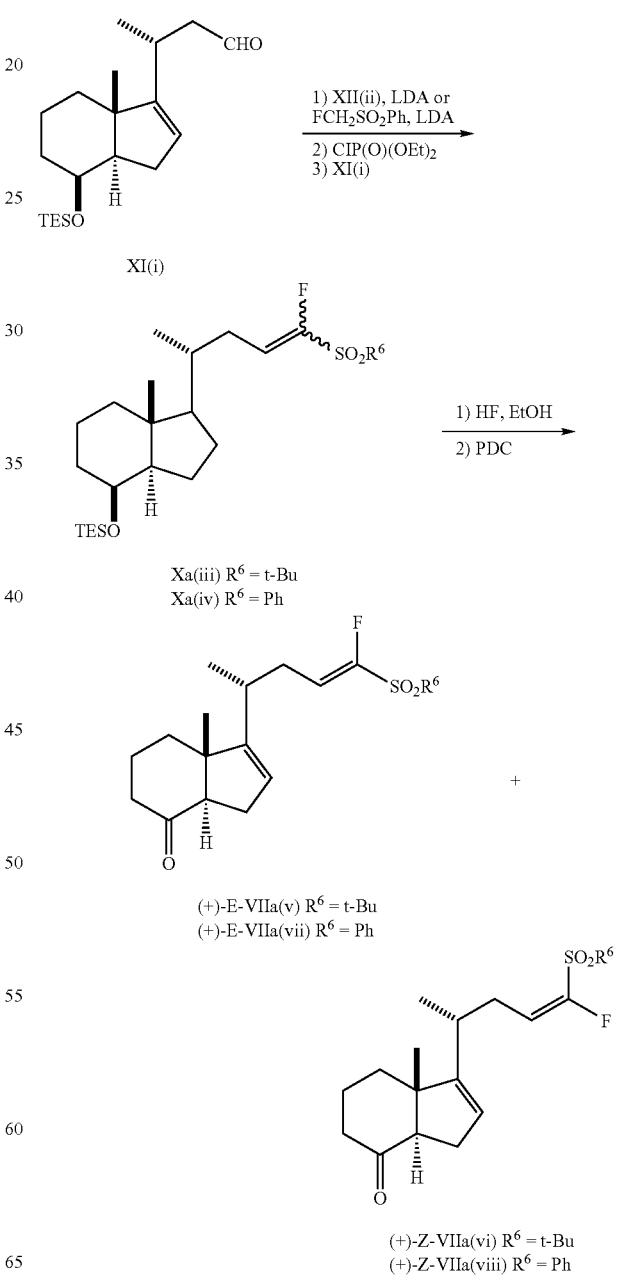

TES-aldehyde XI(i) may be prepared as described in Posner G. H. et al. *J. Med. Chem.* 0.1998, 41, 3008-3014.

(a) Preparation of Xa(iii): A solution of lithium diisopropylamide (0.735 mmol) was generated at −78 C by dropwise addition of n-Butyllithium (1.19 M in hexanes, 618 μL, 0.735 mmol) to diisopropylamine (103 μL, 0.735 mmol). A precooled (−78 C) solution of tert-butyl fluoromethyl sulfone XII(ii) (60.8 mg, 0.394 mmol) was added via cannula as a solution in THF (2 mL) and the reaction mixture stirred at −78 C for 15 minutes. Diethylchlorophosphate (56.9 μL, 0.394 mmol) was added neat and the reaction mixture stirred at −78 C for 1 h. A pre-cooled (−78 C) solution of TES-protected aldehyde XI(i) (88.3 mg, 0.262 mmol) in THF (2 mL) was added via cannula. The reaction mixture was warmed to room temperature and allowed to stir overnight. The mixture was quenched with water (5 mL), extracted with $CH_2Cl_2$ (3×10 mL), dried over $MgSO_4$ and concentrated in vacuo. A mixture of geometrical isomers Xa(iii) (90.8 mg, 73%, E:Z 2:1) was isolated by column chromatography (1%→2% EtOAc/hexanes) as a clear oil.

(b) Preparation of (+)-E-VIIa(v) and (+)-Z-VIIa(vi): To a solution of C24-fluoro-C25-sulfones Xa(iii) (88.0 mg, 0.186 mmol) in ethanol (5 mL) was added 49% aq. HF (0.45 mL) dropwise at room temperature. The mixture was stirred for 3 h, quenched with saturated aqueous sodium bicarbonate (5 mL), dried over $MgSO_4$ and concentrated to afford a crude product mixture of alcohols as a clear oil (68 mg). This mixture was dissolved in anhydrous $CH_2Cl_2$ (5 mL) and combined with celite (75 mg) and PDC (142.7 mg, 0.379 mmol). The reaction mixture was stirred overnight at room temperature, passed through a 1 cm pad of flash silica gel and washed with EtOAc. The filtrate was concentrated and purified by column chromatography (50% diethyl ether in hexanes) to provide ketones (+)-E-VIIa(v) (34 mg after separation, 51%. 2 steps) and (+)-Z-VIIa(vi) (17 mg after separation, 26%, 2 steps) as colorless oils. Several columns were necessary for complete separation.

(+)-E-VIIa(v): $^1$H NMR (400 MHz, $CDCl_3$) δ 6.04 (dt, J=32.8, 7.6 Hz, 1H), 5.36 (t, J=1.6 Hz, 1H), 2.87 (dd, J=10.4, 6.4 Hz, 1H), 2.69-2.64 (m, 1H) 2.56-2.27 (m, 5H), 2.18-1.88 (m, 4H), 1.80 (dt, J=12.8, 5.6 Hz, 1H), 1.39 (d, J=1.2 Hz, 9H), 1.14 (d, J=6.8 Hz, 3H), 0.82 (s, 3H).

(+)-Z-VIIa(vi): $[α]_D$ +30.5 (c 1.2, $CHCl_3$); $^1$H NMR (400 MHz, $CDCl_3$) δ 6.05 (dt, J=23.6, 8.0 Hz, 1H), 5.39 (t, J=1.6 Hz, 1H), 2.86 (dd, J=10.8, 6.8 Hz, 1H), 2.69-2.64 (m, 2H), 2.51-2.43 (m, 1H), 2.32-2.26 (m, 3H), 2.15-2.09 (m, 2H), 2.05-1.96 (m, 1H), 1.96-1.88 (m, 1H), 1.78 (dt, J=12.4, 5.6 Hz, 1H), 1.42 (s, 9H), 1.12 (d, J=6.8 Hz, 3H), 0.82 (s, 3H); $^{13}$C NMR (100 MHz, $CDCl_3$) δ 211.6, 157.3, 150.9 (d, J=289 Hz), 123.7 (d, J=12.9 Hz), 123.0, 64.0, 61.4, 54.7, 41.4, 35.2, 33.9 (d, J=0.5 Hz), 32.0 (d, J=1.5 Hz), 28.1, 24.9, 24.0 (d, J=1.5 Hz), 22.3, 18.3; IR (thin film) 3037, 2919, 2861, 1713, 1455, 1320, 1102, 709 cm$^{-1}$; HRMS [M+Na] calcd 379.1714. Found 379.1743.

(c) Preparation of Xa(iv): A solution of lithium diisopropylamide (0.838 mmol) was generated at −78 C by dropwise addition of n-Butyllithium (1.42 M in hexanes, 590 μL, 0.838 mmol) to diisopropylamine (117.5 μL, 0.838 mmol). A precooled (−78 C) solution of fluoromethyl phenyl sulfone (78.2 mg, 0.449 mmol) was added via cannula as a solution in THF (2.5 mL) and the reaction mixture stirred at −78 C for 15 minutes. Diethylchlorophosphate (64.9 μL, 0.449 mmol) was added neat and the reaction mixture stirred at −78 C for 1 h. A precooled (−78 C) solution of TES-protected aldehyde XI(i) (100.7 mg, 0.299 mmol) in THF (2.5 mL) was added via cannula. The reaction mixture was allowed to stir at −78 C for 15 minutes and then warmed to room temperature and allowed to stir overnight. The mixture was quenched with water (5 mL), extracted with $CH_2Cl_2$ (3×15 mL), dried over $MgSO_4$ and concentrated in vacuo. A mixture of geometrical isomers Xa(iv) (141.7 mg, 96%, E:Z 2:1) was isolated by column chromatography (3% EtOAc/hexanes) as a clear oil. $^1$H NMR (400 MHz, $CDCl_3$) d 7.98-7.55 (m, phenyl protons, both isomers), 6.21 (dt, J=32.8, 7.6 Hz, 2H, side chain vinyl proton, E isomer), 5.82 (dt, J=22.8, 8.0 Hz, 1H, side chain vinyl proton, Z isomer), 5.35 (m, 1H, D ring vinyl proton, Z isomer), 5.25 (m, 2H, D ring vinyl proton, Z isomer), 4.10 (m, 3H, C8 proton, both isomers).

(d) Preparation of (+)-E-VIIa(vii) and (+)-Z-VIIa(viii): To a solution of C24-Fluoro-C25-sulfones Xa(iv) (138.4 mg, 0.281 mmol) in ethanol (5 mL) was added 49% aq. HF (0.70 mL) dropwise at room temperature. The mixture was stirred for 2.5 h, quenched with saturated aqueous sodium bicarbonate (3 mL), dried over $MgSO_4$ and concentrated to afford a crude product mixture of alcohols as a clear oil (110.0 mg). This mixture was dissolved in anhydrous $CH_2Cl_2$ (5 mL) and combined with celite (125 mg) and PDC (218.7 mg, 0.581 mmol). The reaction mixture was stirred overnight at room temperature and then transferred directly to a column. After washing the mixture with $CH_2Cl_2$, the product was purified by column chromatography (45% diethyl ether in hexanes) to provide a mixture of ketones (+)-E-VIIa(vii) and (+)-Z-VIIa (viii) (105.8 mg, 99%, 2 steps) as a colorless oil. $^1$H NMR (400 MHz, $CDCl_3$) d 7.97-7.59 (m, phenyl protons, both isomers), 6.18 (dt, J=32.4, 7.6 Hz, 2H, side chain vinyl proton, E isomer), 5.79 (dt, J=22.4, 8.0 Hz, 1H, side chain vinyl proton, Z isomer), 5.40 (m, 1H, D ring vinyl proton, Z isomer), 5.28 (m, 2H, D ring vinyl proton, Z isomer).

Example 6

Preparation of Compounds of the Formula Ia(v), Ia(vi), Ia(vii) Ia(viii), Ib(v), Ib(vi), Ib(vii) and Ib(viii)

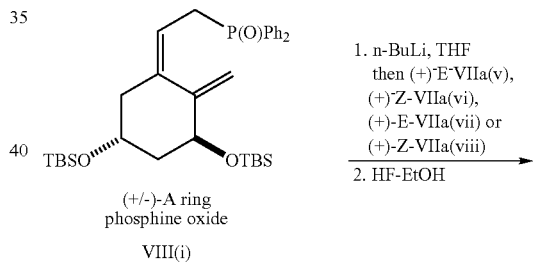

Ia(v). 16-E-,23E-diene-24F-
25-$SO_2$-tBu, [1α,3β]-diol, R = t-Bu
Ia(vi). 16-E-23E-diene-24F-
25-$SO_2$-tBu, [1β,3α]-diol, R = t-Bu
Ia(vii) 16-E-23-E-diene-24-F-
25-$SO_2$-Ph, [1α,3β]-diol, R = Ph
Ia(viii) 16-E-23-E-diene-24-F-
25-$SO_2$-Ph, [1β,3α]-diol, R = Ph -continued

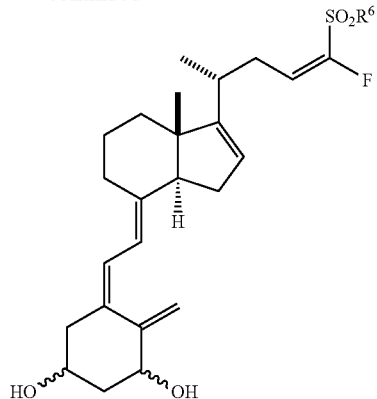

Ib(v). 16-E-23-Z-diene-24F-25-SO$_2$-tBu, [1α,3β]-diol
Ib(vi). 16-E-23-Z-diene-24F-25-SO$_2$-tBu, [1β,3α]-diol
Ib(vii) 16-E-23-Z-diene-24-F-25-SO$_2$-Ph, (1α,3β)-diol
Ib(viii) 16-E-23-Z-diene-24-F-25-SO$_2$-Ph, (1β,3α)-diol (a) Preparation of compounds of the Formula Ia(v) and Ia(vi): To a solution of azeotropically dried A-ring phosphine oxide VIII(i) (95.0 mg, 0.163 mmol) in THF (4 mL) was added 0.096 mL of n-BuLi (1.70 M in Hexane, 0.163 mmol) at −78° C. The solution was stirred for 30 min at the same temperature. A pre-cooled (−78° C.) solution of azeotropically dried C24-fluoro C/D ring ketone (+)-E-VIIa(v) (32.3 mg, 0.091 mmol) in THF (2 mL) was added to the above solution at −78° C. via cannula. The resulting solution was stirred for 5 hrs at −78° C. The reaction was quenched with 2 mL of pH 7 buffer, then warmed to room temperature, extracted with EtOAc (3×25 mL), dried over. MgSO$_4$, filtered, concentrated in vacuo, and purified by flash chromatography (EtOAc:Hex=1:11 to 1:3 to 1:1) to give 30.8 mg (47%) of a diastereomeric mixture of bis TBS protected Ia(v) and Ia(vi). A solution of the above mixture of bis TBS protected Ia(v) and Ia(vi) (30.8 mg, 0.043 mmol) in EtOH (2 mL) was treated with 0.35 mL of 49% aq HF. The crude desilylated mixture was purified by flash chromatography (1:1 to 3:1 EtOAc:Hex) to afford (18.5 mg, 89%) a diastereomeric mixture of Ia(v) and Ia(vi) as a clear oil. The diastereomers were separated by reverse phase HPLC (Phenomenex Luna 5u C18 semipreparative column, 50% MeCN/water, 3 mL/min, 254 nm) to afford 9.0 mg of (+)-Ia(v) (1α,3β, t$_R$ 88.9 min) as a viscous oil and 5.4 mg of (+)-Ia(vi) (1β,3α, t$_R$ 81.3 min) as a viscous oil.

(+)-Ia(v): $^1$H NMR (400 MHz, CDCl$_3$) δ 6.37 (d, J=11.6 Hz, 1H), 6.10 (d, J=11.6 Hz, 1H), 6.06 (dt, J=33.2, 7.6, 1H), 5.38 (m, 1H), 5.34 (t, J=1.6 Hz, 1H), 5.01 (m, 1H), 4.45 (m, 1H), 4.25 (m, 1H), 2.82 (dd, J=12.8, 5.2 Hz, 1H), 2.64-2.56 (m, 1H), 2.54-2.45 (m, 1H), 2.42-2.28 (m, 4H), 2.25-2.17 (m, 1H), 2.08-1.99 (m, 2H), 1.94-1.88 (m, 1H), 1.85-1.74 (m, 3H), 1.72-1.48 (m, 4H), 1.40 (d, J=0.8 Hz, 9H), 1.11 (d, J=6.4 Hz, 3H), 0.70 (s, 3H).

(+)-Ia(vi): $^1$H NMR (400 MHz, CDCl$_3$) δ 6.38 (d, J=11.6 Hz, 1H), 6.09 (d, J=10.8 Hz, 1H), 6.06 (dt, J=33.2, 7.6, 1H), 5.37 (t, J=1.2 Hz, 1H), 5.33 (m, 1H), 5.01 (m, 1H), 4.47-4.44 (m, 1H), 4.25-4.20 (m, 1H), 2.82 (dd, J=12.4, 4.8 Hz, 1H), 2.62 (dd, J=13.2, 4.0 Hz, 1H), 2.54-2.45 (m, 1H), 2.43-2.27 (m, 4H), 2.24-2.17 (m, 1H), 2.14-1.99 (m, 2H), 1.97-1.48 (m, 8H), 1.40 (d, J=1.2 Hz, 9H), 1.11 (d, J=6.4 Hz, 3H), 0.69 (s, 3H).

(b) Preparation of compounds of the Formula Ib(v) and Ib(vi): To a solution of A-ring phosphine oxide VIII(i) (48.0 mg, 0.0825 mmol) in THF (4 mL) was added 0.040 mL of n-BuLi (2.08 M in Hexane, 0.825 mmol) at −78° C. The solution was stirred for 30 min at the same temperature. A pre-cooled (−78° C.) solution of C24-fluoro C/D ring ketone (+)-Z-VIIa(vi) (16.5 mg, 0.046 mmol) in THF (2 mL) was added to the above solution at −780° C. via cannula. The resulting solution was stirred for 5.5 hrs at −78° C. The reaction was quenched with 2 mL of pH 7 buffer, then warmed to room temperature, extracted with EtOAc (3×20 mL), dried over MgSO$_4$, filtered, concentrated in vacuo, and purified by flash chromatography (EtOAc:Hex=1:11 to 1:1) to give 26.7 mg (80%) of a diastereomeric mixture of bis TBS protected Ib(v) and Ib(vi). A solution of the above mixture of bis TBS protected Ib(v) and Ib(vi) (26.7 mg, 0.037 mmol) in EtOH (2 mL) was treated with 0.35 mL of 49% aq HF. The crude desilylated mixture was purified by flash chromatography (EtOAc:Hex=1:1) to afford (17.2 mg, 95%) a diastereomeric mixture of Ib(v) and Ib(vi) as a clear oil. The diastereomers were separated by reverse phase HPLC (C-18 semipreparative column, 50% MeCN/H$_2$O, 3.0 ml/min) to afford 8.9 mg (39%) of (+)-Ib(v) (1α, 3β, t$_R$ 104.35 min) as a white solid and 3.1 mg (14%) of (+)-Ib(vi) Ib(vi)(1β, 3α, t$_R$ 96.33 min) as a white solid.

(+)-Ib(v): [α]$_D$ +1.8 (c 1.0, CHCl$_3$); $^1$H NMR (400 MHz, CDCl$_3$) δ 6.37 (d, J=11.2 Hz, 1H), 6.11 (d, J=11.2 Hz, 1H), 6.06 (dt, J=23.6, 8.0, 1H), 5.40-5.39 (m, 1H), 5.34 (m, 1H), 5.01 (m, 1H), 4.46-4.43 (m, 1H), 4.25-4.24 (m, 1H), 2.82 (dd, J=12.0, 4.4 Hz, 1H), 2.68-2.64 (m, 2H), 2.60 (dd, J=13.6, 2.8 Hz, 1H) 2.40-2.21 (m, 4H), 2.08-2.00 (m, 2H), 1.94-1.88 (m, 1H), 1.85-1.73 (m, 3H), 1.71-1.49 (m, 4H), 1.41 (d, J=1.2 Hz, 9H), 1.09 (d, J=7.2 Hz, 3H), 0.70 (s, 3H); $^{13}$C NMR (100 MHz, CDCl$_3$) δ 158.85, 152.02, 148.65, 143.04, 134.26, 125.78, 124.25 (d, J=12.9 Hz). 123.14, 118.06, 112.65, 71.65, 67.86, 61.37, 59.30, 50.99, 46.15, 43.94, 36.14, 33.79 (d, J=6.0 Hz), 32.03 (d, J=8.8 Hz), 30.46, 29.70, 24.51, 23.98, 22.27, 17.91; UV (MeOH) λ$_{max}$ 270 nm (ε 11,900); IR (thin film) 3389, 3037, 2931, 2849, 1655, 1455, 1320, 1102, 1055, 756 cm$^{-1}$; HRMS [M+Na] calcd 515.260176. Found 515.25601.

(+)-Ib(vi): $^1$H NMR (400 MHz, CDCl$_3$) $^1$H NMR (400 MHz, CDCl$_3$) δ 6.39 (d, J=11.2 Hz, 1H), 6.10 (d, J=11.6 Hz, 1H), 6.06 (dt, J=23.6, 8.0, 1H), 5.40 (m, 1H), 5.33 (m, 1H), 5.02 (m, 1H), 4.45 (m, 1H), 4.23 (m, 1H), 2.83 (dd, J=12.4, 4.0 Hz, 1H), 2.68-2.65 (m, 2H), 2.62-2.61 (m, J=1H) 2.40-2.20 (m, 4H), 2.06-2.00 (m, 2H), 1.95-1.89 (m, 1H), 1.84-1.75 (m, 3H), 1.56-1.51 (m, 4H), 1.42 (d, J=0.4 Hz, 9H), 1.09 (d, J=7.2 Hz, 3H), 0.69 (s, 3H).

(c) Preparation of compounds of the Formula Ia(vii), Ia(viii), Ib(vii) and Ib(viii): To a solution of A-ring phosphine oxide (61.0 mg, 0.105 mmol) in THF (3 mL) was added 65.0 μL of n-BuLi (1.60 M in Hexane, 0.105 mmol) at −78° C. The reddish solution was stirred for 10 min at the same temperature. A precooled (−78° C.) solution of C24-fluoro C/D ring ketones (+)-E-VIIa(vii) and (+)-Z-VIIa(viii) (25.0 mg, 0.066 mmol) in THF (3 mL) was added to the above solution at −78° C. via cannula. The resulting reddish orange solution was stirred for 4 hrs at −78° C. The reaction was quenched with 3 mL of pH 7 buffer, then warmed to room temperature, extracted with EtOAc (3×20 mL), dried over MgSO$_4$, filtered, concentrated in vacuo, and purified by flash chromatography (8% EtOAc in hexanes) to give 37.4 mg (76%) of a diastereomeric mixture of bis TBS protected Ia(vii), Ia(viii), Ib(vii) and Ib(viii). A solution of the above mixture of bis TBS protected Ia(vii), Ia(viii), Ib(vii) and Ib(viii) (37.4 mg, 0.051 mmol) in EtOH (3 mL) was treated with 0.5 mL of 49% aq HF. The crude desilylated mixture was purified by flash chromatography (70% EtOAc in hexanes) to afford (26.1 mg, 100%) of a diastereomeric mixture of Ia(vii), Ia(viii), Ib(vii) and Ib(viii) as a white solid. Approximately half of the diastereomeric mixture was separated by reverse phase HPLC (Phenomenex Luna 5u C18 semipreparative column, 50% MeCN/water, 2.8 mL/min, 254 nm) to afford 5.5 mg (21%) of Ia(vii) (E-1a, 3b, $t_R$ 145.9 minutes) as a foaming solid. The remaining mixture remained unseparated pending biological testing results of compound Ia(vii).

Ia(vii): $[\alpha]^{24}_D$ +8.41 (c 0.27, CHCl$_3$); $^1$H NMR (400 MHz, CDCl$_3$) δ 7.94-7.90 (m, 2H), 7.69 (tt, J=7.2, 1.2 Hz, 1H), 7.60-7.55 (m, 2H), 6.36 (d, J=11.6 Hz, 1H), 6.19 (dt, J=32.8, 7.6 Hz, 1H), 6.09 (d, J=11.6, 1H), 5.37 (t, J=1.6 Hz, 1H), 5.31 (m, 1H), 5.02 (t, J=1.6 Hz, 1H), 4.60 (m, 1H), 4.25 (m, 1H), 2.81 (dd, J=12, 4 Hz, 1H), 2.61 (dd, J=13.6, 3.6, 1H), 2.43-2.24 (m, 5H), 2.17-1.45 (m, 9H), 1.06 (d, J=6.4 Hz, 3H), 0.64 (s, 3H); $^{13}$C NMR (100 MHz, CDCl$_3$) d 157.65, 154.30 (d, J=292.4 Hz), 147.71, 141.96, 137.64, 133.29, 129.33, 124.75, 121.83, 117.57 (d, J=6.8 Hz), 117.05, 111.59, 70.64, 66.85, 58.20, 49.96, 45.16, 42.89, 35.14, 32.03, 30.71, 29.38, 28.65, 23.47, 21.40, 16.90; $^{19}$F NMR (376 MHz, CDCl$_3$, CFCl$_3$ as internal standard) δ −128.39 (d, J=32.0 Hz); IR (neat, cm$^{-1}$) 3366, 3060, 2931, 2837, 2355, 1666, 1649, 1443, 1337, 1155, 1085, 1044, 756, 720, 685, 603, 579; HRMS m/z (M$^+$+Na$^+$) calcd 535.2289 for C$_{30}$H$_{37}$FO$_4$SNa$^+$. Found 535.2288.

Example 7

Methoxymethyl t-butyl sulfone XII(iii)

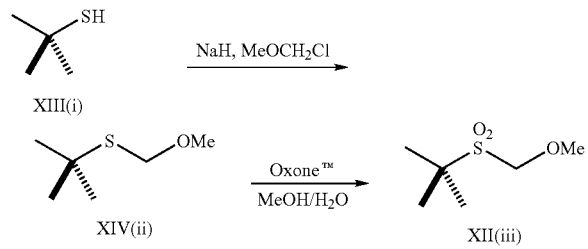

The suspension of NaH (60% dispersion in mineral oil, 1.33 g, 0.033 mol) in anhydrous THF (40 mL) was cooled in an ice bath and 2-methyl-2-propanethiol XIII(i)(3.0 g, 0.033 mol) was added during 10 min. The ice bath was removed and the mixture was stirred vigorously for 15 min. The reaction mixture was cooled again and dry MeOH (30 mL) was added slowly, and then it was stirred for 10 min and chloromethyl methyl ether (2.53 mL, 0.033 mol) was added during 5 min. The mixture was stirred for 15 min at 0° C. and stirred for 30 min at room temperature. Et$_2$O (40 mL) was added and the mixture was cooled to coagulate the salts. The mixture was filtered and the precipitate was washed with Et$_2$O (30 mL). The filtrate was dried over MgSO$_4$, concentrated in vacuo to yield methoxymethyl t-butyl sulphide XIV(ii) as a pale yellow oil. Distillation through water pump (bp 40-44° C.) gave 2.68 g (60%) of pure sulfide as a pale yellow oil.

To a solution of methoxymethyl t-butyl sulphide XIV(ii) (2.68 g, 0.020 mol) in MeOH (80 mL) was added a solution of potassium peroxymonosulfate (2 KHSO$_5$ KHSO$_4$ K$_2$SO$_4$, Oxone®) (36.8 g, 0.060 mol) in water (80 mL) at 0° C. The resulting cloudy solution was warmed to room temperature and then stirred overnight. The mixture was diluted with water (30 mL), extracted with EtOAc (3×70 mL), washed with brine, dried over MgSO$_4$, concentrated in vacuo, and then purified by column chromatography (25% EtOAc/hexanes) to give 3.05 g (92%) of Methoxymethyl t-butyl sulfone XII(iii) as a colorless oil: $^1$H NMR (400 MHz, CDCl$_3$) δ 4.50 (s, 2H), 3.63 (s, 3H), 1.38 (s, 9H); $^{13}$NMR (100 MHz, CDCl$_3$) δ 83.19, 60.84, 59.61, 23.32.

Example 8

16,23E/Z-Diene-24-OMe-25-SO$_2$tBu-TES-C,D-ring E/Z-Xa(v)

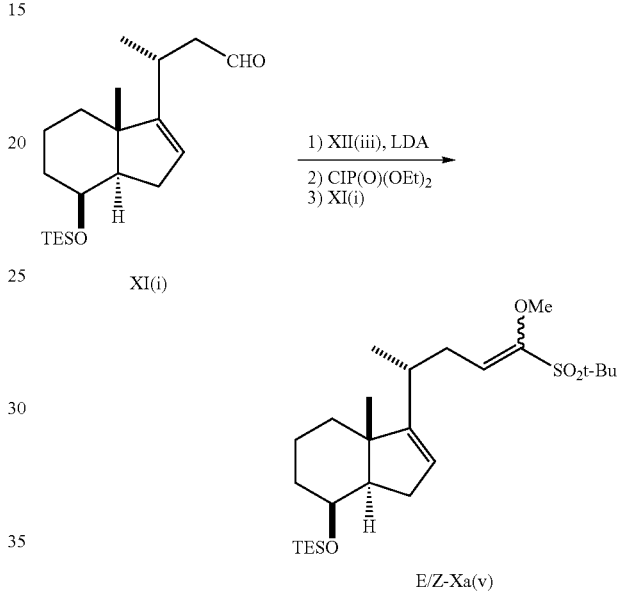

To a solution of diisopropylamine (131.52 μL, 0.94 mmol) in THF (2 mL) was added 0.89 mL of nBuLi (1.05 M in hexanes, 0.94 mmol) at −78° C. After 30 min stirring, a precooled (−78° C.) solution of methoxymethyl t-butyl sulfone XII(iii) (83.6 mg, 0.50 mmol) in THF (1 mL) was added. After 15 min, diethyl chlorophosphate (72.9 μL, 0.50 mmol) was added dropwise. After 1 h stirring at −78° C., a precooled (−78° C.) solution of 16-ene-23-aldehyde-TES-C,D ring XI(i) (112.8 mg, 0.34 mmol) in THF (2 ml) was added via cannula. The mixture was warmed to room temperature after 15 min and allowed to stir overnight. Water (5 mL) was added and reaction solution was extracted with Et$_2$O (3×10 mL), washed with brine, dried over MgSO$_4$, concentrated in vacuo, and then purified by column chromatography (5% EtOAc/hexanes) to give 37.8 mg (23%) of 16,23E-diene-24-OMe-25-SO$_2$tBu-TES-C,D ring E-Xa(v) as a colorless oil and 94.5 mg (58%) of 16,23Z-diene-24-OMe-25-SO$_2$tBu-TES-C,D ring Z-Xa(v) as a colorless oil respectively.

16,23E-diene-24-OMe-25-SO$_2$tBu-TES-C,D ring E-Xa (v): $[\alpha]^{25}_D$ +15.3 (c 0.68, CHCl$_3$); $^1$H NMR (400 MHz, CDCl$_3$) δ 6.20 (t, J=7.2 Hz, 1H), 5.32 (t, J=1.6 Hz, 1H), 4.11 (d, J=2.4 Hz, 1H), 3.87 (s, 3H), 2.49 (qt, J=8.0 Hz, 1H), 2.34 (qt, J=8.0 Hz, 1H), 2.28-2.18 (m, 2H), 1.92-1.85 (m, 2H), 1.74-1.61 (m, 3H), 1.53-1.45 (m, 3H), 1.35 (s, 9H), 1.05 (d, J=6.8 Hz, 3H), 1.00 (s, 3H), 0.95 (t, J=8.0 Hz, 9H), 0.55 (q, J=8.0 Hz, 6H); $^{13}$NMR (100 MHz, CDCl$_3$) δ 158.80, 150.99, 130.65, 120.99, 68.84, 63.06, 59.32, 54.98, 46.76, 35.87, 34.83, 32.56, 31.29, 30.73, 23.53, 22.04, 18.79, 18.04, 6.93, 4.90; IR (neat, cm$^{-1}$) 2955, 2919, 2860, 1641, 1457, 1291, 1112, 1083, 1029, 739, 721, 662; HRMS m/z (M+Na) calc'd 507.2935 for $C_{26}H_{48}O_4SSiNa^+$. Found 507.2956.

16,23Z-diene-24-OMe-25-SO$_2$tBu-TES-C,D ring Z-Xa (v): $[\alpha]^{25}_D$ +9.88 (c 0.83, CHCl$_3$); $^1$H NMR (400 MHz, CDCl$_3$) δ 5.45 (t, J=7.2 Hz, 1H), 5.35 (t, J=1.2 Hz, 1H), 4.12 (d, J=2.0 Hz, 1H), 3.65 (s, 3H), 2.77 (qt, J=8.0 Hz, 1H), 2.62 (qt, J=8.0 Hz, 1H), 2.26 (t, J=13.2 Hz, 1H), 2.15 (sextet, J=7.2 Hz, 1H), 1.93-1.85 (m, 2H), 1.73-1.61 (m, 3H), 1.53-1.32 (m, 3H), 1.38 (s, 9H), 1.03 (d, J=7.2 Hz, 3H), 1.01 (s, 3H), 0.95 (t, J=8.0 Hz, 9H), 0.55 (q, J=8.0 Hz, 6H); $^{13}$NMR (100 MHz, CDCl$_3$) δ 158.91, 149.25, 121.12, 118.00, 68.89, 60.41, 58.01, 55.05, 46.63, 35.61, 34.87, 32.53, 31.98, 30.77, 23.41, 22.17, 18.81, 18.01, 6.93, 4.89; IR (neat, cm$^{-1}$) 2948, 2924, 2875, 1627, 1455, 1302, 1112, 1075, 719, 498, 474, 468; HRMS m/z (M+Na) calc'd 507.2935 for $C_{26}H_{48}O_4SSiNa^+$. Found 507.2945.

Example 9a 16.23E-Diene-24-OMe-25-SO$_2$tBu-C,D-ring Ketone (+)-E-VIIa(ix)

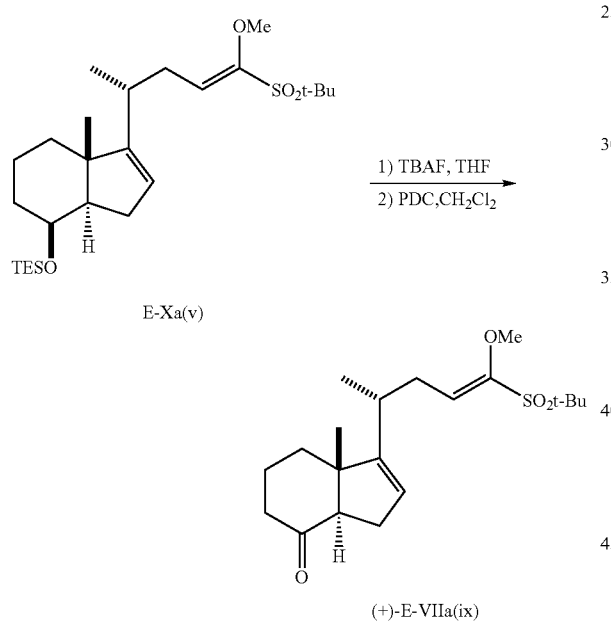

E-Xa(v)

(+)-E-VIIa(ix)

To a solution of 16,23E-diene-24-OMe-25-SO$_2$tBu-TES-C,D ring E-Xa(v) (10 mg, 0.021 mmol) in THF (2 mL) was added 61.88 µL of TBAF (1 M in THF, 0.062 mmol) dropwise at 0° C. The resulting mixture was stirred at 0° C. for 1 h and stirred overnight at room temperature. Water (5 mL) was added and the solution was extracted with EtOAc (2×10 mL), washed with brine, dried over MgSO4, concentrated in vacuo, and then purified by column chromatography (50% EtOAc/hexanes) to give 6.8 mg (90%) of desired alcohol as a colorless oil. To a solution of the deprotected C,D-ring alcohol (6.8 mg, 0.018 mmol) in CH$_2$Cl$_2$ (5 mL) was added 20 mg of oven-dried Celite and PDC (20 mg, 0.051 mmol) at room temperature. The reaction mixture was stirred overnight and then passed through a 2 cm pad of flash silica gel and washed with EtOAc. The filtrate was concentrated and purified by column chromatography (33% EtOAc/hexanes) to give 4.6 mg (68%) of the desired C,D-ring ketone E-VIIa(ix) as a colorless oil: $[\alpha]^{25}_D$ +28.1 (c 0.30, CHCl$_3$); $^1$H NMR (400 MHz, CDCl$_3$) δ 6.17 (t, J=7.2 Hz, 1H), 5.35 (t, J=1.6 Hz, 1H), 3.87 (s, 3H), 2.85 (dd, J=10.8, 6.4 Hz, 1H), 2.54-2.27 (m, 6H), 2.16-1.95 (m, 3H), 1.92-1.87 (m, 1H), 1.80 (dt, J=12.8, 5.6 Hz, 1H), 1.34 (s, 9H), 1.12 (d, J=6.8 Hz, 3H), 0.8 (s, 3H); $^{13}$NMR (100 MHz, CDCl$_3$) δ 210.56, 156.48, 151.43, 129.61, 121.49, 63.05, 62.94, 59.31, 53.71, 40.39, 34.45, 32.35, 32.21, 27.09, 23.94, 23.50, 21.56, 17.25; IR (neat, cm$^{-1}$) 2928, 1717, 1644, 1460, 1375, 1293, 1121, 1064, 951, 802, 668, 574; HRMS m/z (M+Na) calc'd 391.1913 for $C_{20}H_{32}O_4SNa^+$. Found 391.1900.

Example 9b 16,23Z-Diene-24-OMe-25-SO$_2$tBu-C,D-ring ketone (+)-Z-VIIa(x)

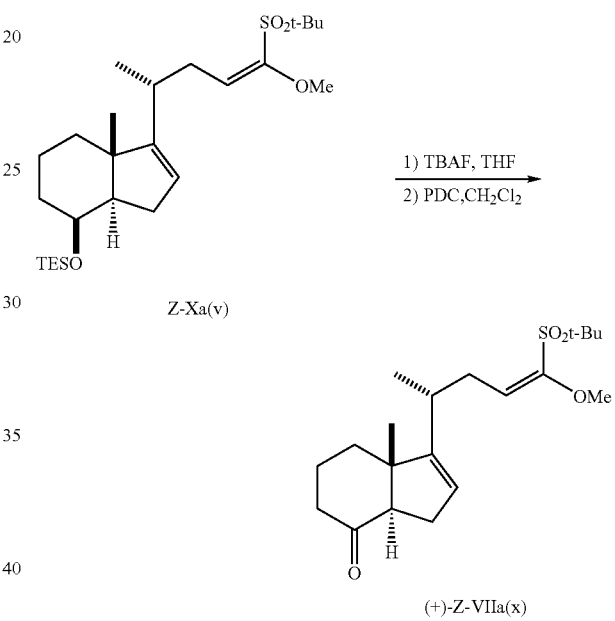

Z-Xa(v)

(+)-Z-VIIa(x)

To a solution of 16,23Z-diene-24-OMe-25-SO$_2$tBu-TES-C,D ring Z-Xa(v) (50 mg, 0.10 mmol) in THF (10 mL) was added 0.31 mL of TBAF (1 M in THF, 0.31 mmol) dropwise at 0° C. The resulting mixture was stirred at 0° C. for 1 h and stirred overnight at room temperature. Water (10 mL) was added and the solution was extracted with EtOAc (2×20 mL), washed with brine, dried over MgSO4, concentrated in vacuo, and then purified by column chromatography (50% EtOAc/hexanes) to give 33.6 mg (88%) of desired alcohol as a colorless oil. To a solution of the deprotected C,D-ring alcohol (30 mg, 0.081 mmol) in CH$_2$Cl$_2$ (10 mL) was added 80 mg of oven-dried Celite and PDC (85.3 mg, 0.23 mmol) at room temperature. The reaction mixture was stirred overnight and then passed through a 2 cm pad of flash silica gel and washed with EtOAc. The filtrate was concentrated and purified by column chromatography (33% EtOAc/hexanes) to give 23.8 mg (79%) of the desired C,D-ring ketone Z-VIIa(x) as a white solid: mp 104-106° C.; $[\alpha]^{24}$ D+12.0 (c 1.10, CHCl$_3$); $^1$H NMR (400 MHz, CDCl$_3$) δ 5.38 (t, J=7.6 Hz, 1H), 5.36 (brs, 1H), 3.63 (s, 3H), 2.85 (dd, J=10.8, 6.4 Hz, 1H), 2.75-2.62 (m, 2H), 2.44 (tq, J=10.8, 1.6 Hz, 1H), 2.32-2.20 (m, 3H), 2.15-2.05 (m, 2H), 2.04-1.95 (m, 1H), 1.93-1.88 (m, 1H), 1.77 (dt, J=12.4, 5.6 Hz, 1H), 1.36 (s, 9H), 1.09 (d, J=7.2 Hz, 3H), 0.80 (s, 3H); $^{13}$NMR (100 MHz, CDCl$_3$) δ 210.79, 156.81, 149.87, 121.43, 116.57, 62.99, 60.45, 57.90, 53.75, 40.44, 34.16, 33.57, 31.86, 27.09, 23.94, 23.37, 21.44, 17.25; IR (neat, cm$^{-1}$) 2966, 2940, 2355, 1718, 1705, 1459, 1306, 1107, 967, 681, 568, 502; HRMS m/z (M+Na) calc'd 391.1913 for $C_{20}H_{32}O_4SNa^+$. Found 391.1915.

Example 10

Preparation of Compounds Ia(ix), Ia(x), Ib(ix) and Ib(x)

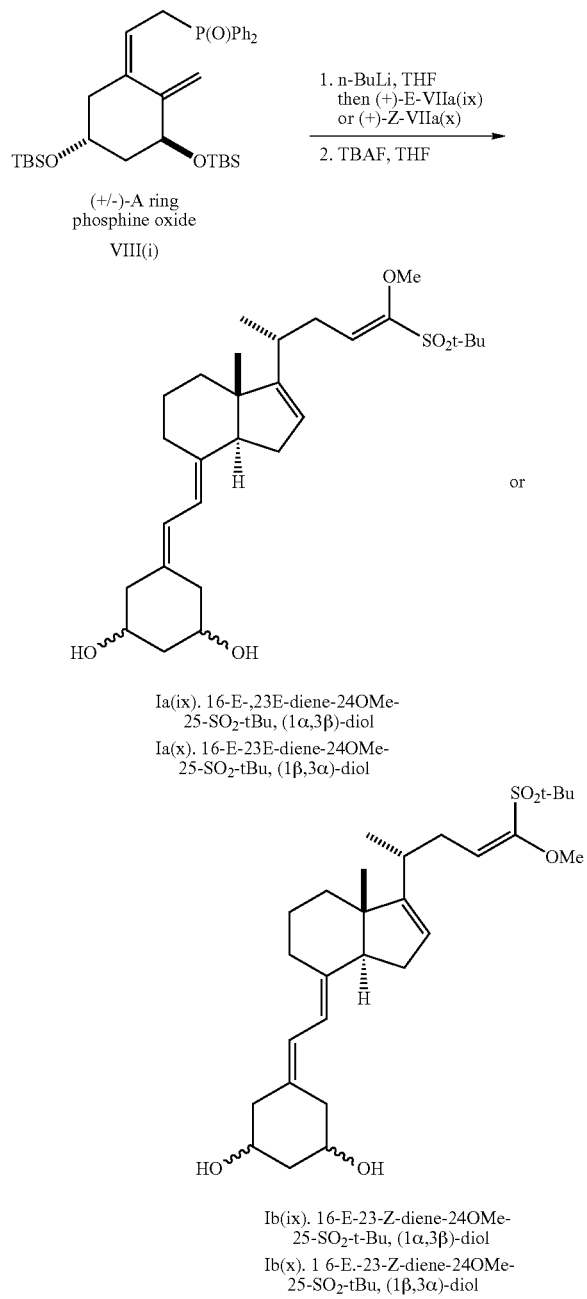

Ia(ix). 16-E-,23E-diene-24OMe-25-SO$_2$-t-Bu, (1α,3β)-diol
Ia(x). 16-E-23E-diene-24OMe-25-SO$_2$-tBu, (1β,3α)-diol Ib(ix). 16-E-23-Z-diene-24OMe-25-SO$_2$-t-Bu, (1α,3β)-diol
Ib(x). 1 6-E.-23-Z-diene-24OMe-25-SO$_2$-tBu, (1β,3α)-diol (a) 16,23E-Diene-24-OMe-25-SO$_2$TB Analogues Ia(ix) and Ia(x). A solution of 45.1 mg (0.077 mmol) of racemic phosphine oxide VIII(i) in 1.0 mL of anhydrous THF was cooled to −78° C. and treated with 53.2 μL (0.077 mmol, 1.6 M in hexanes) of n-BuLi under argon atmosphere. The mixture turned reddish orange and was stirred for 10 min at −78° C. To the solution was added dropwise a solution of 26.4 mg (0.072 mmol) of the C,D-ring ketone E-VIIa(ix) in 1.0 mL of anhydrous THF. The reaction kept going until the reddish orange color faded to yellow (about 3 h). The reaction was quenched by adding 3.0 mL of pH 7 buffer, then warmed to room temperature, extracted with EtOAc (20 mL×2), washed with brine, dried over MgSO$_4$, concentrated in vacuo, and then purified by column chromatography (33%→50% EtOAc/hexanes→EtOAc only) to afford 27.2 mg (57%) of the coupled product as a colorless oil.

The coupled product (27.2 mg, 0.037 mmol) was dissolved in 5 mL of anhydrous THF, and to this solution was added 0.15 mL (0.15 mmol) of a 1.0 M solution of TBAF in THF. The reaction was run in darkness overnight, then extracted with EtOAc (30 mL×2), washed with brine, dried over MgSO$_4$, concentrated in vacuo, and then purified by column chromatography (60%→80% EtOAc/hexanes→EtOAc only) to give 15.1 mg (81%) of a mixture of two diastereomers as a colorless oil. The diastereomers were separated by reverse-phase HPLC (C-18 semipreparative column, 48% MeCN/H$_2$O, 3.0 mL/min) to afford 4.6 mg (25%) of Ia(ix) (1α, 3β, $t_R$ 117 min) and 3.6 mg (19%) of Ia(x) (1β, 3α, $t_R$ 106 min) as colorless oils. Ia(ix): $[\alpha]^{24}_D$ +16.9 (c 0.23, CHCl$_3$); $^1$H NMR (400 MHz, CDCl$_3$) δ 6.37 (d, J=11.2 Hz, 1H), 6.20 (t, J=7.6 Hz, 1H), 6.10 (d, J=11.2 Hz, 1H), 5.37-5.33 (m, 2H), 5.00 (t, J=1.6 Hz, 1H), 4.45 (dd, J=8.4, 4.8 Hz, 1H), 4.27-4.21 (m, 1H), 3.87 (s, 3H), 2.82 (dd, J=12.0, 4.4 Hz, 1H), 2.60 (dd, J=14.0, 3.6 Hz, 1H), 2.48 (qt, J=7.2 Hz, 1H), 2.40-2.27 (m, 4H), 2.23-2.16 (m, 1H), 2.09-1.97 (m, 2H), 1.93-1.87 (m, 1H), 1.83-1.74 (m, 3H), 1.37-1.36 (m, 2H), 1.36 (s, 9H), 1.09 (d, J=6.8 Hz, 3H), 0.69 (s, 3H); $^{13}$NMR (100 MHz, CDCl$_3$) δ 158.80, 150.98, 147.90, 142.12, 133.28, 130.15, 124.80, 121.64, 117.09, 111.62, 70.62, 66.86, 63.05, 59.32, 58.28, 50.04, 45.13, 42.87, 35.32, 32.40, 32.31, 29.69, 29.43, 28.71, 23.54, 21.45, 16.96; IR (neat, cm$^{-1}$) 3460, 3025, 2919, 2837, 1708, 1660, 1455, 1290, 1214, 1114, 1061, 756, 662, 615, 568. Ia(x): $[\alpha]^{24}_D$ −24 (c 0.17, CHCl$_3$); $^1$H NMR (400 MHz, CDCl$_3$) δ 6.38 (d, J=10.8 Hz, 1H), 6.19 (t, J=7.2 Hz, 1H), 6.08 (d, J=11.2 Hz, 1H), 5.36-5.32 (m, 2H), 5.00 (m, 1H), 4.44-4.42 (m, 1H), 4.21-4.18 (m, 1H), 3.87 (s, 3H), 2.99-2.93 (m, 1H), 2.64-2.60 (m, 1H), 2.51-2.44 (m, 1H), 2.39-2.27 (m, 4H), 2.22-2.16 (m, 1H), 2.07-1.97 (m, 2H), 1.94-1.86 (m, 1H), 1.79-1.67 (m, 3H), 1.60-1.49 (m, 2H), 1.36 (s, 9H), 1.09 (d, J=6.4 Hz, 3H), 0.68 (s, 3H); $^{13}$C NMR (100 MHz, CDCl$_3$) δ 158.82, 150.98, 147.88, 141.12, 133.25, 130.14, 124.82, 121.24, 117.10, 111.58, 70.62, 66.85, 63.10, 59.22, 58.25, 50.10, 45.13, 42.85, 35.32, 32.40, 32.33, 29.65, 29.42, 28.70, 23.54, 21.43, 16.95; IR (neat, cm$^{-1}$) 3448, 3025, 2931, 2872, 2849, 1713, 1643, 1454, 1290, 1214, 1114, 1061, 756, 661, 614, 573; HRMS m/z (M+Na) calc'd 527.2802 for $C_{29}H_{44}O_5SNa^+$. Found 527.2804.

(b) 16,23Z-Diene-24-OMe-25-SO$_2$TB Analogues Ib(ix) and Ib(x). A solution of 50.8 mg (0.086 mmol) of azeotropically dried racemic phosphine oxide VIII(i) in 1.0 mL of anhydrous THF was cooled to −78° C. and treated with 53.6 μL (0.086 mmol, 1.6 M in hexanes) of n-BuLi under argon atmosphere. The mixture turned reddish orange and was stirred for 10 min at −78° C. To the solution was added dropwise a solution of 22.6 mg (0.061 mmol) of the azeotropically dried C,D-ring ketone Z-VIIa(x) in 1.0 mL of anhydrous THF. The reaction kept going until the reddish orange color faded to yellow (about 3 h). The reaction was quenched by adding 3.0 mL of pH 7 buffer, then warmed to room temperature, extracted with EtOAc (20 mL×2), washed with brine, dried over MgSO$_4$, concentrated in vacuo, and then purified by column chromatography (33%→50%→66% EtOAc/hexanes) to afford 20.2 mg (45%) of the coupled product as a colorless oil.

The coupled product (20 mg, 0.027 mmol) was dissolved in 5 mL of anhydrous THF, and to this solution was added 0.11 mL (0.11 mmol) of a 1.0 M solution of TBAF in THF. The reaction was run in darkness overnight, then extracted with EtOAc (30 mL×2), washed with brine, dried over MgSO$_4$, concentrated in vacuo, and then purified by column chromatography (66%→80% EtOAc/hexanes→EtOAc only) to give 12.1 mg (88%) of a mixture of two diastereomers as a colorless oil. The diastereomers were separated by reverse-phase HPLC (C-18 semipreparative column, 48% MeCN/H$_2$O, 3.0 mL/min) to afford 2.7 mg (20%) of Ib(ix) (1α, 3β, $t_R$ 86 min) and 2.3 mg (17%) of Ib(x) (1β, 3α, $t_R$ 80 min) as colorless oils. Ib(ix): $[α]^{24}_D$ +27.6 (c 0.11, CHCl$_3$); $^1$H NMR (400 MHz, CDCl$_3$) δ 6.38 (d, J=11.6 Hz, 1H), 6.11 (d, J=11.2 Hz, 1H), 5.44-5.39 (m, 2H), 5.34 (t, J=1.6 Hz, 1H), 5.01 (m, 1H), 4.46-4.42 (m, 1H), 4.26-4.21 (m, 1H), 3.65 (s, 3H), 2.84-2.80 (m, 1H), 2.75-2.65 (m, 2H), 2.63-2.58 (m, 1H), 2.41-2.29 (m, 2H) 2.26-2.19 (m, 2H), 2.06-1.99 (m, 2H), 1.95-1.89 (m, 1H), 1.82-1.76 (m, 3H), 1.39-1.38 (m, 2H), 1.38 (s, 9H), 1.07 (d, J=6.8 Hz, 3H), 0.69 (s, 3H); $^{13}$NMR (100 MHz, CDCl$_3$) δ 158.52, 149.54, 147.57, 142.34, 133.08, 124.88, 121.63, 117.39, 116.94, 111.79, 70.79, 66.85, 60.45, 58.32, 57.99, 50.01, 45.21, 42.84, 35.11, 33.48, 31.88, 29.69, 29.44, 23.41, 21.47, 16.95; IR (neat, cm$^{-1}$) 3413, 2919, 2837, 1713, 1661, 1625, 1454, 1367, 1302, 1140, 908, 755, 732; HRMS m/z (M+Na) calc'd 527.2802 for C$_{29}$H$_{44}$O$_5$SNa$^+$. Found 527.2784. Ib(x): $[α]^{24}_D$ +7.83 (c 0.12, CHCl$_3$); $^1$H NMR (400 MHz, CDCl$_3$) δ 6.39 (d, J=11.2 Hz, 1H), 6.10 (d, J=11.6 Hz, 1H), 5.44-5.38 (m, 2H), 5.32-5.31 (m, 1H), 5.01 (m, 1H), 4.45-4.44 (m, 1H), 4.25-4.21 (m, 1H), 3.65 (s, 3H), 2.99-2.94 (m, 1H), 2.76-2.65 (m, 2H), 2.63-2.57 (m, 1H), 2.40-2.29 (m, 2H) 2.27-2.19 (m, 2H), 2.06-1.98 (m, 2H), 1.96-1.89 (m, 1H), 1.83-1.76 (m, 3H), 1.40-1.38 (m, 2H), 1.38 (s, 9H), 1.07 (d, J=6.8 Hz, 3H), 0.69 (s, 3H); $^{13}$NMR (100 MHz, CDCl$_3$) δ 158.51, 149.52, 147.19, 142.33, 132.99, 124.85, 121.63, 117.42, 116.94, 112.61, 71.35, 66.75, 60.45, 58.31, 57.99, 50.02, 45.44, 42.80, 35.09, 33.48, 31.87, 29.47, 28.70, 23.52, 23.41, 21.45, 16.94; IR (neat, cm$^{-1}$) 3448, 3025, 2919, 2849, 1708, 1666, 1631, 1454, 1302, 1213, 1114, 1049, 750, 662, 585; HRMS m/z (M+Na) calc'd 527.2802 for C$_{29}$H$_{44}$O$_5$SNa$^+$. Found 527.2818.

Example 11

Preparation of Compounds of the Formula Ia(xi), Ia(xii), Ib(xi), and Ib(xii)

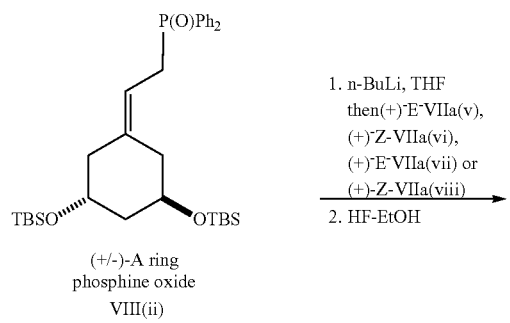

(+/−)-A ring phosphine oxide VIII(ii)

1. n-BuLi, THF then(+)-E-VIIa(v), (+)-Z-VIIa(vi), (+)-E-VIIa(vii) or (+)-Z-VIIa(viii)
2. HF-EtOH

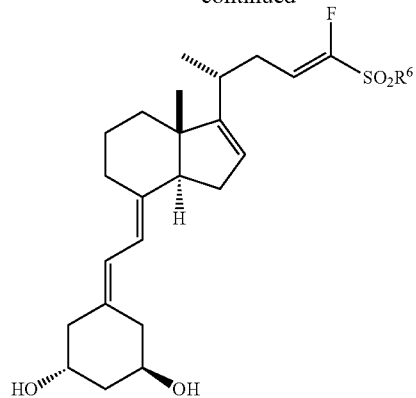

Ia(xi). 16-E-,23E-diene-24F-25-SO$_2$-tBu, (1α,3β)-diol, R$^6$ = t-Bu
Ia(xii). 16-E-23-E-diene-24-F-25-SO$_2$-Ph, (1β,3α)-diol, R$^6$ = Ph or

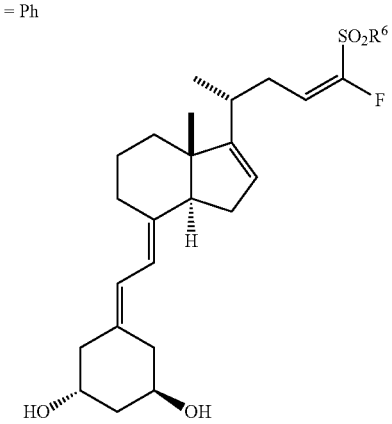

Ib(xi). 16-E-23-Z-diene-24F-25-SO$_2$-t-Bu, (1α,3β)-diol, R$^6$ = t-Bu
Ib(xii). 16-E.-23-Z-diene-24-F-25-SO$_2$-Ph, (1β,3α)-diol, R$^6$ = Ph (a) Preparation of the compounds of the Formula Ia(xi) and Ib(xi): A solution of 75 mg (0.13 mmol) of azeotropically dried (+)-19-nor-phosphine oxide VIII(ii) in 2.0 mL of anhydrous THF was cooled to −78° C. and treated with 81 μL (0.13 mmol, 1.6 M in hexanes) of n-BuLi under argon atmosphere. The mixture turned deep reddish and was stirred for 15 min at −78° C. To the solution was added dropwise a precooled (−78° C.) solution of 30 mg (0.084 mmol) of the azeotropically dried C,D-ring ketone (+)-E-VIIa(v) and (+)-Z-VIIa(vi) (E/Z=1.5/1 by $^1$H NMR) in 1.5 mL of anhydrous THF via cannula. The reaction kept going until the reddish orange color faded to yellow (about 2 hr). The reaction was quenched by adding 1.0 mL of pH 7 buffer (commercially available from ALDRICH) at −78° C., then warmed to room temperature, extracted with EtOAc (20 mL×2), washed with brine, dried over MgSO$_4$, concentrated. The residue was subjected to column chromatography with EtOAc/hexanes (1/4) as eluent to afford 20 mg (33%) of the coupled product as a colorless oil.

The coupled product (19 mg, 0.026 mmol) was dissolved in 2 mL of anhydrous EtOH, and to the solution was added 50

L of 49% aq. HF. The resulting mixture was stirred 2 hr at room temperature, then quenched with 5 mL of sat'd NaHCO$_3$ solution. The solution was stirred for 10 min, and then extracted with EtOAc (20 mL×3), washed with brine, dried over MgSO$_4$, concentrated. The residue was subjected to column chromatography with EtOAc as eluent to give 12 mg (94%) of the crude product of Ia(xi) and Ib(xi) (E/Z=1.4/1 by $^1$H NMR) as a light yellow oil. The crude product was purified by HPLC (Chiralcel OJ column, 10% EtOH in Hexanes, 2.0 mL/min, 254 nm) to afford 4.5 mg (38%) of Ia(xi) (t$_R$=29.1 min) and 2.6 mg (22%) of Ia(xi) and Ib(xi): (t$_R$=36.8 min).: Compound Ia(xi) [α]$^{25}_D$=+49.2 (c=0.20, CHCl$_3$). $^1$H NMR (400 MHz, CDCl$_3$) δ 6.29 (d, J=11.6 Hz, 1H), 6.06 (dt, J$_{d, H-F}$=33.2 Hz, J$_t$=7.6 Hz, 1H), 5.94 (d, J=11.2 Hz, 1H), 5.39 (m, 1H), 4.14 (m, 1H), 4.06 (m, 1H), 2.75-2.82 (m, 2H), 2.46-2.54 (m, 2H), 2.18-2.42 (m, 6H), 2.06 (ddd, J=14.8, 6.4, 3.2 Hz, 1H), 1.97 (m, 1H), 1.75-1.82 (m, 4H), 1.41-1.69 (m, 4H), 1.40 (d, J=0.8 Hz, 9H), 1.10 (d, J=6.4 Hz, 3H), 0.69 (s, 3H). $^{13}$C NMR (100 MHz, CDCl$_3$) δ 157.9, 154.3 (d, J=295.8 Hz), 141.8, 131.5, 123.6, 121.9, 121.7 (d, J=6.9 Hz), 115.4, 67.4, 67.2, 59.5, 58.2, 49.8, 44.5, 42.1, 37.2, 35.2, 32.1 (d, J=1.6 Hz), 31.1, 29.4, 28.5, 23.4, 23.3, 21.3, 17.1. $^{19}$F NMR (376 MHz, CDCl$_3$, CFCl$_3$ as internal) δ −119.4 (d, J=32.0 Hz). IR (neat, cm$^{-1}$) 3366, 2928, 2849, 1666, 1613, 1451, 1367, 1318, 1122, 1043, 977, 801, 756, 664. HRMS ([M+Na]$^+$) calcd. 503.2602. Found 503.2590. Compound Ib(xi) [α]$^{24}_D$=+45.0 (c=0.11, CHCl$_3$). $^1$H NMR (400 MHz, CDCl$_3$) δ 6.30 (d, J=11.2 Hz, 1H), 6.06 (dt, J$_{d, H-F}$=24.0 Hz, J$_t$=8.0 Hz, 1H), 5.95 (d, J=11.2 Hz, 1H), 5.42 (m, 1H), 4.14 (m, 1H), 4.06 (m, 1H), 2.74-2.82 (m, 2H), 2.67 (td, J$_t$=7.2 Hz, J$_d$=2.0 Hz, 2H), 2.49 (dd, J=13.2, 3.2 Hz, 1H), 2.40 (dd, J=11.2, 5.6 Hz, 1H), 2.20-2.33 (m, 4H), 2.07 (ddd, J=14.4, 5.6, 3.2 Hz, 1H), 1.97 (m, 1H), 1.75-1.83 (m, 4H), 1.42-1.72 (m, 4H), 1.42 (d, J=0.8 Hz, 9H), 1.09 (d, J=6.8 Hz, 3H), 0.69 (s, 3H). $^{13}$C NMR (100 MHz, CDCl$_3$) δ 158.0, 149.6 (d, J=293.0 Hz), 141.9, 131.4, 123.7, 123.3 (d, J=12.9 Hz), 122.1, 115.3, 67.4, 67.2, 60.4, 58.3, 49.8, 44.6, 42.1, 37.2, 35.1, 32.8 (d, J=1.5 Hz), 31.0, 29.4, 28.5, 23.4, 23.0, 21.3, 17.0. $^{19}$F NMR (376 MHz, CDCl$_3$, CFCl$_3$ as internal) δ −107.2 (d, J=24.1 Hz). IR (neat, cm$^{-1}$) 3356, 2927, 2849, 1655, 1615, 1454, 1318, 1103, 1046, 801, 756, 705. HRMS ([M+Na]$^+$) calcd. 503.2602. Found 503.2588.

(b) Preparation of the compounds of the Formula Ia(xii) and Ib(xii): A solution of 69 mg (0.12 mmol) of azeotropically dried (+)-19-nor-phosphine oxide VIII(ii) in 2.0 mL of anhydrous THF was cooled to −78° C. and treated with 80 μL (0.12 mmol, 1.5 M in hexanes) of n-BuLi under argon atmosphere. The mixture turned deep reddish and was stirred for 15 min at −78° C. To the solution was added dropwise a precooled (−78° C.) solution of 22 mg (0.058 mmol) of the azeotropically dried C,D-ring ketone (+)-E-VIIa(vii) and (+)-Z-VIIa(viii) (E/Z=2.1/1 by $^1$H NMR) in 1.5 mL of anhydrous THF via cannula. The reaction kept going until the reddish orange color faded to yellow (about 3 hr). The reaction was quenched by adding 1.0 mL of pH 7 buffer at −78° C., then warmed to room temperature, extracted with EtOAc (20 mL×2), washed with brine, dried over MgSO$_4$, concentrated. The residue was subjected to column chromatography with EtOAc/hexanes (1/3) as eluent to afford 32 mg (76%) of the coupled product as a colorless oil.

The coupled product (30 mg, 0.041 mmol) was dissolved in 2 mL of anhydrous EtOH, and to the solution was added 50 mL of aq. 49% HF. The resulting mixture was stirred 2 hr at room temperature, then quenched with 5 mL of sat'd NaHCO$_3$ solution. The solution was stirred for 10 min, and then extracted with EtOAc (20 mL×3), washed with brine, dried over MgSO$_4$, concentrated. The residue was subjected to column chromatography with EtOAc as eluent to give 20 mg (97%) of the crude product of Ia(xii) and Ib(xii): (E/Z=3.1/1 by $^1$H NMR) as a light yellow oil. The crude product was purified by HPLC (Chiralcel OJ column, 13% EtOH in Hexanes, 2.5 mL/min, 254 nm) to afford 10.5 mg of Ia(xii) (t$_R$=30.3 min) and 2.5 mg of Ib(xii) (t$_R$=46.2 min).: Compound Ia(xii) [α]$^{24}_D$=+53.3 (c=0.40, CHCl$_3$). $^1$H NMR (400 MHz, CDCl$_3$) δ 7.91-7.93 (m, 2H), 7.69 (m, 1H), 7.55-7.60 (m, 2H), 6.29 (d, J=11.2 Hz, 1H), 6.19 (dt, J$_{d, H-F}$=32.8 Hz, J$_t$=7.6 Hz, 1H), 5.92 (d, J=11.2 Hz, 1H), 5.33 (s, 1H), 4.14 (m, 1H), 4.07 (m, 1H), 2.74-2.80 (m, 2H), 2.49 (dd, J=13.2, 3.6 Hz, 1H), 2.13-2.45 (m, 7H), 1.94-2.03 (m, 2H), 1.44-1.84 (m, 8H), 1.06 (d, J=6.8 Hz, 3H), 0.63 (s, 3H). $^{13}$C NMR (100 MHz, CDCl$_3$) δ 157.7, 154.3 (d, J=291.6 Hz), 141.8, 137.7, 134.2, 131.5, 129.3, 128.5, 123.6, 121.8, 117.6 (d, J=6.8 Hz), 115.4, 67.4, 67.2, 58.2, 49.8, 44.6, 42.2, 37.2, 35.1, 32.1, 30.8, 29.4, 28.5, 23.4, 21.4, 17.0. $^{19}$F NMR (376 MHz, CDCl$_3$, CFCl$_3$ as internal) 8-128.3 (d, J=33.8 Hz). IR (neat, cm$^{-1}$) 3364, 2929, 1670, 1616, 1448, 1332, 1163, 1042, 753, 607. HRMS ([M+Na]$^+$) calcd. 523.2289. Found 523.2322. Compound Ib(xii) [α]$^{25}$ D=+68.5 (c=0.10, CHCl$_3$). $^1$H NMR (400 MHz, CDCl$_3$) δ 7.95-7.98 (m, 2H), 7.70 (m, 1H), 7.57-7.61 (m, 2H), 6.30 (d, J=11.2 Hz, 1H), 5.94 (d, J=11.2 Hz, 1H), 5.80 (dt, J$_{d, H-F}$=22.8 Hz, J$_t$=7.6 Hz, 1H), 5.42 (m, 1H), 4.13 (m, 1H), 4.06 (m, 1H), 2.73-2.82 (m, 4H), 2.48 (dd, J=13.6, 3.6 Hz, 1H), 2.40 (dd, J=11.2, 6.4 Hz, 1H), 2.19-2.33 (m, 4H), 2.06 (ddd, J=14.8, 6.4, 3.2 Hz, 1H), 1.97 (m, 1H), 1.25-1.82 (m, 8H), 1.10 (d, J=6.8 Hz, 3H), 0.67 (s, 3H). $^{13}$C NMR (100 MHz, CDCl$_3$) δ 158.0, 155.2 (d, J=292.0 Hz), 141.9, 138.4, 134.4, 131.4, 129.3, 128.3, 123.7, 122.2, 119.5 (d, J=12.9 Hz), 115.4, 67.4, 67.2, 58.3, 49.8, 44.6, 42.2, 37.2, 35.2, 32.9, 30.6, 29.4, 28.5, 23.4, 21.2, 17.0. $^{19}$F NMR (376 MHz, CDCl$_3$, CFCl$_3$ as internal) δ −116.0 (d, J=22.9 Hz). IR (neat, cm$^{-1}$) 3358, 2927, 1661, 1616, 1448, 1334, 1161, 1082, 1046, 801, 734. HRMS ([M+Na]$^+$) calcd. 523.2289. Found 523.2302.

Example 12

Preparation of C/D Ring Ketones (+)-E-VIIa(xi) and (+)-Z-VIIa(xii)

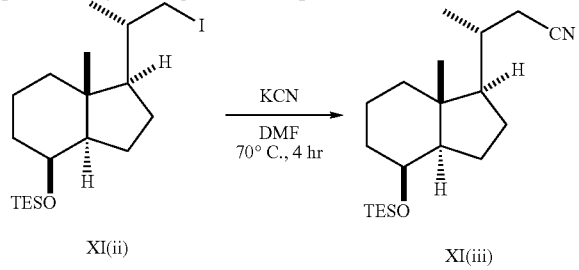

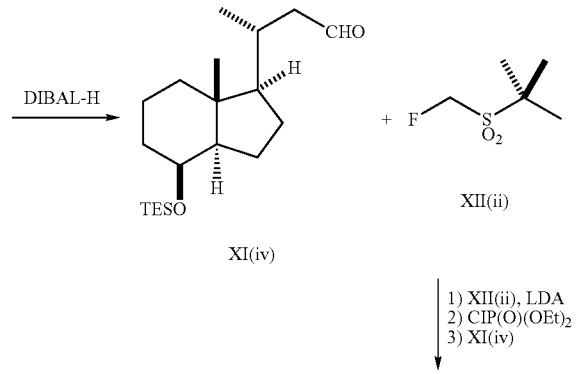

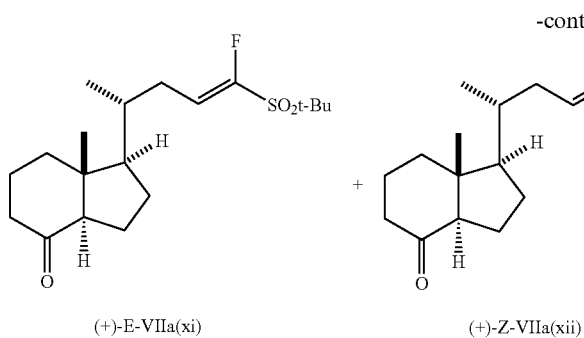

(+)-E-VIIa(xi)          (+)-Z-VIIa(xii)

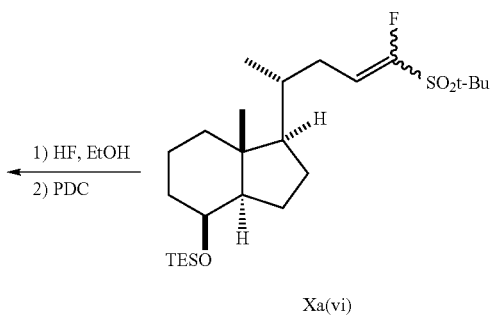

Xa(vi)

(a) Preparation of XI(iii): A solution of the iodide XI(ii) (95 mg, 0.22 mmol) and KCN (50 mg, 0.76 mmol) in DMF (4 mL) was heated to 70° C. for 4 hr. After cooling to room temperature, the reaction mixture was quenched with water (5 mL) and extracted with ether (15 mL×3). The organic layer was dried over MgSO$_4$ and concentrated in vacuo. The residue, the desired nitrile XI(iii) (70 mg, 95%), was used without any further purification.

(b) Preparation of XI(iv): To a solution of the nitrile XI(iii) (70 mg, 0.21 mmol) in CH$_2$Cl$_2$ (5 mL) was added DIBAL-H (1.5 M in Tol., 0.49 mL, 0.73 mmol) at 0° C. After stirring at 0° C. for 1 hr, the reaction mixture was quenched with aqueous 1 N HCl solution and extracted with CH$_2$Cl$_2$ (20 mL×2). The organic layer was dried over MgSO$_4$ and concentrated in vacuo. The residue was subjected to column chromatography with EtOAc/hexanes (1/10) as eluent to give the aldehyde XI(iv) (60 mg, 85%), that was used immediately in the next step.

(c) Preparation of Xa(vi): A solution of lithium diisopropylamide (0.54 mmol) was generated at −78 C by dropwise addition of n-butyllithium (1.0 M in hexanes, 0.54 mL, 0.54 mmol) to diisopropylamine (76 µL, 0.54 mmol). A precooled (−78 C) solution of tert-butyl fluoromethyl sulfone XII(ii) (42 mg, 0.27 mmol) was added via cannula as a solution in THF (2 mL) and the reaction mixture stirred at −78 C for 15 minutes. Diethylchlorophosphate (42 µL, 0.34 mmol) was added neat and the reaction mixture stirred at −78 C for 1 h. A precooled (−78 C) solution of TES-protected aldehyde XI(iv) (60 mg, 0.18 mmol) in THF (2 mL) was added via cannula. The reaction mixture was warmed to room temperature and allowed to stir overnight. The mixture was quenched with water (5 mL), extracted with CH$_2$Cl$_2$ (3×10 mL), dried over MgSO$_4$ and concentrated in vacuo. A mixture of geometrical isomers Xa(vi) (46 mg, 54%) was isolated by column chromatography with EtOAc/hexanes (1/15) as eluent. $^1$H NMR (400 MHz, CDCl$_3$) δ 6.05-6.17 (m, 1H), 4.02-4.03 (m, 1H), 2.10-2.61 (m, 2H), 1.74-1.95 (m, 3H), 1.53-1.68 (m, 3H), 1.41 (s, 9H), 1.93-1.41 (m, 4H), 1.02-1.15 (m, 2H), 0.84-0.99 (m, 14H), 0.52-0.58 (m, 6H).

(d) Preparation of (+)-E-VIIa(xi) and (+)-Z-VIIa(xii): To a solution of C24-fluoro-C25-sulfone Xa(vi) (44 mg, 0.093 mmol) in ethanol (2 mL) was added 49% aq. HF (0.15 mL) dropwise at room temperature. The mixture was stirred for 2 h, quenched with saturated aqueous sodium bicarbonate (5 mL), dried over MgSO$_4$ and concentrated to afford a crude product mixture of alcohols as a clear oil (33 mg). This mixture was dissolved in anhydrous CH$_2$Cl$_2$ (4 mL) and combined with celite (80 mg) and PDC (105 mg, 0.28 mmol). The reaction mixture was stirred overnight at room temperature, passed through a 2 cm pad of flash silica gel and washed with EtOAc. The filtrate was concentrated and the residue was subjected to column chromatography with EtOAc/hexanes (1/3) as eluent to afford 32 mg (96%) of the mixture of geometrical isomers (+)-E-VIIa(xi) and (+)-Z-VIIa(xii) as a colorless oil. $^1$H NMR (400 MHz, CDCl$_3$) δ 6.04-6.17 (m, 1H), 2.15-2.61 (m, 4H), 1.84-2.10 (m, 3H), 1.31-1.82 (m, 6H), 1.41 (s, 9H), 1.05 (d, J=6.8 Hz, 3H), 0.64 (s, 3H). HRMS ([M+Na]$^+$) calcd. 381.1870. Found 381.1880.

Example 13

Preparation of Compounds of the Formula Ia(xiii) and Ib(xiii)

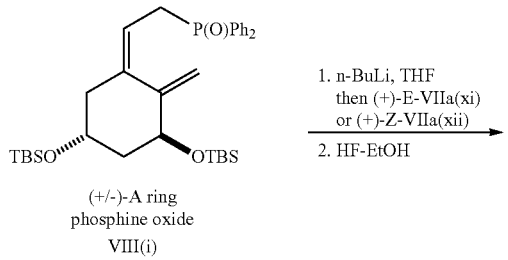

(+/−)-A ring phosphine oxide
VIII(i)

1. n-BuLi, THF then (+)-E-VIIa(xi) or (+)-Z-VIIa(xii)
2. HF-EtOH

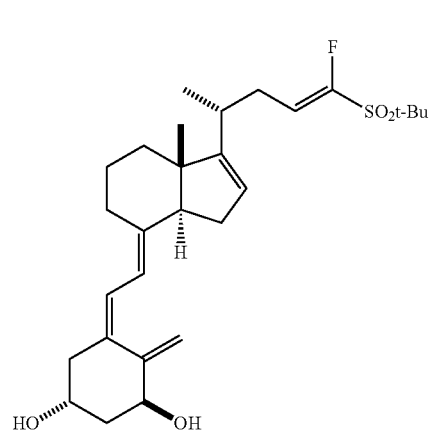

Ia(xiii) 16-E-23-E-diene-24F-25-SO$_2$-tBu, (1α,3β)-diol

+

-continued

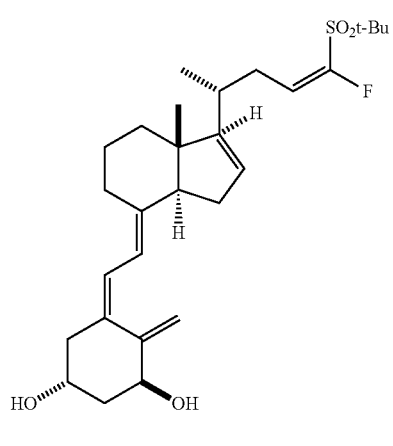

Ib(xiii) 16-E-23-Z-diene-24F-
25-SO₂-tBu, (1α,3β)-diol (a) Preparation of compounds of the Formula Ia(xiii) and Ib(xiii): A solution of 35 mg (0.060 mmol) of azeotropically dried (+)-phosphine oxide (from SynChem) in 1.5 mL of anhydrous THF was cooled to −78° C. and treated with 60 μL (0.60 mmol, 1.0 M in hexanes) of n-BuLi under argon atmosphere. The mixture turned deep reddish and was stirred for 15 min at −78° C. To the solution was added dropwise a precooled (−78° C.) solution of 15 mg (0.042 mmol) of the azeotropically dried C,D-ring ketone (+)-E-VIIa(xi) and (+)-Z-VIIa(xii) (E/Z=~2/1 by $^1$H NMR) in 1.5 mL of anhydrous THF via cannula. The reaction kept going until the reddish orange color faded to yellow (about 2 hr). The reaction was quenched by adding 1.0 mL of pH 7 buffer (commercially available from ALDRICH) at −78° C., then warmed to room temperature, extracted with EtOAc (20 mL×2), washed with brine, dried over MgSO₄, concentrated. The residue was subjected to column chromatography with EtOAc/hexanes (1/4) as eluent to afford 13 mg (43%) of the coupled product as a colorless oil.

The coupled product (13 mg, 0.018 mmol) was dissolved in 2 mL of anhydrous EtOH, and to the solution was added 100 mL of 49% aq. HF. The resulting mixture was stirred 2 hr at room temperature, then quenched with 5 mL of sat'd NaHCO₃ solution. The solution was stirred for 10 min, and then extracted with EtOAc (20 mL×3), washed with brine, dried over MgSO₄, concentrated. The residue was subjected to column chromatography with EtOAc as eluent to give 8 mg (90%) of the crude product of Ia(xiii) and Ib(xiii) (E/Z=~2/1 by $^1$H NMR) as a colorless oil. The crude product was purified by reverse-phase HPLC (C-18 semipreparative column, 49% H₂O in MeCN, 3 ml/min) to afford 0.3 mg of Ia(xiii) ($t_R$=94.6 min). The isomer Ib(xiii): was not purified completely by HPLC ($t_R$=96.7 min). Ia(xiii): $^1$H NMR (400 MHz, CDCl₃) δ 6.36 (d, J=11.6 Hz, 1H), 6.11 (ddd, J=32.8, 9.2, 6.8 Hz, 1H), 6.01 (d, J=11.2 Hz, 1H), 5.32 (s, 1H), 4.98 (s, 1H), 4.42 (m, 1H), 4.22 (m, 1H), 2.82 (m, 1H), 2.59 (m, 1H), 2.29-2.37 (m, 2H), 2.14-2.22 (m, 2H), 1.89-2.05 (m, 7H), 1.24-1.69 (m, 8H), 1.40 (s, 9H), 0.97 (d, J=6.4 Hz, 3H), 0.55 (s, 3H).

Example 14

Preparation of Compounds of the Formulae Ia(xiv) and Ia(xv)

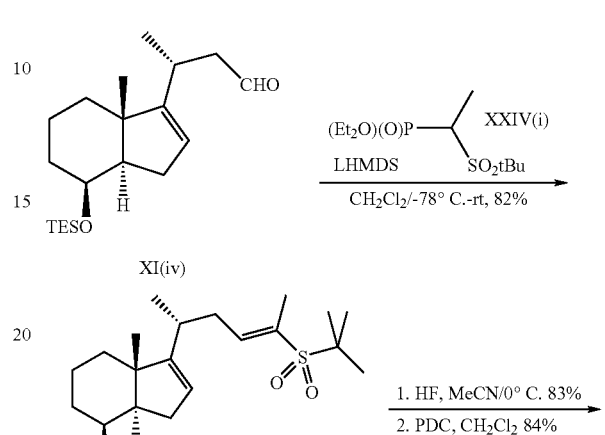

XI(iv)

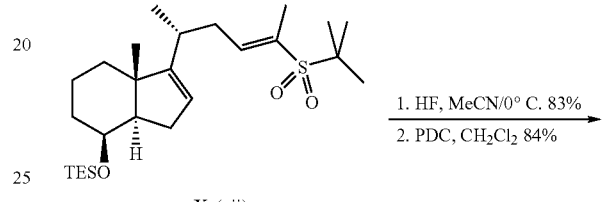

Xa(vii)

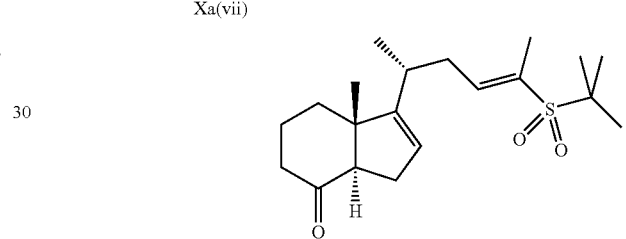

VIIa(xiii)

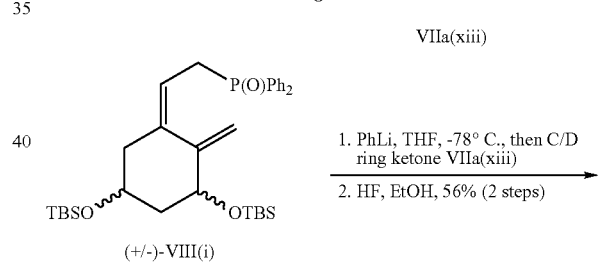

(+/−)-VIII(i)

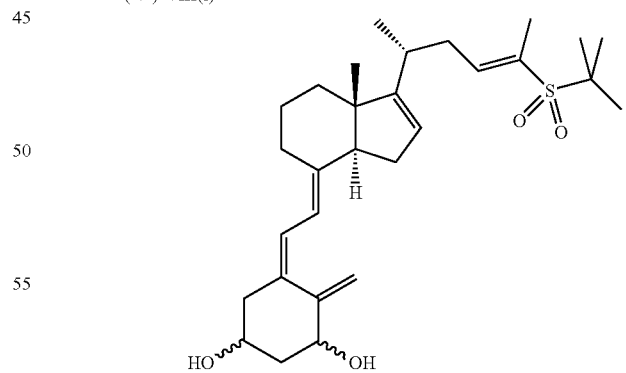

Ia(xiv) 16,23-diene-24-Me-25-SO2-TB1 (1α, 3β)
Ia(xv) 16,23-diene-24-Me-25-SO2-TB1 (1β, 3α)

(a) TES 16,23E-Diene-24-Methyl-25-Sulfone (+)-E-Xa (vii). To a solution of phophorane XXIV(i) (30 mg, 0.12 mmol) in 5 mL of THF was added 0.10 mL of lithium hexamethyldisilylazide (1.0 M solution in THF, 0.10 mmol) at −78 C. After 15 minutes at −78 C and warmed up to rt, THF was removed and dried in vacuo for 30 min. The residue was diluted with 5 mL of CH$_2$Cl$_2$ and TES protected aldehyde (+)-XI(iv) (20 mg, 0.060 mmol) in 1.0 mL of THF was added at rt. The reaction mixture was stirred at rt for 1 h and refluxed for 5 h. The reaction mixture was quenched with 10 mL of brine, extracted with ethyl acetate (50 mL×2), washed with brine, dried over anhydrous MgSO$_4$, concentrated in vacuo. The residue was purified by column chromatography (14% ethyl acetate/hexanes) to give the desired E isomer (23 mg, 82%) as a colorless oil. (+)-E-Xa(vii): [α]$^{25}_D$ +26.5 (c 2.8, CHCl$_3$).

(b) 16,23E-Diene-8-Keto-24-Methyl-25-Sulfone (+)-E-VIIa(xiii). To a solution of the sulfone (+)-E-Xa(vii) (29 mg, 0.062 mmol) in 10 mL of acetonitrile was added hydrofluoric acid (2% in H$_2$O, 0.10 mL, 0.10 mmol) at 0 C. After 6 h at room temperature, the reaction mixture was quenched with saturated NaHCO$_3$ solution (5 mL) and extracted with ethyl acetate (30 mL×3). The combined organic layers were washed with brine (30 mL), dried over MgSO$_4$ and concentrated. The crude product was purified by flash chromatography (50% ethyl acetate/hexanes) to give the alcohol (18 mg, 83%) as a colorless oil: [α]$^{25}_D$ +14.1 (c 1.8, CHCl$_3$). A flame-dried 25 mL flask was charged with 18 mg (0.051 mmol) of the C,D-ring alcohol, 7.0 mL of anhydrous CH$_2$Cl$_2$, 40 mg of oven-dried celite and 40 mg (0.11 mmol) of PDC. The reaction mixture was stirred for 5 h at rt and then passed through a 2 cm pad of flash silica gel and washed with EtOAc. The filtrate was concentrated and purified by column chromatography (33% ethyl acetate/hexanes) to give the desired C,D-ring ketone (+)-E-VIIa(xiii) (15 mg, 84%) as a colorless oil: [α]$^{25}_D$ +29.6 (c 1.1, CHCl$_3$).

(c) 16,23E-Diene-24-Methyl-25-Sulfone Analogs (+)-Ia(xiv) and (−)-Ia(xv). Azeotropically dried racemic phosphine oxide (±)-VIII(i) (46 mg, 0.079 mmol) was dissolved in 1.0 mL of anhydrous THF and cooled to −78 C under argon atmosphere. To this solution was added 57 μL (0.068 mmol) of phenyllithium (1.2 M solution in THF) dropwise. The mixture turned deep reddish orange and persisted. After stirring at −78 C for 30 minutes, a precooled (−78 C) solution of azeotropically dried C,D-ring ketone (+)-E-VIIa(xiii) (24 mg, 0.068 mmol) dissolved in 1.0 mL of anhydrous THF was added dropwise via cannula. The reaction kept going on until the reddish orange color faded to yellow. The reaction was quenched by adding 3.0 mL of a 1/1 mixture of 2 N sodium potassium tartrate and 2 N K$_2$CO$_3$ solution. The reaction mixture was allowed to warm to room temperature, extracted with EtOAc (50 mL×2), washed with brine, dried over anhydrous MgSO$_4$, filtered, concentrated in vacuo, and then purified by column chromatography (20% ethyl acetate/hexanes) to afford the coupled products (18 mg, 58%) as colorless oil.

The coupled products (18 mg, 0.025 mmol) were dissolved in 2.0 mL of anhydrous ethanol, and then 0.50 mL of HF (49% solution in water) was added and the resulted reaction mixture was stirred for 1 h at rt. The reaction was quenched with diluted NaHCO$_3$ solution and extracted with ethyl acetate (50 mL×2), washed with brine, dried over anhydrous MgSO$_4$, concentrated in vacuo and then purified by preparative TLC (ethyl acetate) to give a mixture of two diastereomers (11 mg, 96%) as colorless oil. The diastereomers were separated by reverse phase HPLC (C-18 semipreparative column, 45% MeCN/H$_2$O, 3.0 mL/min) to afford (+)-Ia(xiv) (4 mg, 19%, 1β, 3α, t$_R$ 67.2 min) as colorless oil and (−)-Ia(xv) (4 mg, 19%, 1β, 3α, t$_R$ 60.7 min) as colorless oil. (+)-Ia(xiv): [α]$^{25}_D$ +3.5 (c 0.40, CHCl$_3$); HRMS: calculated for C$_{29}$H$_{44}$O$_4$S [M+NH$_4$]: 506.3304. Found: 506.3310.(−)-Ia(xv): [α]$^{25}$D- 2.2 (c 0.40, CHCl$_3$); HRMS: calculated for C$_{29}$H$_{44}$O$_4$S [M+NH$_4$]: 506.3304 Found: 506.3300.

Examples for Compounds of Formula II

Example 15

Preparation of C/D Ring Ketones (+)-VIIa(xiii)

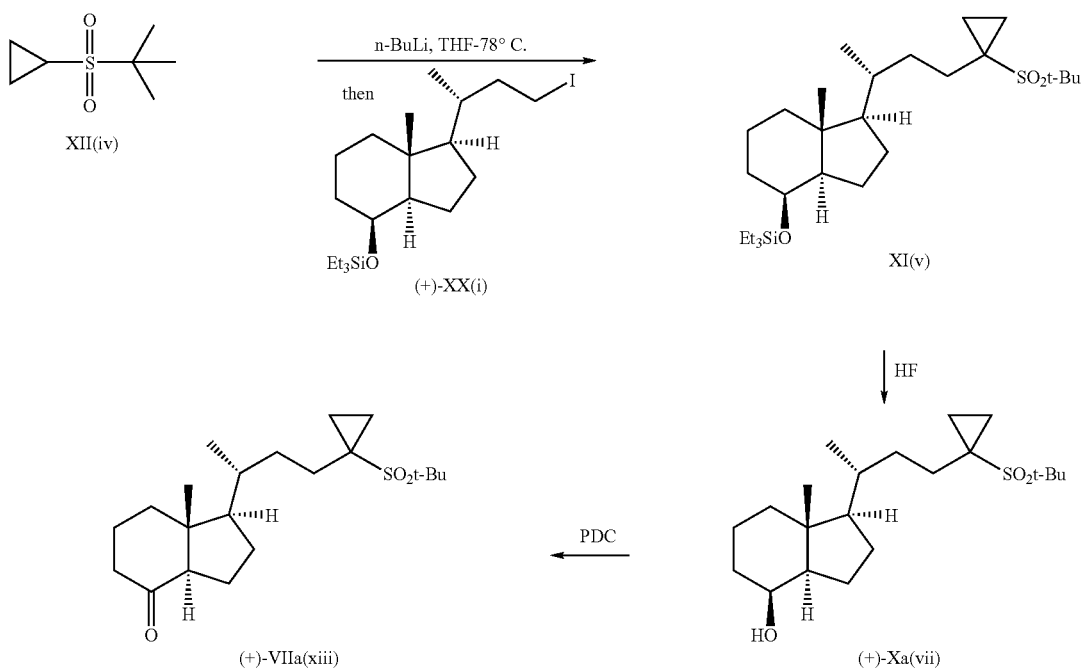

Sulfone XII(iv) may be prepared as described in Wang, Q. Ph.D. Thesis, Department of Chemistry, Krieger School Arts and Sciences, The Johns Hopkins University Baltimore, Md. 21218.

(a) Preparation of XI(v): A flame-dried 10 mL recovery flask equipped with a magnetic stir bar, a septum along with an Ar balloon was charged with sulfone XII(iv) (27 mg, 0.166 mmol) and dissolved in 0.8 mL freshly distilled THF and 0.08 mL HMPA. Then the flask was cooled down to −78° C. in an isopropanol/dry ice bath. To this solution was added 0.10 mL of n-BuLi (0.166 mmol, 1.6 M solution in hexanes) dropwise over several minutes during which time a pale yellow color developed. This mixture was allowed to stir at −780° C. for an additional 30 min. Meanwhile, a flame-dried 10 mL pear shaped flask equipped with a septum along with an Ar balloon was charged with iodide (+)-XX(i) (25 mg, 0.055 mmol) which was dissolved in 0.5 mL freshly distilled THF and cooled down to −78° C. in an isopropanol/dry ice bath. The solution of iodide (+)-XX(i) was transferred into the flask containing the lithiated sulfone at −78° C. via cannula over several minutes. After the addition was complete, the mixture was gradually warmed up to room temperature and then stirred for about 8 hours. TLC showed the complete consumption of starting material. The reaction was quenched by addition of 5 mL distilled water and then rinsed into a separatory funnel with ethyl acetate. The mixture was extracted with ethyl acetate (3×25 mL). The combined extracts were washed with water (1×25 mL), and brine solution (1×25 mL), dried over $Na_2SO_4$ and filtered. The filtrate was concentrated in vacuo to give the crude product that was purified by flash column chromatography eluted with 10% ethyl acetate in hexanes affording 20 mg of (+)-XI(v) as a viscous oil in 74% yield. Data for (+)-XI(v): $[\alpha]^{24}_D$=+38.2 (c=1.1, $CHCl_3$) $^1H$ NMR ($CDCl_3$, 400 MHz): d 4.03-4.02 (m, 1H), 2.02-1.90 (m, 2H), 1.86-1.72 (m, 3H), 1.68-1.31 (m, 9H), 1.47 (s, 9H), 1.26-1.00 (m, 5H), 0.94 (t, 9H, J=8.0 Hz), 0.88 (s, 3H), 0.87 (d, 3H, J=7.6 Hz), 0.80-0.77 (m, 2H), 0.55 (q, 6H, J=8.0). $^{13}C$ NMR ($CDCl_3$, 100 MHz): d 69.30, 62.04, 56.33, 53.00, 42.10, 40.72, 38.54, 35.45, 34.57, 31.99, 29.44, 27.32, 25.17, 22.94, 18.54, 17.64, 13.45, 11.18, 11.08, 6.94, 4.91. IR (Thin Film) 2949 (s), 2875 (s), 1458 (m), 1373 (m), 1290 (br, s), 1164 (w), 1109 (s), 1020 (br, m), 806 (w) $cm^1$. HRMS: calculated for $C_{27}H_{52}O_3SSiNa^+$ [M+Na]: 507.3298. Found: 507.3289.

(b) Preparation of (+)-Xa(vii): A 5 mL argon purged polypropylene vial equipped with a magnetic stir bar with a cap was carged with (+)-XI(v) (20 mg, 0.041 mmol) and dissolved in 2.0 mL anhydrous acetonitrile to give ca. 0.02 M solution. To this well-stirred solution was added 0.16 mL of HF (4 mmol, 49% aqueous solution) via syringe at room temperature and the mixture was then allowed to stir at room temperature in the dark for 3 hours. TLC showed the completion of the reaction. This reaction mixture was diluted with ether (25 mL) and saturated solution of $NaHCO_3$ was added until no more carbon dioxide was liberated. The reaction mixture was then rinsed into a separatory funnel with ethyl acetate and was extracted with ethyl acetate (4×25 mL). The combined extracts were washed with water (1×25 mL), and brine solution (1×25 mL), dried over $Na_2SO_4$ and filtered. The filtrate was concentrated in vacuo to give the crude product that was purified by column chromatography eluted with 50% ethyl acetate in hexanes affording 14 mg of alcohol (+)-Xa(vii) in 92% yield. Data for (+)-Xa(vii): $[\alpha]^{24}_D$=+29.2 (c=0.75, $CHCl_3$). $^1H$ NMR ($CDCl_3$, 400 MHz): d 4.07-4.06 (m, 1H), 1.98-1.94 (m, 2H), 1.89-1.71 (m, 4H), 1.63-1.37 (m, 7H), 1.47 (s, 9H), 1.34-1.02 (m, 7H), 0.91 (s, 3H), 0.88 (d, 3H, J=6.4 Hz), 0.79-0.76 (m, 2H). $^{13}C$ NMR ($CDCl_3$, 100 MHz): d 62.27, 62.08, 56.18, 52.51, 41.82, 40.31, 38.49, 35.45, 33.50, 31.99, 29.54, 27.18, 25.16, 22.45, 18.44, 17.38, 13.35, 11.21, 11.17. IR (Thin Film) 3528 (br, m), 2937 (s), 2872 (s), 1471 (m), 1366 (w), 1282 (s), 1106 (s), 1038 (m), 942 (w), 804 (w) $cm^{-1}$. HRMS: calculated for $C_{21}H_{38}O_3SNa^+$ [M+Na]: 393.2434. Found: 393.2438.

(c) Preparation of (+)-VIIa(xiii): A flame-dried 10-mL recovery flask equipped with a magnetic stir bar, a septum along with an Ar balloon was charged with (+)-Xa(vi) (14 mg, 0.038 mmol) dissolved in 3 mL freshly distilled $CH_2Cl_2$. Then, to this solution were added PDC (30 mg, 0.079 mmol) and 19 mg of oven-dried Celite in one portion at room temperature. The resulting mixture was allowed to stir at room temperature for about 12 hours. TLC showed the complete consumption of starting material. The mixture was directly purified by column chromatography eluted with 25% ethyl acetate affording 12.1 mg of ketone (+)-VIIa(xiii) in 87% yield. Data for (+)-VIIa(xiii): $^1H$ NMR ($CDCl_3$, 400 MHz): d 2.42 (dd, 1H, J=7.2, 11.6 Hz), 2.29-2.15 (m, 2H), 2.09-2.05 (m, 1H), 2.02-1.84 (m, 4H), 1.77-1.16 (m, 2H), 1.46 (s, 9H), 0.92 (d, 3H, J=6.4 Hz), 0.78-0.75 (m, 2H), 0.61 (s, 3H). $^{13}C$ NMR ($CDCl_3$, 100 MHz): d 211.86, 62.14, 61.86, 56.25, 49.81, 40.89, 38.90, 38.39, 35.73, 32.15, 29.81, 27.55, 25.17, 23.98, 19.03, 18.60, 12.42, 11.33, 11.31. IR (Thin Film) 2957 (s), 2872 (m), 1711 (s), 1468 (sh, m), 1379 (w), 1284 (br, s), 1107 (w), 834 9 (w) $cm^{-1}$. HRMS: calculated for $C_{21}H_{36}O_3SNa^+$ [M+Na]: 391.2277. Found: 391.2249.

Example 16

Preparation of Compound of the Formula IIa

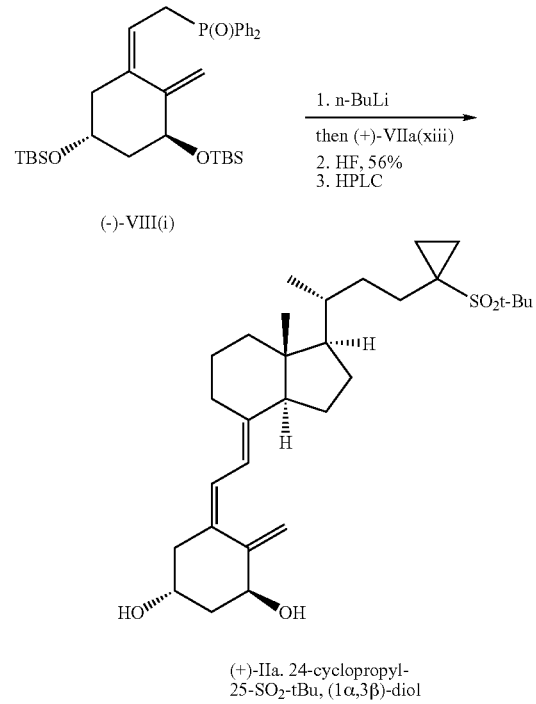

(+)-IIa. 24-cyclopropyl-
25-$SO_2$-tBu, (1α,3β)-diol

Chiral phosphine oxide (−)-VIII(i) and C, D-ring ketone (+)-VIIa(xiii), each was separately azeotropically dried with anhydrous benzene (4×5 mL) on a rotary evaporator and held under vacuum (ca. 0.1 mmHg) for at least 48 hours prior to use.

A flame-dried 10 mL recovery flask equipped with a magnetic stir bar, a septum along with an Ar balloon was charged with azeotropically dried chiral phosphine oxide (−)-VIII(i) (29 mg, 0.0497 mmol) which was dissolved in 0.5 mL freshly distilled THF. The flask was cooled down to −78° C. in an isopropanol/dry ice bath. To this solution was added n-BuLi (43 μL, 0.052 mmol, 1.2 M solution in hexanes) dropwise over several minutes during which time a deep red color developed and persisted. This mixture was allowed to stir at −78° C. for an additional 10 min. Meanwhile, a flame-dried 10 mL recovery flask equipped with a magnetic stir bar, a septum along with an Ar balloon was charged with C, D-ring ketone (+)-VIIa(xiii) (11 mg, 0.03 mmol) dissolved in 0.5 mL freshly distilled THF and cooled down to −78° C. in an isopropanol/dry ice bath. The solution of C, D-ring ketone was transferred dropwise into the flask containing the phosphine oxide anion at −78° C. via cannula over several minutes. After the addition was complete, the deep red color persisted and the mixture was allowed to stir at 78° C. for ca. 1 hour during which time it was visually checked. Upon observation of the light yellow color, the reaction was quenched at −78° C. by addition of 1 mL of pH 7 buffer and allowed to come to room temperature. The mixture was then rinsed into a separatory funnel with ethyl acetate and extracted with ethyl acetate (3×25 mL). The combined extracts were washed with water (1×25 mL) and brine solution (1×25 mL), dried over $Na_2SO_4$ and filtered. The filtrate was concentrated in vacuo to give the crude product which was purified by column chromatography eluted with 50% ethyl acetate in hexanes in the presence of 1% triethylamine to afford the coupled product.

This coupled product (8 mg, 0.011 mmol) was charged into a 5 mL argon purged polypropylene vial equipped with a magnetic stir bar along with a cap and dissolved in 0.5 mL anhydrous acetonitrile to give ca. 0.02 M solution. To this well-stirred solution was added 45 mL of HF (1.1 mmol, 49% aqueous solution) via syringe at room temperature and the mixture was then allowed to stir at room temperature in the dark for 3 hours. TLC showed the completion of the reaction. This reaction mixture was diluted with ether (25 mL) and saturated solution of $NaHCO_3$ was added until no more carbon dioxide was liberated. The reaction mixture was then rinsed into a separatory funnel with ethyl acetate and was extracted with ethyl acetate (4×25 mL). The combined extracts were washed with water (1×25 mL), and brine solution (1×25 mL), dried over $Na_2SO_4$ and filtered. The filtrate was concentrated in vacuo to give the crude product that was purified by column chromatography eluted with 99% ethyl acetate in the presence of 1% triethylamine affording 3.1 mg (+)-IIa. This was then further purified by HPLC using a Chiralcel OJ column (Semipreparative (1×25 cm), flow rate=2.0 mL/min) eluted with 10% ethanol in hexanes to afford 0.8 mg (+)-IIa in 22% yield. The retention time for (+)-7 is 32.2 min. Data for (+)-IIa: $[\alpha]^{24}_D$=+7.0 (c=0.07, $CHCl_3$) $^1$H NMR ($CDCl_3$, 400 MHz): δ 6.38 (d, 1H, J=11.2 Hz), 6.01 (d, 1H, J=11.2 Hz), 5.33 (m, 1H), 5.00 (m, 1H), 4.47-4.42 (m, 1H), 4.25-4.21 (m, 1H), 2.83 (dd, 1H, J=6.6 Hz, J=13.2 Hz), 2.60 (dd, 1H, J=6.6 Hz, J=13.2 Hz) 2.31 (dd, 1H, J=6.4 Hz, J=14.0 Hz) 2.05-1.84 (m, 7H), 1.80-1.65 (m, 6H), 1.48 (s, 9H), 1.31-1.11 (m, 9H), 0.91 (d, 3H, J=6.4 Hz), 0.81-0.78 (m, 2H), 0.53 (s, 3H). $^{13}$C NMR ($CDCl_3$, 100 MHz): δ 143.00, 141.60, 132.93, 124.94, 117.10, 111.84, 71.27, 70.83, 66.84, 56.25, 56.05, 45.86, 42.82, 40.42, 36.22, 32.15, 29.51, 29.02, 27.62, 25.19, 23.52, 22.23, 18.75, 11.97. 11.28, 11.15. IR: 3553 (m, br), 2931 (s), 2872 (s), 1466 (m), 1349 (w), 1278 (s), 1102 (s), 796 (m) cm$^{-1}$. HRMS: calculated for $C_{30}H_{48}O_4SNa^+$ [M+Na]: 527.3165. Found: 527.3189. UV (MeOH) $\lambda_{max}$ 263 nm (e 2751).

Example 17

Preparation of tert-Butyl cyclobutyl sulfone (XX(i))

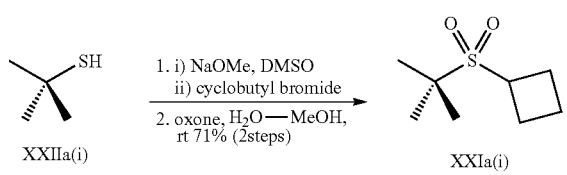

To a solution of tert-butyl thiol XXIIa(i) (1.51 mL, 13.3 mmol) in DMSO (7.2 mL) was added NaOMe (800 mg, 14.7 mmol) and cyclobutylbromide (0.63 mL, 6.47 mmol) at rt. The resulting cloudy solution was heated to 90° C. and stirred for 5 hr at the same temperature. The reaction was quenched with water, extracted by ether, dried over $MgSO_4$. The organic phase was concentrated to afford the crude sulfide. This sulfide was directly used for the next step. To a solution of the above crude sulfide in MeOH (30 mL) was added a solution of oxone (6.1 g, 9.82 mmol) in water (30 mL) at 0° C. The resulting cloudy solution was warmed to rt, then stirred for 5 hrs. The reaction mixture was concentrated using rotary evaporator, diluted with water, extracted with EtOAc. The organic layer was separated, dried over $MgSO_4$, concentrated to afford the crude sulfone(XX(i)) which was recrystallized in hexanes to give 810 mg (71% for 2 steps) of tert-butyl cyclobutyl sulfone. $^1$H NMR (400 MHz, $CDCl_3$) δ 3.92-4.01 (m, 1H), 2.62-2.73 (m, 2H), 2.20-2.28 (m, 2H), 1.94-2.14 (m, 2H), 1.36 (s, 9H).

Example 18

Preparation of the Compound of Formula IIb and IIc

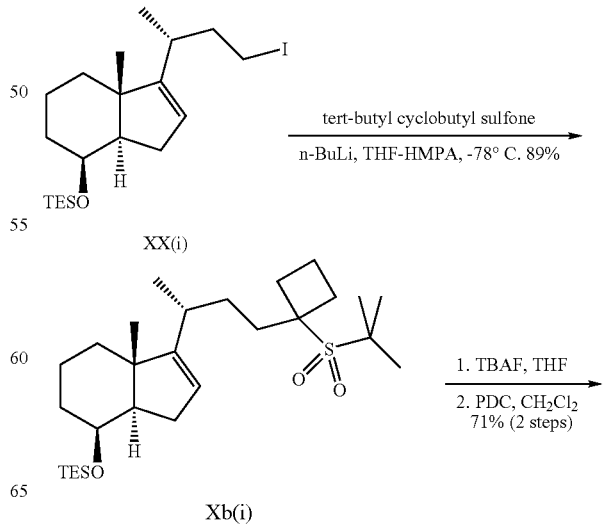

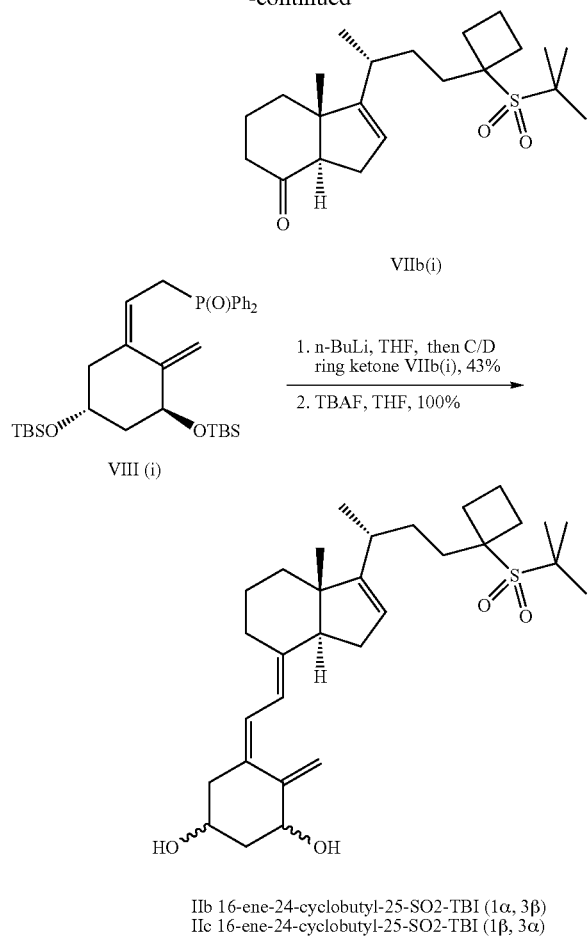

IIb 16-ene-24-cyclobutyl-25-SO2-TBI (1α, 3β)
IIc 16-ene-24-cyclobutyl-25-SO2-TBI (1β, 3α)

(a) C24-cyclobutyl C25-sulfone (+)-Xb(i): To a solution of tert-butyl cyclobutyl sulfone XXIa(i) (86.4 mg, 0.49 mmol) in THF (4 mL) at −78° C. was added 0.22 mL of n-BuLi (2.23M in Hex, 0.49 mmol). After 15 min stirring, 0.4 mL of HMPA was added at −78° C. After additional 15 min stirring, a pre-cooled (−78° C.) solution of iodide (−)-XX(i) (76 mg, 0.169 mmol) in THF (1 mL) was added at the same temperature. The resulting solution was slowly warmed to rt. The reaction was quenched with pH 7 buffer, extracted with ether. The organic layer was dried over MgSO$_4$, filtered, concentrated to afford a crude mixture which was purified by flash chromatography (EtOAc:Hex=1:7 to 1:4) to afford 75.1 mg (89%) of C24-cyclobutyl C25-sulfone (+)-Xb(i). R$_f$ 0.53 (1:4-EtOAc:Hex); [α]$_D^{26}$ +12.2° (c 1.11, CHCl$_3$); $^1$H NMR (400 MHz, CDCl$_3$) δ 5.32 (m, 1H), 4.13 (m, 1H), 2.91-3.00 (m, 2H), 2.27 (m, 1H), 1.80-2.08 (m, 10H), 1.62-1.78 (m, 4H), 1.34-1.52 (m, 3H), 1.39 (s, 9H), 1.06 (d, J=6.8 Hz, 3H), 1.01 (s, 3H), 0.96 (t, J=8.0 Hz, 9H), 0.57 (q, J=8.0 Hz, 6H); $^{13}$C NMR (100 MHz, CDCl$_3$) δ 159.5, 120.2, 68.9, 67.4, 62.1, 55.1, 46.6, 35.7, 34.9, 33.0, 32.3, 30.9, 30.7, 28.2, 27.7, 25.1, 22.8, 18.9, 18.0, 16.0, 6.9, 4.9; IR (thin film) 1284, 1112, 1082, 1029 cm$^{-1}$; HRMS [M+Na] calcd 519.3304 for C$_{28}$H$_{52}$O$_3$SSi. Found 519.3295.

(b) C24-cyclobutyl C/D ring ketone (+)-VIIb(i): C24-cyclobutyl C25-sulfone (+)-Xb(i) (73.2 mg, 0.147 mmol) in THF (3 mL) was desilylated using 0.45 mL of TBAF (1 M solution in THF, 0.45 mmol) to afford the C24-cyclobutyl C8 alcohol. Without further purification, this alcohol was submitted to PDC oxidation. A solution of the alcohol in CH$_2$Cl$_2$ (10 mL) was treated with PDC (126 mg, 0.33 mmol). After stirring for 2 days, the reaction mixture was filtered and purified by flash chromatography (EtOAc:Hex=1:2) to give 39.6 mg (71% for 2 steps) of C/D ring ketone VIIb(i) R$_f$ 0.35 (1:2-EtOAc:Hex); [α]$_D^{26}$ +8.81° (c 1.04, CHCl$_3$); $^1$H NMR (400 MHz, CDCl$_3$) δ 5.35 (m, 1H), 2.93-3.01 (m, 2H), 2.88 (dd, J=6.8, 10.8 Hz, 1H), 2.47 (ddt, J=1.2, 10.8, 16 Hz, 1H), 2.28-2.32 (m, 2H), 1.75-2.16 (m, 1H), 1.39 (s, 9H), 1.13 (d, J=6.8 Hz, 3H), 0.82 (s, 3H); $^{13}$C NMR (100 MHz, CDCl$_3$) δ 210.7, 157.2, 120.7, 67.2, 63.0, 62.1, 53.8, 40.4, 34.3, 33.3, 33.0, 30.8, 28.2, 27.8, 27.0, 25.0, 23.9, 22.2, 17.3, 15.9; IR (thin film) 1716, 1374, 1279 cm$^{-1}$; HRMS [M+Na] calcd 403.2283 for C$_{22}$H$_{36}$O$_3$S. Found 403.2278.

(c) HWY-16-ene-24-cyclobutyl-25-SO2-TB ((+)-IIb and (−)-IIc): To a solution of A-ring phosphine oxide VIII(i) (75 mg, 0.129 mmol) in THF (2 mL) was added 0.0561 mL of n-BuLi (2.23 M in Hexane, 0.125 mmol) at −78° C., then the reddish solution was stirred for 10 min at the same temperature. A precooled (−78° C.) solution of C/D ring ketone VIIb (i) (38.3 mg, 0.101 mmol) in THF (1 mL) was added to the above solution at −78° C. via cannula. The resulting reddish orange solution was stirred for 4.5 hrs at −78° C. The reaction was quenched with 3 mL of a 1:1 mixture of 2N Na—K tartrate and 2N K$_2$CO$_3$, then warmed to rt, extracted with EtOAc, washed with brine, dried over MgSO4, filtered, concentrated in vacuo, and purified by flash chromatography (EtOAc:Hex=1:7 to 1:4 to 1:1) to give 32.5 mg (43%) of a mixture of bis TBS protected IIb and IIc. A solution of the above mixture of bis TBS protected IIb and IIc (30.1 mg, 0.0404 mmol) in THF (4 mL) was treated with 0.20 mL of TBAF (1 M in THF, 0.20 mmol). The crude mixture was purified by flash chromatography (EtOAc:Hex=3:1 to only EtOAc) to afford 21.4 mg (100%) of a mixture of diastereomers. The diasereomers were then purified by reversed-phase HPLC (C18 semipreparative column, 50% MeCN/water, 3 mL/min, 254 nm) to give 1.07 mg (5%) of 16-ene-24-cyclobutyl-25-SO2-TB1 ((+)-IIb) and 0.52 mg (2%) of 16-ene-24-cyclobutyl-25-SO2-TB2 ((−)-IIc). (+)-IIb: R$_f$ 0.47 (EtOAc); [α]$_D^{26}$ +13.40 (c 0.11, CHCl$_3$); $^1$H NMR (400 MHz, CDCl$_3$) δ 6.38 (d, J=11.2, 1H), 6.11 (d, J=11.6, 1H), 5.34-5.36 (m, 2H), 5.02 (m, 1H), 4.45 (m, 1H), 4.24 (m, 1H), 2.93-2.99 (m, 2H), 2.83 (m, 1H), 2.61 (m, 1H), 2.30-2.41 (m, 2H), 2.23 (m, 1H), 2.12 (m, 1H), 1.75-2.08 (m, 12H), 1.50-1.75 (m, 6H), 1.40 (s, 9H), 1.10 (d, J=6.8 Hz, 3H), 0.70 (s, 3H); $^{13}$C NMR (100 MHz, CDCl$_3$) δ 159.0, 147.6, 142.2, 133.2, 124.8, 120.6, 117.0, 111.8, 70.8, 67.4, 66.8, 62.2, 58.4, 50.0, 45.2, 42.8, 35.2, 33.4, 33.1, 30.9, 29.4, 28.7, 28.2, 27.9, 25.1, 23.5, 22.1, 17.0, 16.0; IR (thin film) 3446, 1276, 1108 cm$^{-1}$; UV (MeOH) l$_{max}$ 261 nm (e 5755). (−)-IIc: R$_f$ 0.47 (EtOAc); [α]$_D^{26}$ −4.2° (c 0.052, CHCl$_3$); $^1$H NMR (400 MHz, CDCl$_3$) δ 6.39 (d, J=11.6, 1H), 6.11 (d, J=11.2, 1H), 5.36 (m, 1H), 5.33 (m, 1H), 5.02 (m, 1H), 4.45 (m, 1H), 4.22 (m, 1H), 2.93-3.00 (m, 2H), 2.82 (m, 1H), 2.62 (m, 1H), 1.72-2.42 (m, 16H), 1.52-1.70 (m, 6H), 1.40 (s, 9H), 1.10 (d, J=6.8 Hz, 3H), 0.69 (s, 3H); $^{13}$C NMR (100 MHz, CDCl$_3$) δ 159.0, 147.2, 142.2, 133.0, 124.8, 120.8, 117.0, 112.6, 71.3, 67.4, 66.8, 62.1, 58.4, 50.0, 45.4, 42.8, 35.2, 33.4, 33.0, 30.9, 29.4, 28.7, 28.2, 27.9, 25.1, 23.5, 22.1, 17.0, 16.0; IR (thin film) 3446, 1275, 1107 cm$^{-1}$; UV (MeOH) l$_{max}$ 262 nm (e 4892).

Examples for Compounds of Formula IV

Example 19

Preparation of tert-Butyl isopropyl sulfone (XXIc(i))

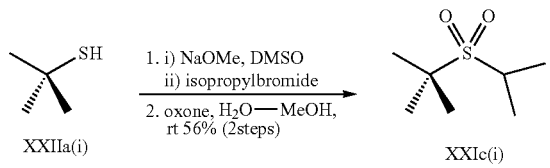

To a solution of tert-butyl thiol XXIIa(i) (1.50 mL, 13.2 mmol) in DMSO (8 mL) was added NaOMe (802 mg, 14.7 mmol) and isopropylbromide (0.62 mL, 6.54 mmol) at rt. The resulting cloudy solution was heated to 90° C. and stirred for 5 hrs at the same temperature. The reaction was quenched with water, extracted by ether, dried over $MgSO_4$. The organic phase was concentrated to afford the crude sulfide. This sulfide was directly used for the next step. To a solution of the above crude sulfide in MeOH (30 mL) was added a solution of oxone (6.8 g, 11.0 mmol) in water (30 mL) at 0° C. The resulting cloudy solution was warmed to rt, then stirred for 5 hrs. The reaction mixture was concentrated using rotary evaporator, diluted with water, extracted with EtOAc. The organic layer was separated, dried over $MgSO_4$, concentrated to afford the crude sulfone which was purified by flash chromatography (EtOAc:Hex=1:3 to 1:2) to give 594 mg (56% for 2 steps) of tert-butyl isopropyl sulfone XXIc(i)). $R_f$ 0.36 (1:2-EtOAc:Hex); $^1$H NMR (400 MHz, $CDCl_3$) δ 3.40 (m, 1H), 1.44 (s, 9H), 1.42 (d, J=6.8 Hz, 6H).

Example 20

Preparation of the Compound of Formula Va

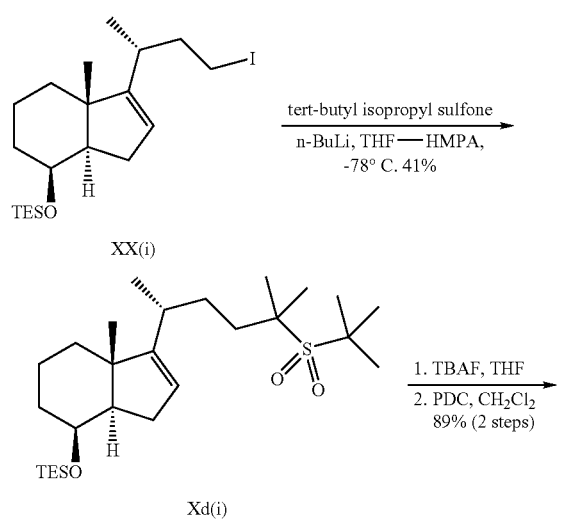

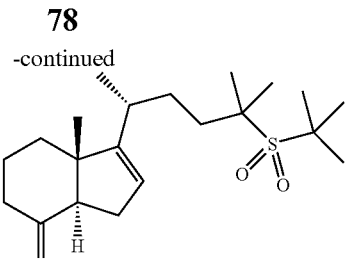

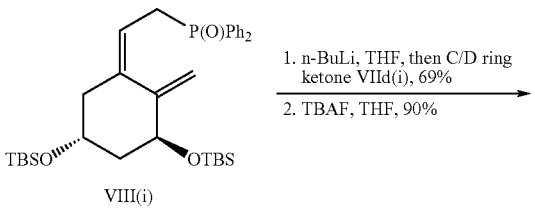

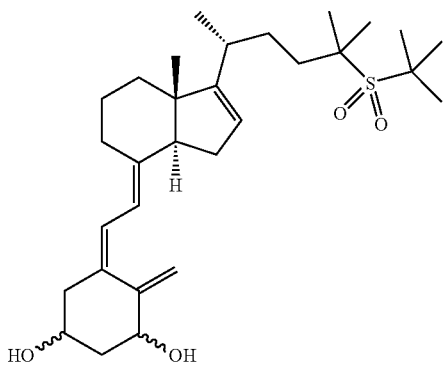

IVa 16-ene-24-dimethyl-25-SO2-TB1 (1α, 3β)
IVb 16-ene-24-dimethyl-25-SO2-TB1 (1β, 3α)

(a) C24-dimethyl C25-sulfone (+)Xd(i): To a solution of tert-butyl isopropyl sulfone XXIc(i)(ii) (101.8 mg, 0.62 mmol) in THF (3 mL) at −78° C. was added 0.276 mL of n-BuLi (2.23M in Hex, 0.615 mmol). After 15 min stirring, 0.3 mL of HMPA was added at −78° C. After additional 15 min stirring, a precooled solution of iodide (−)-XX(i) (138.3 mg, 0.308 mmol) in THF (1 mL) was added at the same temperature. The resulting solution was slowly warmed to rt. The reaction was quenched with pH 7 buffer, extracted with ether. The organic layer was dried over $MgSO_4$, filtered, concentrated to too afford a crude mixture which was purified by flash chromatography (EtOAc:Hex=1:7 to 1:4) to afford 61.3 mg (41%) of C24-dimethyl C25-sulfone (+)-Xd(i). $R_f$ 0.5 (1:4-EtOAc:Hex); $[\alpha]_D^{26}$ +8.89° (c 1.03, $CHCl_3$); $^1$H NMR (400 MHz, $CDCl_3$) δ 5.26 (m, 1H), 4.12 (m, 1H), 2.25 (m, 1H), 2.01 (m, 1H), 1.76-1.93 (m, 4H), 1.61-1.70 (m, 3H), 1.38-1.60 (m, 5H), 1.48 (s, 9H), 1.46 (s, 3H), 1.45 (s, 3H), 1.01 (d, J=6.8 Hz, 3H), 0.99 (s, 3H), 0.95 (t, J=8.0 Hz, 9H), 0.57 (q, J=8.0 Hz, 6H); $^{13}$C NMR (100 MHz, $CDCl_3$) δ 159.5, 119.9, 69.0, 68.9, 65.3, 55.0, 46.6, 35.7, 35.2, 34.9, 32.1, 30.7, 30.4, 26.1, 22.7, 22.6, 22.4, 18.8, 18.0, 6.9, 4.9; IR (thin film) 1458, 1279, 1093 $cm^{-1}$; HRMS [M+Na] calcd 507.3304 for $C_{27}H_{52}O_3SSi$. Found 507.3292.

(b) C24-dimethyl C/D ring ketone (+)-VIId(i): C24-dimethyl C25-sulfone Xd(i) (90.4 mg, 0.186 mmol) in THF (3 mL) was desilylated using 0.56 mL of TBAF (1 M solution in THF, 0.56 mmol) to afford the C24 dimethyl C8 alcohol. Without further purification, this alcohol was submitted to PDC oxidation. A solution of the alcohol in $CH_2Cl_2$ (10 mL) was treated with PDC (330 mg, 0.86 mmol). After stirring for 2 days, the reaction mixture was filtered and purified by flash chromatography (EtOAc:Hex=3:7 to 1:2) to give 60.8 mg (89% for 2 steps) of C24-dimethyl-C/D ring ketone (+)-VIId (i). $R_f$ 0.18 (1:3-EtOAc:Hex); $[\alpha]_D^{26}$ +23.60 (c 1.04, $CHCl_3$); $^1H$ NMR (400 MHz, $CDCl_3$) δ 5.30 (m, 1H), 2.86 (dd, J=6.4, 10.8 Hz, 1H), 2.46 (ddt, J=1.6, 10.8, 16 Hz, 1H), 2.28-2.32 (m, 2H), 1.95-2.16 (m, 4H), 1.75-1.91 (m, 4H), 1.53-1.64 (m, 2H), 1.48 (s, 9H), 1.462 (s, 3H), 1.460 (s, 3H), 1.09 (d, J=6.8 Hz, 3H), 0.80 (s, 3H); $^{13}C$ NMR (100 MHz, $CDCl_3$) δ 210.8, 157.3, 120.5, 68.7, 65.4, 63.0, 53.8, 40.5, 35.4, 34.3, 33.2, 30.3, 27.1, 26.1, 24.0, 22.8, 22.6, 22.1, 17.2; IR (thin film) 1716, 1275, 1093 $cm^{-1}$.

(c) 16-ene-24-dimethyl-25-SO2-TB ((−)-IVa and (−)-IVb): To a solution of A-ring phosphine oxide VIII(i) (95.4 mg, 0.164 mmol) in THF (1.5 mL) was added 0.075 mL of n-BuLi (2.12 M in Hexane, 0.159 mmol) at −78° C., then the reddish solution was stirred for 10 min at the same temperature. A precooled (−78° C.) solution of C/D ring ketone VIId(i) (33.1 mg, 0.0898 mmol) in THF (1.5 mL) was added to the above solution at −78° C. via cannula. The resulting reddish orange solution was stirred for 4.5 hrs at −78° C. The reaction was quenched with 2 mL of pH 7 buffer, then warmed to rt, extracted with EtOAc, washed with brine, dried over $MgSO_4$, filtered, concentrated in vacuo, and purified by flash chromatography (EtOAc:Hex=1:7 to 1:4 to 1:1) to give 45.7 mg (69%) of a mixture of bis TBS protected IVa and IVb. A solution of the above mixture of bis TBS protected IVa and IVb (45.7 mg, 0.0623 mmol) in THF (5 mL) was treated with 0.31 mL of TBAF (1 M in THF, 0.31 mmol). The crude mixture was purified by flash chromatography (EtOAc: Hex=3:1 to only EtOAc) to afford 28.2 mg (90%) of a mixture of diastereomers. The diastereomers were then purified by reversed-phase HPLC (C18 semipreparative column, 50% MeCN/water, 3.5 mL/min, 254 nm) to give 10.1 mg (32%) of 16-ene-24-dimethyl-25-SO2-TB1 ((−)-IVa) and 5.0 mg (16%) of HWY-16-ene-24-dimethyl-25-SO2-TB2 ((−)-IVb). (−)-IVa: $R_f$ 0.47 (EtOAc); $[\alpha]_D^{26}$ −11.7° (c 0.28, $CHCl_3$); $^1H$ NMR (400 MHz, $CDCl_3$) δ 6.37 (d, J=11.2, 1H), 6.10 (d, J=11.6, 1H), 5.34 (m, 1H), 5.30 (m, 1H), 5.01 (m, 1H), 4.43 (m, 1H), 4.24 (m, 1H), 2.82 (m, 1H), 2.60 (m, 1H), 2.30-2.39 (m, 2H), 2.21 (m, 1H), 1.96-2.10 (m, 3H), 1.70-1.92 (m, 6H), 1.45-1.70 (m, 6H), 1.48 (s, 9H), 1.45 (s, 6H), 1.05 (d, J=6.8 Hz, 3H), 0.67 (s, 3H); $^{13}C$ NMR (100 MHz, $CDCl_3$) δ 159.0, 147.6, 142.3, 133.1, 124.8, 120.6, 116.9, 111.8, 70.8, 68.9, 66.8, 65.4, 58.3, 50.0, 45.2, 42.8, 35.23, 35.19, 33.2, 30.3, 29.4, 28.8, 26.2, 23.6, 22.66, 22.58, 22.1, 16.9; IR (thin film) 3426, 1271, 1090 $cm^{-1}$; UV (MeOH) $1_{max}$ 261 nm (e 12363).
(−)-IVb: $R_f$ 0.47 (EtOAc); $[\alpha]_D^{26}$ −27.4° (c 0.23, $CHCl_3$); $^1H$ NMR (400 MHz, $CDCl_3$) δ 6.39 (d, J=11.2, 1H), 6.10 (d, J=11.2, 1H), 5.33 (m, 1H), 5.30 (m, 1H), 5.01 (m, 1H), 4.46 (m, 1H), 4.23 (m, 1H), 2.82 (m, 1H), 2.62 (m, 1H), 2.19-2.40 (m, 3H), 1.72-2.10 (m, 9H), 1.45-1.60 (m, 6H), 1.49 (s, 9H), 1.46 (s, 6H), 1.06 (d, J=6.8 Hz, 3H), 0.67 (s, 3H); $^{13}C$ NMR (100 MHz, $CDCl_3$) δ 159.0, 147.1, 142.4, 132.9, 124.9, 120.6, 116.9, 112.7, 71.4, 68.9, 66.8, 65.4, 58.3, 50.0, 45.5, 42.8, 35.21, 35.17, 33.2, 30.3, 29.4, 28.7, 26.2, 23.6, 22.65, 22.57, 22.1, 16.9; IR (thin film) 3427, 1272, 1091 $cm^{-1}$; UV (MeOH) $1_{max}$ 262 nm (e 36969).

Examples for Compounds of Formula V

Example 21

Preparation of Compounds Va, Vb, Vc and Vd

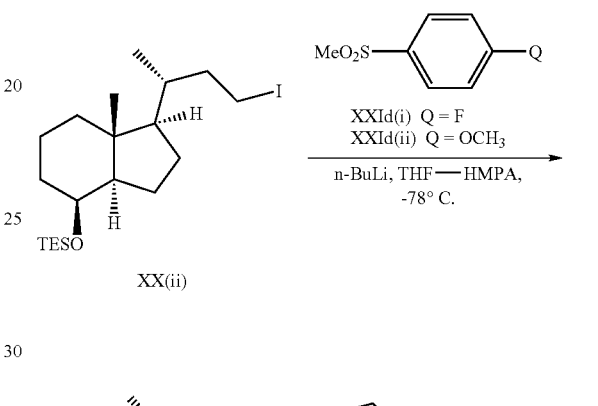

XXId(i) Q = F
XXId(ii) Q = $OCH_3$ n-BuLi, THF — HMPA, −78° C.

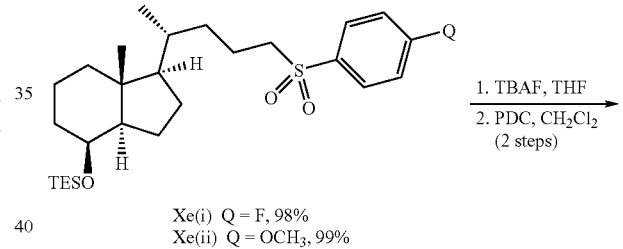

Xe(i) Q = F, 98%
Xe(ii) Q = $OCH_3$, 99%

1. TBAF, THF
2. PDC, $CH_2Cl_2$
(2 steps)

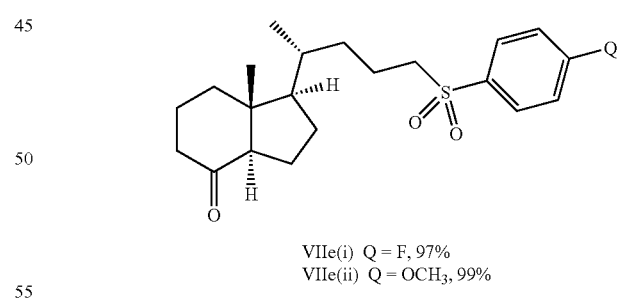

VIIe(i) Q = F, 97%
VIIe(ii) Q = $OCH_3$, 99%

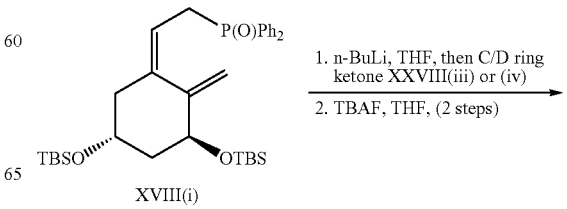

XVIII(i)

1. n-BuLi, THF, then C/D ring ketone XXVIII(iii) or (iv)
2. TBAF, THF, (2 steps)

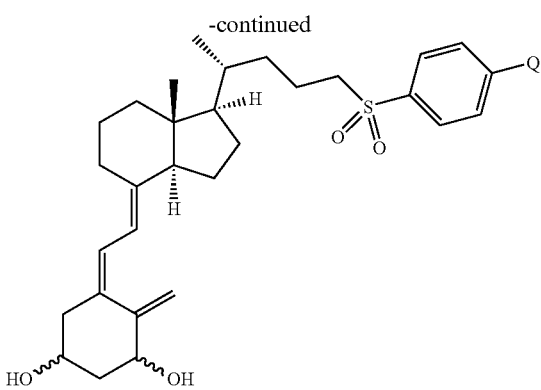

(+)-Va 25-SO2-PFP  Q = F (1α, 3β) 44%
(−)-Vb 25-SO2-PFP  Q = F (1β, 3α) 21%
(+)-Vc 25-SO2-PMP  Q = OCH₃ (1α, 3β) 36%
(−)-Vd 25-SO2-PMP  Q = OCH₃ (1β, 3α) 15%

(a) C25-p-Fluorophenyl sulfone (+)-Xe(i): To a solution of 1-methanesulfonyl-4-fluorobenzene XXId(i) (58 mg, 0.333 mmol) in THF (2.25 mL) at −78° C. was added 0.213 mL of n-BuLi (1.56 M in Hex, 0.333 mmol). After 15 min stirring, 0.2 mL of HMPA was added at −78° C. After additional 15 min stirring, a precooled solution of iodide (+)-XX(ii) (50 mg, 0.111 mmol) in THF (1 mL) was added at the same temperature. The resulting solution was slowly warmed to rt. The reaction was quenched with pH 7 buffer, extracted with ether. The organic layer was dried over MgSO₄, filtered, concentrated to afford a crude mixture which was purified by flash chromatography (EtOAc:Hex=1:19 to 1:4) to afford gave 54 mg (98%) of C24-phenyl sulfone (+)-Xe(i) as a colorless oil. $[\alpha]_D^{25}$ +40.8 (c 31.8, CHCl₃); ¹H NMR (400 MHz, CDCl₃, TMS) δ 7.97-7.89 (m, 2H), 7.29-7.21 (m, 2H), 4.04-3.98 (m, 1H), 3.12-2.94 (m, 2H), 1.95-1.86 (dt, J=12, 2.2 Hz, 1H), 0.94 (t, J=8.0 Hz, 9H), 0.87 (s, 3H), 0.85 (d, J=6.8 Hz, 3H), 0.54 (q, J=8.0 Hz, 6H); ¹³C NMR (100 MHz, CDCl₃) δ 165.7 (d, J=255.2 Hz), 135.3, 130.9 (d, J=9.9 Hz), 116.5 (d, J=22.8 Hz), 69.3, 56.9, 56.3, 53.0, 42.1, 40.7, 34.9, 34.5, 34.4, 29.7, 27.3, 22.9, 19.4, 18.3, 17.6, 13.5, 6.9, 4.9; ¹⁹F NMR (375 MHz, CDCl₃, CFCl₃) 6-104.2 (m); IR (neat) 2931, 2872, 1590, 1490, 1318, 1290, 1250, 1143, 1079, 1022 cm⁻¹; HRMS: calcd for C₂₇H₄₅FO₃SSi+Na, 519.2740. Found 519.2739.

(b) C25-p-Methoxyphenyl sulfone (+)-Xe(ii). To a solution of 1-methanesulfonyl-4-methoxybenzene XXId(ii) (207 mg, 1.11 mmol) in THF (2.25 mL) at −78° C. was added 0.213 mL of n-BuLi (1.57 M in Hex, 0.333 mmol). After 15 min stirring, 0.2 mL of HMPA was added at −78° C. After additional 15 min stirring, a precooled solution of iodide (+)-XX(ii) (100 mg, 0.222 mmol) in THF (1 mL) was added at the same temperature. The resulting solution was slowly warmed to rt. The reaction was quenched with pH 7 buffer, extracted with ether. The organic layer was dried over MgSO₄, filtered, concentrated to afford a crude mixture which was purified by flash chromatography (EtOAc:Hex=1:19 to 1:4) to afford gave 112 mg (99%) of C24-phenyl sulfone (+)-Xe(ii) as a white solid: mp 71-72° C.; $[\alpha]_D^{25}$+36.3 (c 5.0, CHCl₃); ¹H NMR (400 MHz, CDCl₃) δ 7.84-7.78 (dt, J=9.5, 2.8, 2.2 Hz, 2H), 7.03-6.98 (dt, J=9.5, 2.8, 2.2 Hz, 2H), 4.02-3.97 (m, 1H), 3.87 (s, 3H), 3.08-2.91 (m, 2H), 1.94-1.85 (dt, J=12, 2.6 Hz, 1H), 0.92 (t, J=8.0 Hz, 9H), 0.85 (s, 3H), 0.83 (d, J=6.8 Hz, 3H), 0.53 (q, J=8.0 Hz, 6H); ¹³C NMR (100 MHz, CDCl₃) δ 163.6, 130.8, 130.1, 114.3, 69.2, 57.0, 56.3, 55.6, 52.9, 42.1, 40.6, 34.9, 34.5, 34.3, 27.2, 22.9, 19.4, 18.3, 17.6, 13.4, 6.9, 4.9; IR (neat) 2950, 2875, 1596, 1498, 1319, 1296, 1261, 1144, 1089, 1025 cm⁻¹; Anal. Calcd for C₂₈H₄₈O₄SSi: C, 66.09; H, 9.51. Found: C, 66.35; H, 9.51.

(c) C25-p-F-Phenyl sulfone C/D ring ketone (+)-VIIe(i). To a solution of C24-p-F-phenyl sulfone (+)-Xe(i) (54 mg, 0.109 mmol) in THF (~0.7 M) was added 0.435 mL of TBAF (1 M solution in THF, 0.435 mmol). The reaction mixture was stirred for 18 h and concentrated under reduced pressure to a brown syrup. This brown syrup was then dissolved in CH₂Cl₂ and treated with pyridinium dichromate (PDC, 123 mg, 0.327 mmol), and Celite (123 mg) for 12 h. The contents of the flask were then passed through a 1' plug of silica gel, rinsed with EtOAc, concentrated, and purified by flash chromatography (35 to 40% EtOAc in Hex) to afford 40 mg (97%) of (+)-VIIe (i) as a colorless oil: $[\alpha]_D^{25}$ +11.4 (c 42.8, CHCl₃); ¹H NMR (400 MHz, CDCl₃, TMS) δ 7.94-7.85 (m, 2H), 7.25-7.18 (m, 2H), 3.10-2.92 (m, 2H), 2.46-2.34 (dd, J=11, 7.2 Hz, 1H), 0.88 (d, J=6.0 Hz, 3H), 0.56 (s, 3H); ¹³C NMR (100 MHz, CDCl₃) δ 211.7, 165.6 (d, J=254.4 Hz), 135.2 (d, J=3.0 Hz), 130.7 (d, J=9.8 Hz), 116.5 (d, J=22.8 Hz), 61.7, 56.6, 56.0, 49.7, 40.8, 38.7, 35.1, 34.1, 27.3, 23.8, 19.2, 18.9, 18.3, 12.3; ¹⁹F NMR (375 MHz, CDCl₃, CFCl₃) δ −104.0 (m); IR (neat) 2943, 2872, 1708, 1584, 1490, 1314, 1284, 1143, 1079 cm⁻¹; HRMS: calcd for C₂₁H₁₃FO₃S+Na, 403.1719. Found 403.1718.

(d) C25-p-Methoxyphenyl sulfone C/D ring ketone (+)-VIIe(ii): To a solution of C25-p-methoxyphenyl sulfone (+)-Xe(ii) (107 mg, 0.210 mmol) in THF (~0.7 M) was added 0.84 mL of TBAF (1 M solution in THF, 0.84 mmol). The reaction mixture was stirred for 18 h and concentrated under reduced pressure to a brown syrup. This brown syrup was then dissolved in CH₂Cl₂ and treated with pyridinium dichromate (PDC, 237 mg, 0.63 mmol), and Celite (237 mg) for 12 h. The contents of the flask were then passed through a 1' plug of silica gel, rinsed with EtOAc, concentrated, and purified by flash chromatography (35 to 40% EtOAc in Hex) to afford 82 mg (99%) of (+)-VIIe(ii) as a colorless oil: $[\alpha]_D^{25}$ +10.0 (c 9.0, CHCl₃); ¹H NMR (400 MHz, CDCl₃) δ 7.82-7.74 (dt, J=9.5, 2.8, 2.2 Hz, 2H), 7.03-6.98 (dt, J=9.5, 2.8, 2.2 Hz, 2H), 3.84 (s, 3H), 3.08-2.91 (m, 2H), 1.94-1.85 (dt, J=12, 2.6 Hz, 1H), 0.92 (t, J=8.0 Hz, 9H), 0.85 (s, 3H), 0.83 (d, J=6.8 Hz, 3H), 0.53 (q, J=8.0 Hz, 6H); ¹³C NMR (100 MHz, CDCl₃) δ 211.7, 163.5, 130.6, 130.0, 114.3, 61.7, 56.7, 56.1, 55.6, 49.7, 40.8, 38.7, 35.1, 34.2, 27.3, 23.8, 19.3, 18.9, 18.3, 12.3; IR (neat) 2955, 2873, 1710, 1595, 1497, 1318, 1294, 1260, 1140, 1089, 1024 cm⁻¹; HRMS: calcd for C₂₂H₃₂O₄S+Na, 415.1919. Found 415.1913.

(e) 25-SO2—PFP Va and Vb A solution of n-BuLi (89 μL, 0.129 mmol, 1.44 M in hexanes) was added dropwise to a solution of (±)-A-ring phosphine oxide VIII(i) (75 mg, 0.129 mmol) in THF (1.3 mL) at −78° C. The resulting deep red solution was stirred for 1 h, at which time a precooled (−78° C.) solution of C/D ring ketone (+)-VIIe(i) (25 mg, 0.064 mmol) in THF (1.2 mL) was added dropwise via cannula. The resulting solution was stirred at −78° C. in the dark for approximately 3 h, then slowly warmed to −40° C. over 2 h. The reaction mixture was quenched with water (1 mL), warmed to rt, extracted with ether, washed with brine, dried over MgSO₄, filtered, concentrated, and purified by silica gel column chromatography (20 to 50% EtOAc in Hex) to afford the coupled products as a clear oil. This oil was immediately dissolved in THF (5.0 mL) and treated with 0.322 mL of TBAF (1M in THF, 0.322 mmol) in the dark for 16 h. Concentration of the reaction mixture and column chromatography (EtOAc) yielded a mixture of diastereomers. HPLC separation (CHIRALCEL® OJ semipreparative column, 25% EtOH/hexanes, 3 mL/min) gave analogs (+)-Va (15 mg, 44%, 1α,3β, $R_f$ 29.9 min) and (+)-Vb (7 mg, 21%, 1β,3α, $R_f$ 23.1 min). (+)-Va (1α,3β): $[α]_D^{25}$ +24.2 (c 1.2, CHCl$_3$); $^1$H NMR (400 MHz, CDCl$_3$, TMS) δ 7.97-7.89 (m, 2H), 7.32-7.20 (m, 2H), 6.37 (d, J=11.2 Hz, 1H), 6.00 (d, J=11.2 Hz, 1H), 5.32 (m, 1H), 4.99 (m, 1H), 4.50-4.38 (m, 1H), 4.30-4.16 (m, 1H), 3.13-2.96 (m, 2H), 2.87-2.77 (dd, J=12.0, 4.0 Hz, 1H), 2.64-2.54 (dd, J=13.3, 3.4 Hz, 1H), 2.36-2.26 (dd, J=13.3, 6.4 Hz, 1H), 0.90 (d, J=6.4, 3H), 0.52 (s, 3H); $^{13}$C NMR (100 MHz, CDCl$_3$) δ 165.8 (d, J=255.1 Hz), 147.6, 142.8, 135.3 (d, J=3.0 Hz), 133.0, 130.9 (d, J=9.4 Hz), 124.8, 117.1, 116.6 (d, J=22.5 Hz), 111.8, 70.8, 66.8, 56.8, 56.2, 56.1, 45.8, 45.2, 42.8, 40.4, 35.8, 34.4, 29.0, 27.6, 23.5, 22.2, 19.4, 18.5, 11.9; $^{19}$F NMR (375 MHz, CDCl$_3$, CFCl$_3$) δ −104.1 (m); IR (neat) 3636-3142, 2952, 2924, 2871, 2853, 1724, 1591, 1493, 1464, 1289, 1237, 1145, 1086, 840, 755 cm$^{-1}$; UV (MeOH) $λ_{max}$ 214 (ε 41,431), 265 nm (ε 20,447); HRMS: calcd for C$_{30}$H$_{21}$FO$_4$S+Na, 539.2607. Found 539.2631. (+)-Vb (1β, 3α): $[α]_D^{25}$ +11.5 (c 1.2, CHCl$_3$); $^1$H NMR (400 MHz, CDCl$_3$, TMS) δ 7.97-7.89 (m, 2H), 7.32-7.20 (m, 2H), 6.38 (d, J=11.2 Hz, 1H), 6.00 (d, J=11.2 Hz, 1H), 5.31 (m, 1H), 4.99 (m, 1H), 4.50-4.38 (m, 1H), 4.30-4.16 (m, 1H), 3.14-2.96 (m, 2H), 2.88-2.75 (dd, J=12.4, 4.0 Hz, 1H), 2.66-2.54 (dd, J=13.4, 3.8 Hz, 1H), 2.36-2.24 (dd, J=13.2, 6.4 Hz, 1H), 0.90 (d, J=6.4, 3H), 0.52 (s, 3H); $^{13}$C NMR (100 MHz, CDCl$_3$) δ 165.8 (d, J=255.1 Hz), 147.2, 142.8, 135.3 (d, J=3.0 Hz), 132.9, 130.8 (d, J=9.1 Hz), 124.9, 117.1, 116.6 (d, J=22.1 Hz), 112.5, 71.3, 66.7, 56.8, 56.2, 56.1, 45.8, 45.4, 42.8, 40.3, 35.8, 34.4, 28.9, 27.6, 23.5, 22.2, 19.4, 18.5, 11.9; $^9$F NMR (375 MHz, CDCl$_3$, CFCl$_3$) δ −104.1 (m); IR (neat) 3636-3142, 2925, 2872, 2852, 1724, 1591, 1492, 1464, 1318, 1288, 1235, 1144, 1085, 1055, 840, 756 cm$^{-1}$; UV (MeOH) $λ_{max}$ 214 (ε 28,949), 265 nm (ε 15,871); HRMS: calcd for C$_{30}$H$_{21}$FO$_4$S+Na, 539.2607. Found 539.2611.

(f) 25-SO2-PMP Vc and Vd: A solution of n-BuLi (0.089 mL, 0.129 mmol, 1.44 M in hexanes) was added dropwise to a solution of (±)-A-ring phosphine oxide VIII(i) (75 mg, 0.129 mmol) in THF (1.3 mL) at −78° C. The resulting deep red solution was stirred for 1 h, at which time a precooled (−78° C.) solution of C/D ring ketone (+)-VIIe(ii) (25 mg, 0.064 mmol) in THF (1.2 mL) was added dropwise via cannula. The resulting solution was stirred at −78° C. in the dark for approximately 3 h, then slowly warmed to −40° C. over 2 h. The reaction mixture was quenched with water (1 mL), warmed to rt, extracted with ether, washed with brine, dried over MgSO$_4$, filtered, concentrated, and purified by silica gel column chromatography (20 to 50% EtOAc in Hex) to afford the coupled products as a clear oil. This oil was immediately dissolved in THF (5.0 mL) and treated with 0.322 mL of TBAF (1M in THF, 0.322 mmol) in the dark for 16 h. Concentration of the reaction mixture and column chromatography (EtOAc) yielded a mixture of diastereomers. Reverse phase HPLC separation (LUNA™ semipreparative column, 52% MeCN/H$_2$O, 3 mL/min) afforded analogs (+)-Vc (12 mg, 36%, 1α,3β, $R_f$ 79.1 min) and (+)-Vd (5 mg, 15%, 1β,3α, $R_f$ 75.8 min). (+)-Vc (1α,3β): $[α]_D^{25}$ +24.4 (c 5.0, CHCl$_3$); $^1$H NMR (400 MHz, CDCl$_3$) δ 7.88-7.78 (dt, J=8.8, 2.8, 2.0 Hz, 2H), 7.03-6.98 (dt, J=8.8, 2.8, 2.0 Hz, 2H), 6.37 (d, J=11.2 Hz, 1H), 6.00 (d, J=11.2 Hz, 1H), 5.32 (m, 1H), 4.99 (m, 1H), 4.47-4.38 (m, 1H), 4.27-4.17 (m, 1H), 3.87 (s, 3H), 3.10-2.92 (m, 2H), 2.87-2.77 (dd, J=12.0, 4.0 Hz, 1H), 2.64-2.54 (dd, J=14.0, 3.6 Hz, 1H), 2.36-2.26 (dd, J=13.6, 6.4 Hz, 1H), 0.88 (d, J=6.4, 3H), 0.51 (s, 3H); $^{13}$C NMR (100 MHz, CDCl$_3$) 163.6, 147.6, 142.9, 133.0, 130.8, 130.2, 124.9, 117.1, 114.4, 111.8, 70.8, 66.8, 57.0, 56.2, 56.1, 55.7, 45.2, 42.8, 40.4, 38.5, 34.5, 29.0, 27.6, 23.5, 22.2, 19.5, 18.5, 12.0; IR (neat) 3754-3054, 3019, 2949, 2925, 2866, 1596, 1497, 1318, 1292, 1261, 1140, 1089, 1055, 1026, 835, 804, 756 cm$^{-1}$; UV (MeOH) $λ_{max}$ 241 (ε 26,000), 262 nm (ε 15,107); HRMS: calcd for C$_{31}$H$_{24}$O$_5$S+Na, 551.2807. Found 551.2825. (+)-Vd(1β,3α): $[α]_D^{25}$ +4.3 (c 2.0, CHCl$_3$); $^1$H NMR (400 MHz, CDCl$_3$) δ 7.86-7.79 (dt, J=8.8, 2.8, 2.0 Hz, 2H), 7.05-6.98 (dt, J=8.8, 2.8, 2.0 Hz, 2H), 6.38 (d, J=11.2 Hz, 1H), 5.99 (d, J=11.2 Hz, 1H), 5.31 (m, 1H), 4.99 (m, 1H), 4.47-4.38 (m, 1H), 4.27-4.17 (m, 1H), 3.89 (s, 3H), 3.10-2.92 (m, 2H), 2.87-2.77 (dd, J=12.2, 3.8 Hz, 1H), 2.64-2.54 (dd, J=13.0, 3.8 Hz, 1H), 2.36-2.26 (dd, J=13.0, 7.4 Hz, 1H), 0.89 (d, J=6.4, 3H), 0.51 (s, 3H); $^{13}$C NMR (100 MHz, CDCl$_3$) δ 163.6, 147.2, 142.9, 132.8, 130.8, 130.2, 124.9, 117.1, 114.4, 112.5, 71.3, 66.8, 57.0, 56.2, 56.1, 55.7, 45.8, 45.4, 42.8, 40.4, 35.8, 34.5, 29.0, 27.6, 23.5, 22.2, 19.5, 18.5, 12.0; IR (neat) 3742-3048, 3016, 2922, 2863, 1651, 1595, 1577, 1497, 1455, 1319, 1294, 1260, 1216, 1139, 1088, 1056, 1026, 853, 804, 758 cm$^{-1}$; UV (MeOH) $λ_{max}$ 242 (ε 22,887), 263 nm (ε 13,090); HRMS: calcd for C$_{31}$H$_{24}$O$_5$S+Na, 551.2807. Found 551.2791.

Example 22

CYP24 Enzyme Assay (Induced HPK1A-ras Cells)

(i) Material and Reagents:
  1,25(OH)$_2$D$_3$ 10$^{-5}$ M (Sigma, St. Louis, Mo.);
  Preparation of 10$^{-5}$ M working solution is as follows:
    Dissolve 1 mg of 1,25(OH)$_2$D$_3$ into 480 µl of isopropanol to make 5×10$^{-3}$ M stock solution. Store at −70° C. until needed. Aliquot 1 µl of 1,25(OH)$_2$D$_3$ 5×10$^{-3}$ M stock solution to 499 µl of isopropanol to make 1,25(OH)$_2$D$_3$ 10$^{-5}$ working solution. Store at −20° C. until needed.
  [$^3$H]-1,25(OH)$_2$D$_3$ 16,000 cpml/µL, 8 µM (Perkin Elmer, Boston, Mass.)
  HPK1A-ras cells (obtained from Dr. Glenville Jones, Queens University, Kingston, Ontario, Canada)
  48-well plate
  Methanol
  Dichloromethane
  Saturated KCl: KCl 30 g, H$_2$O 400 ml
  1,2-Dianilinoethane (DPPD)
  Ketoconazole (Sigma, St. Louis, Mo.)
(ii) Procedure:
  1. Induction of HPK1A-ras cells (The day before assay)
    When the HPK1A-ras cells were 80-90% confluent, added 1 µL 10$^{-5}$ M 1,25(OH)$_2$D$_3$ to 1 mL medium in the plate (final concentration is 10$^{-8}$ M).
  2. Preparation of cell suspension
    After 18 to 20 hours induction, removed the medium and washed the cell twice with PBS. Then tripsinized the cells from plate, centrifuged (2,000 rpm, 5 min) and suspended cells pellet in DMEM medium+1% BSA. Counted the cells and adjusted cells density to 250,000/ 150 µL, added 150 µL cell suspension to each well in 48-well plate (including 3 wells as a no cell control, and 3 well cells without drug or inhibitor as controls).
  3. Added 25 mL ketoconazole (final concentration 10$^{-5}$ M, 10$^{-6}$ M, 10$^{-7}$ M, 10$^{-8}$ M) or drugs (final concentration 10$^{-6}$ M, 10$^{-7}$ M, 10$^{-8}$ M, 10$^{-9}$ M) into each designated well. Kept the plate in 37° C. for 10 min.
  4. Preparation of substrate
    For each ml required, added 972 µl of DMEM+1% BSA medium, 20 µl of $^3$H-1,25(OH)$_2$D$_3$, and 8 µl of 100 nM DPPD to a tube and vortexed.
  5. Incubation
    Added 25 µL substrate to each well, incubated the plate at 37° C. for 2 hour.

Added 25 μL substrate to counting plate (2 well) as a total count.
6. Lipid extraction and counting
   Added 500 μL methanol to each well to stop the reaction, transferred them to tube.
   Added 250 μL dichloromethane and vortex.
   Added 250 mL dichloromethane and 250 μL saturated KCl, and vortex.
   Centrifuged at 4000 rpm for 5 min.
   Transferred 100 μL of aqueous phase (upper phase) to counting plastic counting plate. Added 600 mL of scintillation fluid to each well. Counted the plate in scintillation counter.
7. Calculation enzyme activity
   CPM of cell control after subtraction of CPM of non-cell control (NCC) was as 100% enzyme activity.

Enzyme activity=(CPM in test compounds well−CPM in NCC well)/(CPM in Cell control−CPM in NCC well)*100%

| | Dilution of Ketoconazole Stock $10^{-2}$ M | | |
|---|---|---|---|
| Concentration (final) | From previous step (μL) | DMEM + 1% BSA (μL) | Concentration (actual) |
| $10^{-5}$ M | 4 | 496 | $8 \times 10^{-5}$ M |
| $10^{-6}$ M | 12.5 | 112.5 | $8 \times 10^{-6}$ M |
| $10^{-7}$ M | 12.5 | 112.5 | $8 \times 10^{-7}$ M |
| $10^{-8}$ M | 12.5 | 112.5 | $8 \times 10^{-8}$ M |

| | Dilution of test compounds Stock $10^{-3}$ M | | |
|---|---|---|---|
| Concentration (final) | From previous step (μL) | DMEM + 1% BSA (μL) | Concentration (actual) |
| $10^{-6}$ M | 4 | 496 | $8 \times 10^{-6}$ M |
| $10^{-7}$ M | 12.5 | 112.5 | $8 \times 10^{-7}$ M |
| $10^{-8}$ M | 12.5 | 112.5 | $8 \times 10^{-8}$ M |
| $10^{-9}$ M | 12.5 | 112.5 | $8 \times 10^{-9}$ M |

(iii) Results: Compounds of the invention showed and $IC_{50}$ for CYP24 in this assay in the range of 20-750 nM indicating that the compounds of the invention are modulators of this enzyme.
(iv) References:
Ray S, Ray R, Holick M. Metabolism of $^3$H-1alpha, 25-dihydroxy vitamin $D_3$ in the cultured human keratinocytes (1995) 59:117-122
Dilworth F J, Scott I, Green A, Strugnell S, Guo Y D, Roberts E A, Kremer R, Calverley, M J, Makin H L J, Jones G. Different mechanisms of hydroxylation site selection by liver and kidney cytochrome P450 species (CYP27 and CYP24) involved in Vitamin D metabolism. (1995) J Biochem 270(28):16766-16774.

Example 23

CYP24 Enzyme Assay (Using Stable Cell Line—V79-CYP24 cells)

(i) Material and reagents
1α,25(OH)$_2$D$_3$ 1 mM reconstituted in isopropanol
Substrates (1 mM) reconstituted in isopropanol
V79-CYP24 cells
DMEM media supplemented with hygromycin and 10% fetal bovine serum
DMEM+1% BSA media
DPPD
48-well plate
methanol
dichloromethane
saturated KCl: KCl 30 g, H$_2$O 400 ml
ketoconazole
(ii) Procedure:
1. Preparation of cell suspension
   On the day of the assay, washed the monolayer of V79-CYP24 cells once with 1×PBS buffer and then trypsinize for 5 min at room temperature (approx. 22° C.). Added 1×PBS. Collected cells into tube, centrifuged cells (500×g, 5 min) and resuspended in DMEM+1% BSA media. Counted cells and adjusted density to 250,000 cells/150 μl (1.67 million/1 mL).
2. Cell plating
   Added 150 μl of cell suspension to appropriately labelled wells of a 48-well plate. Incubated plate for 30 minutes at 37° C. in a humidified atmosphere containing 5% CO$_2$ for adherence of cells to wells.
3. Compound addition
   Added 25 μl of inhibitor ($10^{-6}$ to $10^{-9}$ M) and then after 10 min added 25 μl of substrate [$^3$H-1β]-1α,25(OH)$_2$D$_3$ (20 nM) for 2 hours at 37° C. in a humidified atmosphere containing 5% CO$_2$. Both inhibitor and substrate were prepared in DMEM with 1% BSA media in the absence and presence of 100 μM DPPD.
4. Lipid extraction and counting
   Added 500 μl of methanol to stop the reaction. Transferred to tube. Added 250 μl of dichloromethane and vortexed. Added 250 μl of dichloromethane and 250 μl of saturated KCL and vortexed. Centrifuged at 4000 rpm for 5 min. Triplicate 100 μl aliquots of aqueous fraction were mixed with 600 μl of scintillation fluid and the radioactivity was measured using a scintillation counter. All values were normalized for background.
(iii) Results.
   Compounds of the invention showed and $IC_{50}$ for CYP24 in this assay in the range of 20-1000 nM indicating that the compounds of the invention are modulators of this enzyme.
(iv) Reference.
1. PCT Patent Application Serial No. PCT/CA03/00620

Example 24

CYP27A1 Enzyme Assay (A) Procedure:
   As described in:
Dilworth F J, Black S M, Guo Y D, Miller W L, Jones G. Construction of a P450c27 fusion enzyme: a useful tool for analysis of vitamin D$_3$ 25-hydroxylase (1996) Biochem J 320:267-271
Sawada N, Sakaki T, Ohta M, Inouye K. Metabolism of vitamin D (3) by human CYP27A1 (2000) Biochem Biophys Res Commun 273(3):977-84
(B) Results:
   Compounds of the invention showed an $IC_{50}$ for CYP27A1 in this assay in the range of 1000->10,000 nM indicating that the compounds of the invention are selective modulators for CYP24 over CYP27A 1.

Example 25

VDR Binding Assay

VDR Binding Assay
(i) Reagent and Materials
1. VDR 9.4 pmol/μl (human, recombinant, Biomol).
2. [$^3$H]-1,25(OH)$_2$D$_3$ in ethanol
3. 1,25(OH)$_2$D$_3$ in ethanol
4. TEK$_{300}$

| | |
|---|---|
| Tris-HCl | 50 mM |
| EDTA | 1.5 mM |
| KCl | 300 mM |
| Adjust pH to 7.4 (25 C.) | |

5. TEDK$_{300}$
   TEK$_{300}$
   DTT (dithiothreitol) 10 mM (MW 154.24)
6. Tris buffer
   22.50 g Tris-HCl
   500 ml H$_2$O
   13.25 g Tris-base
   500 ml H$_2$O
   Kept in 4 C
7. Dextran-T70 (Mol 70,000) Pharmacia
8. Charcoal (carbon decolorizing neutral, norit) Fisher Scientific
9. Gelatin (G-2625 Sigma)

(ii) Reagent Preparation
1. Charcoal dextran solution
   (1) Tris buffer
       Mixed equal amount of Tris-HCl and Tris-base.
   (2)

| | |
|---|---|
| Norit decolorizing neutral charcoal | 2.0 g |
| Tris buffer | 150 mL |
| Stirred | |

(3) Dextran T-70 0.2 g
       Tris buffer 50 ml.
   (4) Slowly dripped the suspended dextran into charcoal solution with stirring.
       Kept in refrigerator overnight.
       Thirty minutes before use, stored on ice with continuous mixing.
2. TEK$_{300}$/Gelatin solution
   50 mg swine gelatin
   5 ml TEDK$_{300}$ solution
   heated, stirred then cooled to 4 C.
   5 ml TEDK$_{300}$ solution
3. Preparation of 1,25(OH)$_2$D$_3$ and test compounds in ethanol
   1,25(OH)$_2$D$_3$: 125, 250, 500, 1000, 2000, 4000 μg/25 μl.
   (stock 10-5 M/25 μL=100,000 pg/25 μL)

| Concentration (ng/mL) | Amount (pg/50 μL) |
|---|---|
| 5.0 | 125 |
| 10.0 | 250 |
| 20.0 | 500 |
| 40.0 | 1000 |
| 80.0 | 2000 |
| 160.0 | 4000 |

Test compounds: 12,500, 25,000, 50,000, 100, 000, 200, 000 and 400,000 μg/25 μL.
   (4*10-5M/25 μL=400,000 μg/25 μL)
4. Dilution of VDR:
   1 μl stock VDR in 2.5 ml TEDK$_{300}$/Gelatin solution (500 μl/tube), (keep on ice)

(iii) Procedure
1. Reaction Setup
   Label tubes according to the following chart, each in triplicate:

| No VDR Control | No VD3 Control | Standard | Test Compounds |
|---|---|---|---|
| Add 25 μL ethanol | Add 25 μL ethanol | Add 25 μL of each standard (in each concentration) | Add 25 μL of each sample (in each concentration) |
| Add 500 μL TEDK300/ gelatin solution | Add 500 μL VDR working solution | Add 500 μL VDR working solution | Add 500 μL VDR working solution |

Mixed all tubes via vortex and incubated at room temperature for 1 hour. Added 10 μL of 3H-1,25(OH)$_2$D$_3$ Working Dilution, mixed by vortex and incubated at room temperature for 1 hour
2. Sample Processing
   Thirty minutes before addition, put Charcoal/Dextran Solution on ice with continuous mixing. Added 100 μL of Charcoal/Dextran Solution to each tube, mixed well and incubated on ice for 30 minutes. Centrifuged (2000 rpm for 10 minutes at 4° C.
3. Counting
   Pipetted 100 μL of the upper, aqueous phase to a 24 well scintillation counting plate and added 600 μL scintillation fluid per well, covered and mixed well. Counted the plate using a scintillation counter for 5 min/sample.

(iv) Calculations:
   The amount of 1,25(OH)$_2$D$_3$ to displace 50 percent [$^3$H]-1,25(OH)$_2$D$_3$ from VDR was calculated as B$_{50}$ for 1,25(OH)$_2$D$_3$. The VDR binding of other compounds was calculated as B$_{50}$ relative to a value of 1 for 1,25(OH)$_2$D$_3$.

| Serial Dilution of 1,25(OH)D$_3$ | | | |
|---|---|---|---|
| Concentration (pg/25 μL) | Final concentration M | $10^{-5}$ M (μl) | Ethanol (μl) |
| 4,000 | $2 \times 10^{-8}$ | 6 | 144 |
| 2,000 | $10^{-8}$ | 70 | 70 |
| 1,000 | $5 \times 10^{-9}$ | 70 | 70 |
| 500 | $2.5 \times 10^{-9}$ | 70 | 70 |
| 250 | $1.25 \times 10^{-9}$ | 70 | 70 |
| 125 | $6.25 \times 10^{-10}$ | 70 | 70 |

| Serial Dilution of Test Compounds | | | |
|---|---|---|---|
| Concentration (pg/50 ul) | Final concentration M | $10^{-3}$ M (μl) | Ethanol (μl) |
| 400,000 | $2 \times 10^{-6}$ | 6 | 144 |
| 200,000 | $10^{-6}$ | 70 | 70 |
| 10,000 | $5 \times 10^{-7}$ | 70 | 70 |
| 5,000 | $2.5 \times 10^{-7}$ | 70 | 70 |
| 25,000 | $1.25 \times 10^{-7}$ | 70 | 70 |
| 12,500 | $6.25 \times 10^{-8}$ | 70 | 70 |

(v) Results:
Compounds of the invention showed and $IC_{50}$ for VDR in this assay in the range of 700→2000 nM.

(vi) References:
1. Ross T K, Prahl J M, DeLuka H. Overproduction of rat 1,25-dihydroxy vitamin $D_3$ receptor in insect cells using the baculovirus expression system. (1991) Proc Natl Acd Sci USA 88:6555-6559
2. Wecksler W R, Norman A W. An hydroxylapatite batch assay for the quantitation of 1alpha, 25-dihydroxy vitamin $D_3$-receptor complexes (1979) Anal Biochem 92:314-323

Example 27

DBP Binding Assay (Human Plasma)

(A) Reagents:
1. Tris buffer:
 22.50 g Tris-HCl
 500 ml $H_2O$
2. 13.25 g Tris-base
 500 ml $H_2O$
 Kept in 4 C
3. Dextran-T70 (Mol 70,000) Pharmacia
4. Charcoal (carbon decolorizing neutral, norit) Fishery
5. DBP (vitamin D binding protein) (human plasma)
6. [$^3$H] 25(OH)$D_3$
7. Gelatin (G-2625 Sigma)

(B) Reagent Preparation:
1. Tris buffer
Mix equal volume of two Tris buffer.
2. Dextran coated charcoal solution
 (1) preparation of charcoal solution

| | |
|---|---|
| Norit decolorizing neutral charcoal | 2.0 g |
| Tris buffer | 150 mL |
| Stirring | |

(2) preparation of dextran solution
 Dextran T-70 0.2 g
 Tris buffer 50 ml
 (3) preparation of dextran coated charcoal solution
 Slowly drip the dextran solution into charcoal solution with stirring.
 Keep in refrigerate overnight.
 Thirty minute before use, keep it on ice with continuous mixing.
 This solution can be kept in 4 C for 2 month.
3. Tris buffer/Gelatin solution
 250 mg swine gelatin
 50 ml Tris buffer
 heating, stirring and cooling on ice.
 Prepared just before use.
4. DBP solution
 Human plasma is diluted to 1:5000 with Tris buffer/gelatin solution
5. Dilution of Standard 25(OH)$D_3$
 Stock 10,000 pg/50 μl
 Diluted to 0, 62.5, 125, 250, 500, 750, 1000, 10,000 μg/50 Fl with ethanol
6. Dilution of Standard 1,25(OH)$_2$$D_3$
 Stock 200,000 μg/50 μl ($10^{-5}$ M/50 μl)
 Diluted to 6,250, 12,500, 25,000, 50,000, 100, 000, 200, 000 μg/50 μl with ethanol
7. Dilution of test compounds
 Stock 200,000 pg/50 μl ($10^{-3}$ M)
 Diluted to 12,500, 25,000, 50,000, 100,000, 200,000 and 400,000 pg/50 μl with ethanol
8. [$^3$H-26,27]-25(OH)$_2$$D_3$ solution
 The stock solution is diluted in Tris buffer, 20,000 CPM/50 μl.

(C) Assay

| Label | 25(OH)$D_3$ | Test compounds (μl) | 3H-25(OH)$D_3$ (μl) | DBP (μl) | Super mix | Incubation (Rm T) | Charcoal dextran (μl) | On ice | Centrifuge | Counting |
|---|---|---|---|---|---|---|---|---|---|---|
| 1-3 (total) | — | — | 50 | — | 600 | — | — | — | — | — |
| 4-8 | — | — | 50 | 500 | 600 | — | — | — | — | — |
| STD 5-35 | 50 | — | 50 | — | | 4 h | 200 | 1 h | 2000 rpm 15 min, 4 C | 200 μl Super + 600 μl Supermix |
| Test 36- | — | 50 | 50 | — | | | | | | |

(D) Calculation:
The amount of 25(OH)$D_3$ to displace 50 percent [$^3$H]-25(OH)$D_3$ is calculated as $B_{50}$ for 25(OH)$D_3$ DBP binding. The DBP binding of other compounds is calculated as $B_{50}$ relative to a value of 1 for 25(OH)$D_3$.

(E) Dilution of 25(OH)$D_3$:

| Amount (mol/50 ul) | From previous steps (μl) | Ethanol (μl) |
|---|---|---|
| $2.5 * 10^{-11}$ ($5 * 10^{-7}$ M) | $5 * 10^{-7}$ M | |
| $2.5 * 10^{-12}$ | 40 | 360 |
| $1.875 * 10^{-12}$ | 90 | 30 |
| $1.25 * 10^{-12}$ | 130 | 130 |
| $6.25 * 10^{-13}$ | 130 | 130 |
| $3.125 * 10^{-13}$ | 130 | 130 |
| $1.5625 * 10^{-13}$ | 130 | 130 |

(F) Dilution of 1,25(OH)D$_3$

| Amount (mol in 50 μl) | From previous steps (μl) | Ethanol (μl) |
|---|---|---|
| 5 * 10$^{-10}$ (10$^{-5}$ M) | | |
| 2.5 * 10$^{-10}$ | 130 | 130 |
| 1.25 * 10$^{-10}$ | 130 | 130 |
| 6.25 * 10$^{-11}$ | 130 | 130 |
| 3.215 * 10$^{-11}$ | 130 | 130 |
| 1.625 * 10$^{-11}$ | 130 | 130 |

(G) Dilution of test compounds:

| Amount (mol in 50 μl) | From previous steps (μl) | Ethanol (μl) |
|---|---|---|
| Stock (10$^{-3}$ M) | | |
| 1.0 * 10$^{-9}$ | 5 | 245 |
| 5.0 * 10$^{-10}$ | 130 | 130 |
| 2.5 * 10$^{-10}$ | 130 | 130 |
| 1.25 * 10$^{-10}$ | 130 | 130 |
| 6.25 * 10$^{-11}$ | 130 | 130 |
| 3.125 * 10$^{-11}$ | 130 | 130 |

(H) Results: Compounds of the invention showed a BPso in this assay of >500 nM.

(I) References: Bouillon R, van Baelen H, Moor P D. Comparative study of the affinity of the serum vitamin D-binding protein. (1980) J Steroid Biochem 13:1029-44. Jones L, Byrnes B, Palma F, Segev D, Mazur E. Displacement potency of vitamin D$_2$ analogue in competitive protein-binding assay for 25-hydroxyvitamin D$_3$, 24,25-dihydroxyvitamin D$_3$ and 1,25-dihydroxyvitamin D$_3$ (1980) J Clin Endocrinol Metab 50:773-775

Example 28

Transcriptional Activation of CYP24 mRNA in PMA-U937 cells

Stage A: Cell Treatment
Reagents & Cells:
  U937 cells (human histiocytic lymphoma; macrophage) grown in 4+ RPMI media 4+RPMI:
    RPMI powder (GIBCO) adjusted to contain 2 g/L sodium bicarbonate
    10 mM HEPES
    1.0 mM sodium pyruvate
    0.1 mM non-essential amino acids
    10% FBS
  PMA (Phorbol 12-myristate 13-acetate), Sigma P1585
  Isopropanol, 99.7% pure HPLC Grade, Caledon
  Calcitriol
  TRIzol reagent, Invitrogen
  70% ethanol
Procedure:
  1) Grow up U937 cells in 4+RPMI media in T75 flasks
  2) Use ~80% confluent cells (usually split 1:2 from confluent flask and fed well with fresh media the previous day)
  3) Perform cell count and spin down cells at 500 g, for 7-10 min.
    (Conditions should be: 24 well plate, with 500,000 cells per well)
  4) Resuspend cells at 500,000 cells/mL
  5) To the cell suspension add 2 μL of PMA stock [10 μg/mL] for every 1 mL of media (final PMA conc.=20 ng/mL) and mix well
  6) Aliquot 1 mL of cells per well and incubate overnight at 37° C.+5% CO$_2$.
  7) Obtain a 1 mM stock solution for each of the compounds to be tested
  8) Make 1, 10 & 100 μM stock solutions for each compound to be tested:
    100 M—add 2 μl of 1 mM stock into 18 μl of isopropanol
    10 μM—add 2 μl of 100 μM into 18 μl of isopropanol
    1 μM—add 2 μl of 10 μM into 18 μl of isopropanol
  9) Aspirate the old media using the vacuum pump.
  10) Add 1 ml of fresh 4+RPMI media to each well.
  11) Add the compound to each of the wells as follows (each in triplicate):
    100 nM—add 1 μl of 100 μM compound into 1 ml of the media
    10 nM—add 1 μl of 10 μM compound into 1 ml of the media
    1 nM—add 1 μl of 1M compound into 1 ml of the media
  12) Mix the plate as follows: 10 sec Θ, then 10 sec Θ, then 15 sec Θ
  13) Incubate the cells at 37 C+5% CO$_2$ for 6 hours.
  14) Aspirate the old media, after 6 hours, and add 1 ml of TRIzol reagent to each well.
  15) Dissolve the cells in the well by pipetting around the TRIzol.
  16) Transfer the cells dissolved in TRIzol to a 1.7 ml tube.
  17) Store the cells dissolved in TRIzol at −80 C until use.
Stage B: RNA Isolation and cDNA Synthesis
Reagents:
  RNA samples dissolved in 1 ml TRIzol®
  Chloroform
  Isopropanol
  −20 C 75% Ethanol
  Depc-dH$_2$O
  ThermoScript™ RT-PCR System, Invitrogen, 11146-024 (25 Rx), -016 (100 Rx)
  Diethylpyrocarbonate-dH$_2$O
Procedure:
  1) Thaw the 1 ml TRIzol®-RNA samples (if necessary)
  2) Add 200 μl chloroform
  3) Vortex for 15 sec
  4) Let stand for 3 min at R$_T$
  5) Spin at 15K rpm for 10 min
  6) Transfer aqueous (top) layer to a new 1.7 ml tube (~600 μl)
  7) Add 500 μl isopropanol
  8) Invert tubes 5-6 times to mix
  9) Let stand for 10 min at RT
  10) Spin at 15K rpm for 10 min
  11) Aspirate the isopropanol
  12) Add 1 ml of −20 C 75% ethanol
  13) Spin at 15K rpm for 20 min
  14) Aspirate the 75% ethanol
  15) Air dry pellet and add 20 μl of Depc-dH$_2$O
  16) Pipette up and down to dissolve the RNA pellet
  17) Store at −80 C until use
  18) Perform cDNA synthesis according to manufacturer's instructions for the ThermoScript™ RT-PCR System, Invitrogen.
Stage C: TaqMan Real-Time PCR
Reagents:
  2× Universal TaqMan® master mix, ABI, P/N 4304437
  Assay-on-Demand Cyp24 TaqMan® (FAM) probe, ABI, Hs00167999?ml Assay-on-Demand Gapdh TaqMan® (JOE) probe, ABI, 402869 dH$_2$O Procedure:

1) Prepare the real time master mix (1 reaction):

| | |
|---|---|
| 2 × Universal TaqMan ® master mix | 10 µl |
| 20 × TaqMan ® Cyp24 probe | 1 µl |
| Gapdh forward primer | 0.4 µl |
| Gapdh reverse primer | 0.4 µl |
| Gapdh TaqMan ® probe | 0.4 µl |
| dH$_2$O | 2.8 µl |
| | 15 µl |

Note:
If you would like to do Cyp24 and Gapdh separately, just alter the master mix by removing the Cyp24 or Gapdh and replacing the volume with dH$_2$0.

2) Aliquot 15 µl real time master mix to each of the wells
3) Aliquot 5 µl cDNA to each of the well, pipetting up and down 5-6 times to mix.
4) Seal the plate using the plate sealer.
5) Run the real-time PCR reactions as per the instructions for the ABI Prism 7000 SDS Software®.

Results: Compounds of the invention, at a concentration of 100 nM, showed a percent induction of 100 nM calcitriol in the range of 0.1 to 40%.

Example 29

Human Epidermal Keratinocyte Proliferation (HEK) Assay (i) Materials:
Normal HEK cells (Cambrex, Walkersville, Md.)
Bullet kit KGM-Ca media (Cambrex, Walkersville, Md.)
Reagent pack (Cambrex, Walkersville, Md.)
Calcium chloride (Cambrex, Walkersville, Md.)
25 cm$^2$ tissue culture flasks
96-well tissue culture plates
[$^3$H]-thymidine (Perkin Elmer, Boston, Mass.)
calcitriol (1 mM) reconstituted in isopropanol (Sigma, St. Louis, Mo.)
96-well filter plates
scintillation fluid
scintillation counter
Tomtec cell harvester (Tomtec, Hamden, Conn.)

(ii) Reagent Preparation
1. HEK cell media
Supplement KGM media with additional reagents provided in the bullet kit as per supplier's instructions.
Add calcium chloride to final concentration of 0.3 mM.
2. Calcitriol dilutions Stock: Calcitriol (1 mM)

| Concentration (final) | from previous step (µl) | KGM media (µl) | Isopropanol (µl) | Concentration (actual) |
|---|---|---|---|---|
| $10^{-6}$ M | 8 of stock | 992 | 12 | $8 \times 10^{-6}$ M |
| $10^{-7}$ M | 100 | 882 | 18 | $8 \times 10^{-7}$ M |
| $10^{-8}$ M | 100 | 882 | 18 | $8 \times 10^{-8}$ M |
| $10^{-9}$ M | 100 | 882 | 18 | $8 \times 10^{-9}$ M |
| $10^{-10}$ M | 100 | 882 | 18 | $8 \times 10^{-10}$ M |
| $10^{-11}$ M | 100 | 882 | 18 | $8 \times 10^{-11}$ M |

3. Substrate dilutions

Stock: substrate (0.1 mM)

| Concentration (final) | from previous step (µl) | KGM media (µl) | Isopropanol (µl) | Concentration (actual) |
|---|---|---|---|---|
| $10^{-7}$ M | 8 of stock | 992 | 12 | $8 \times 10^{-6}$ M |
| $5 \times 10^{-8}$ M | 500 | 490 | 10 | $8 \times 10^{-7}$ M |
| $10^{-8}$ M | 200 | 784 | 16 | $8 \times 10^{-8}$ M |
| $10^{-9}$ M | 100 | 882 | 18 | $8 \times 10^{-9}$ M |
| $10^{-10}$ M | 100 | 882 | 18 | $8 \times 10^{-11}$ M |

(iii) Procedure:
2. Cell culture
Thaw one vial of HEK cells containing at least 500 K, and divide into 5 25 cm$^2$ flasks with 5 ml HEK cell media. 24 h later, remove media and replenish with 5 ml fresh media. Change media again 48 h later.

3. Preparation of cell suspension
On the day of the assay, wash the monolayer of HEK cells once with 1×PBS buffer (provided in reagent pack) and then trypsinize for 5 min at 37° C. Add trypsin neutralizing solution (provided in reagent pack). Collect cells into tube, centrifuge cells (500×g, 5 min) and resuspend in HEK cell media. Count cells and adjust density to 150,000 cells/ml. Dilute cells further 1:30 with HEK cell media.

2. Cell plating
Add 150 µl of cell suspension to appropriately labelled wells of a 96-well plate. Incubate plate for 48 h at 37° C. in a humidified atmosphere containing 5% CO$_2$ for adherence of cells to wells.

3. Compound addition
Add 25 µl of calcitriol ($10^{-6}$ to $10^{-11}$ M, final) and add 25 µl of substrate ($10^{-7}$ to $10^{-10}$ M, final) and incubate for 32 hours at 37° C. in a humidified atmosphere containing 5% CO$_2$.

4. Cell harvesting and counting
Add 0.2 µCi/well of [$^3$H]-thymidine in 20 µl of HEK cell media to each well. Incubate plates for 18 h at 37° C. in a humidified atmosphere containing 5% CO$_2$. Aspirate media and wash with 1×PBS. Trypsinize cells for 30 min at 37° C. in a humidified atmosphere containing 5% CO$_2$. Harvest cells onto filter plates using Tomtec cell harvester as per manufacturer's instructions. Add 25 µl scintillation fluid per well. Measure radioactivity using a scintillation counter. All values were normalized for background.

Figure 2:
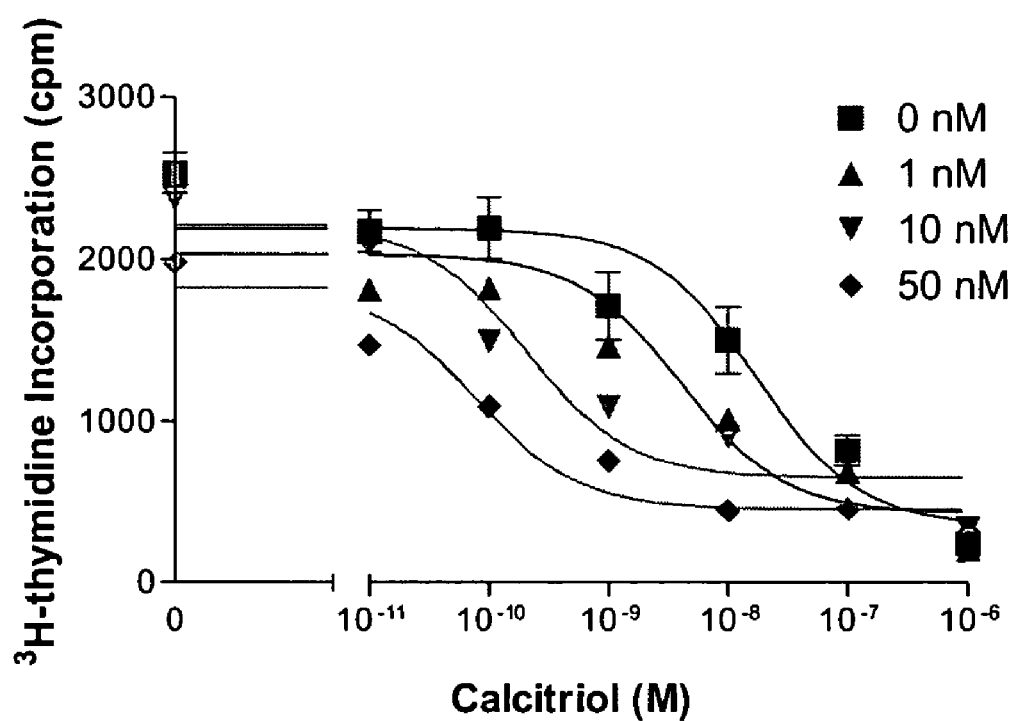
FIG. 2 is a graph showing that compound IIa and calcitriol act to inhibit normal human epidermal keratinocytes (NHEK). NHEK were treated with specified concentrations of calcitriol and compound IIa for three days. Cells were then incubated with [$^3$H]-thymidine for 18 h at 37° C. in a humidified atmosphere containing 5% $CO_2$. Plates were harvested and radioactivity measured. Dose response curves in the absence of IIa, 1 nM IIa, 10 nM IIa and 50 nM IIa are shown.
Figure 3:
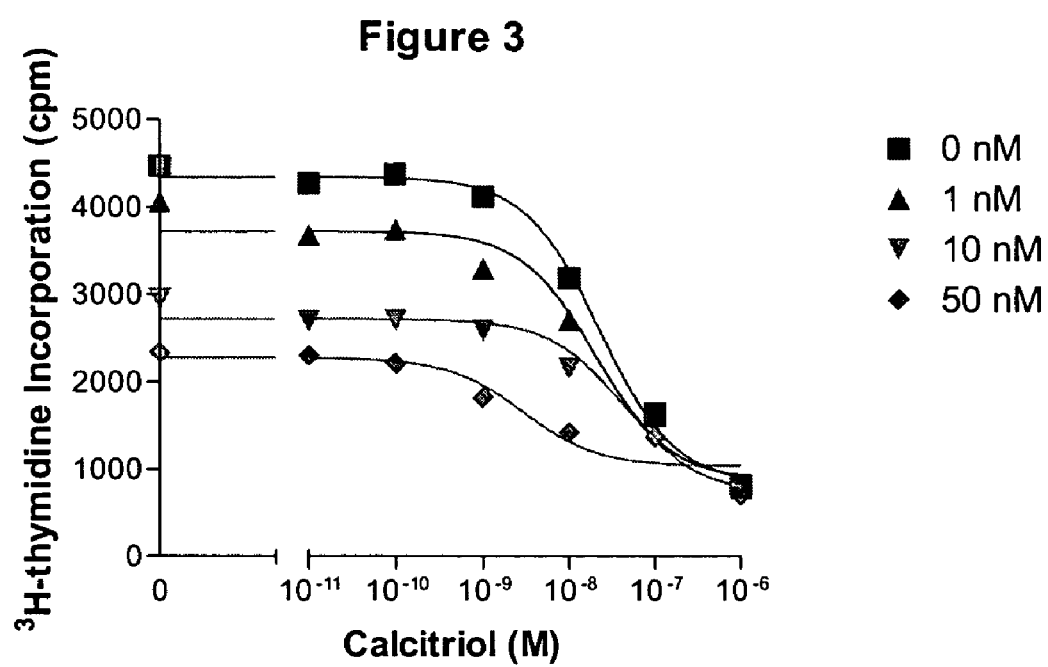
FIG. 3 is a graph showing that compound IVa and calcitriol act to inhibit normal human epidermal keratinocytes (NHEK). NHEK were treated with specified concentrations of calcitriol and compound IVa for three days. Cells were then incubated with [$^3$H]-thymidine for 18 h at 37° C. in a humidified atmosphere containing 5% $CO_2$. Plates were harvested and radioactivity measured. Dose response curves in the absence of IIa, 1 nM IIa, 10 nM IVa and 50 nM IIa are shown.
Figure 4:
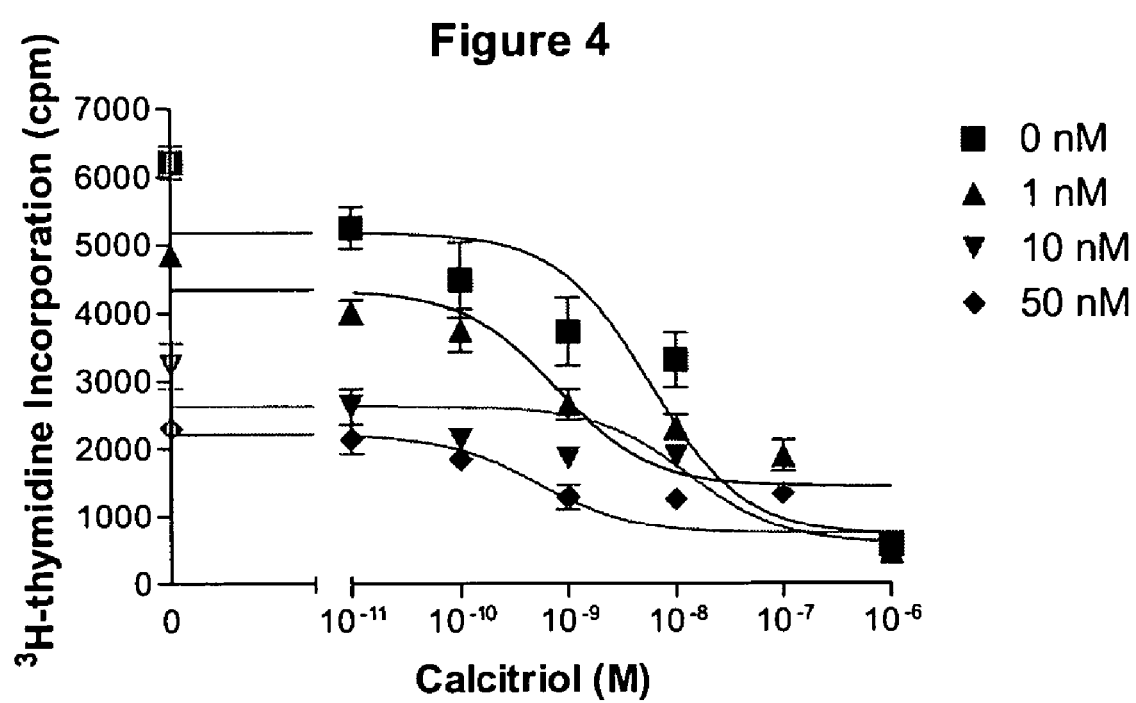
FIG. 4 is a graph showing that compound Ib(v) and calcitriol act to inhibit normal human epidermal keratinocytes (NHEK). NHEK were treated with specified concentrations of calcitriol and compound Ib(v) for three days. Cells were then incubated with [$^3$H]-thymidine for 18 h at 37° C. in a humidified atmosphere containing 5% $CO_2$. Plates were harvested and radioactivity measured. Dose response curves in the absence of Ib(v), 1 nM Ib(v), 10 nM Ib(v) and 50 nM Ib(v) are shown.

Results; See FIGS. 1-4

Example 30

[$^3$H]-thymidine Proliferation Assay with MCF-7 Cells (i) Materials:
MCF-7 cells
MEM supplemented with sodium pyruvate, non-essential amino acids, bovine insulin, gentamycin and 10% Fetal bovine serum (growth media)
RPMI1640 supplemented with tri-iodothyronine, hydrocortisone, transferin, bovine insulin and 5% Fetal bovine serum (proliferation media)
1α,25(OH)$_2$D$_3$ 1 mM reconstituted in isopropanol substrates (1 mM) reconstituted in isopropanol
Trypsin:EDTA solution
1×PBS
75 cm² tissue culture flasks
96 well tissue culture plates
Liquid scintillation fluid
96 well filter plate (Millipore)

(ii) Procedure:
1. Preparation of cell suspension
   When MCF-7 cells are 70-80% confluent, aspirate growth media. Wash the cells with 1×PBS. Trypsinize with trypsin-EDTA from the plate, collect cells from the tissue culture flask, centrifuged (500×g, 5 min) and resuspended in growth media.
2. Cell plating.
   Count the cells and adjust the cell density to 25,000/ml. Add 200 μl per well in a 96 well plate. Incubate plate for 24 h at 37° C. in a humidified atmosphere plus 5% $CO_2$. Aspirate used media and replace with 150 ml per well with proliferation media.
3. Substrate addition.
   Add 25 μl of 1α,25(OH)$_2$D$_3$ (final concentration $10^{-6}$ M, $10^{-7}$ M, $10^{-8}$ M, $10^{-9}$ M, $10^{-10}$ M, $10^{-11}$ M) into each designated well. Add 25 μl of Substrate (final concentration $10^{-7}$ M, $5\times10^{-8}$ M, $10^{-8}$ M or $10^{-9}$ M) into each designated well. Incubate plates for 3 days at 37° C. in a humidified atmosphere plus 5% $CO_2$.
4. ³H-Thymidine incorporation.
   Add ³H-thymidine at 0.02 μCi per well and incubate at 37° C. in a humidified atmosphere plus 5% $CO_2$ for 6 h.
5. Plate Harvesting.
   Aspirate all media and wash cells with 1×PBS. Trypsinize cells for 30 min at 37° C. in a humidified atmosphere plus 5% $CO_2$. Harvest cells onto a 96 well filter plate (Millipore) using a Tomtec Cell Harvestor, according to manufacturers instructions.
6. Scintillation Counting.
   Add 25 μt of scintillation fluid per well. Count the plate using a scintillation counter.

Figure 5:
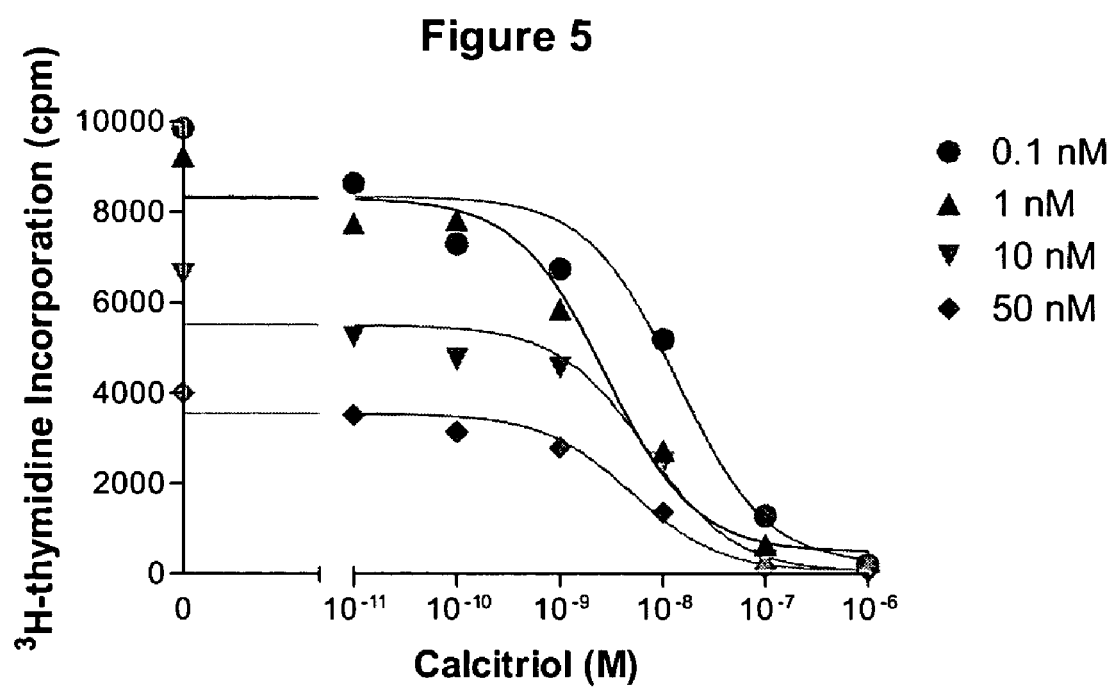
FIG. 5 is a graph showing that compound Va and calcitriol act to inhibit MCF-7 cells. MCF-7 cells were treated with specified concentrations of calcitriol and compound Va for three days. Cells were then incubated with [$^3$H]-thymidine for 6 h at 37° C. in a humidified atmosphere containing 5% $CO_2$. Plates were harvested and radioactivity measured. Dose response curves in the absence of Va, 1 nM Va, 10 nM Va and 50 nM Va are shown.
Figure 6:
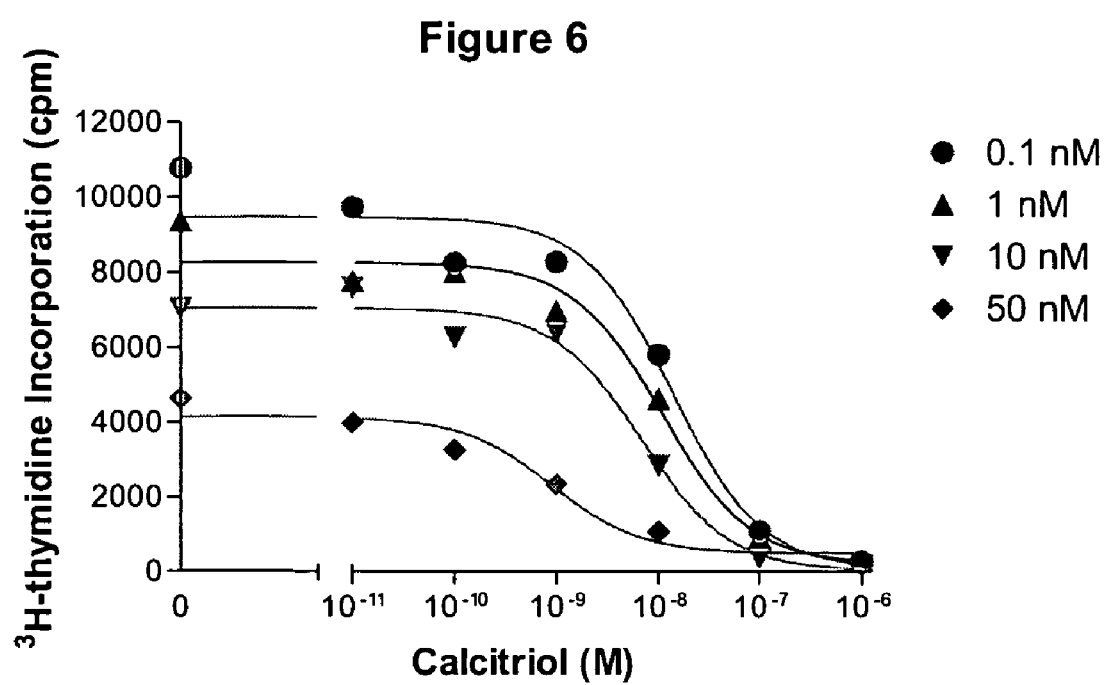
FIG. 6 is a graph showing that compound Ia and calcitriol act to inhibit MCF-7 cells. MCF-7 cells were treated with specified concentrations of calcitriol and compound IIa for three days. Cells were then incubated with [$^3$H]-thymidine for 6 h at 37° C. in a humidified atmosphere containing 5% $CO_2$. Plates were harvested and radioactivity measured. Dose response curves in the absence of Ia, 1 nM IIa, 10 nM IIa and 50 nM IIa are shown.
Figure 7:
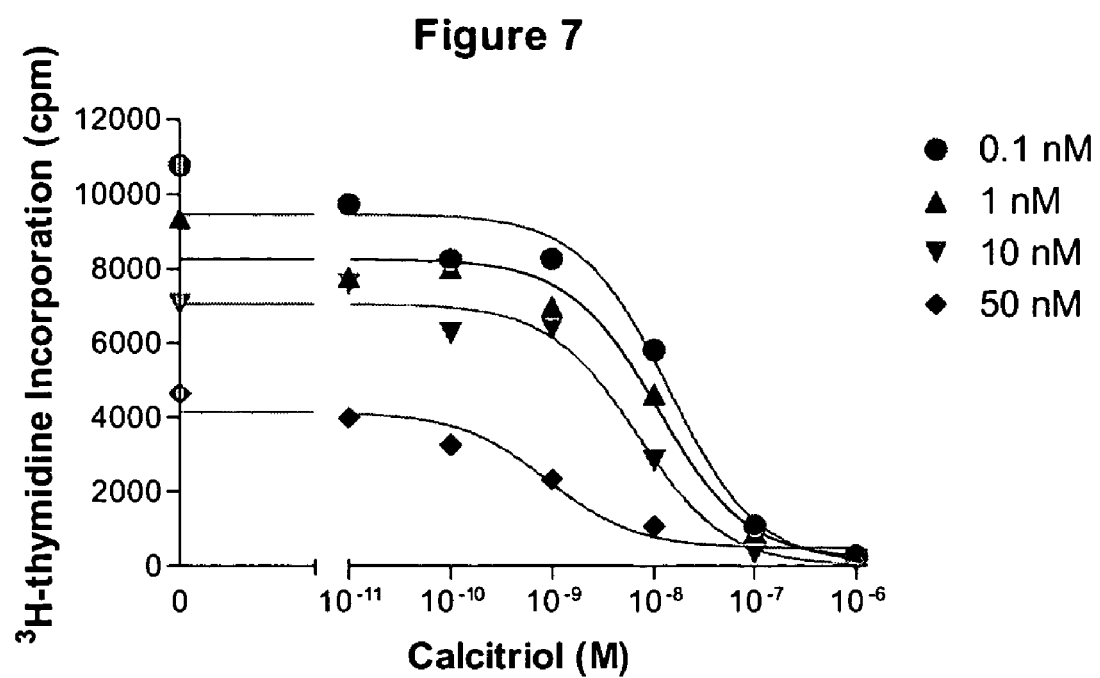
FIG. 7 is a graph showing that compound IVa and calcitriol act to inhibit MCF-7 cells. MCF-7 cells were treated with specified concentrations of calcitriol and compound IVa for three days. Cells were then incubated with [$^3$H]-thymidine for 6 h at 37° C. in a humidified atmosphere containing 5% $CO_2$. Plates were harvested and radioactivity measured. Dose response curves in the absence of IVa, 1 nM IVa, 10 nM IVa and 50 nM IVa are shown.
Figure 8:
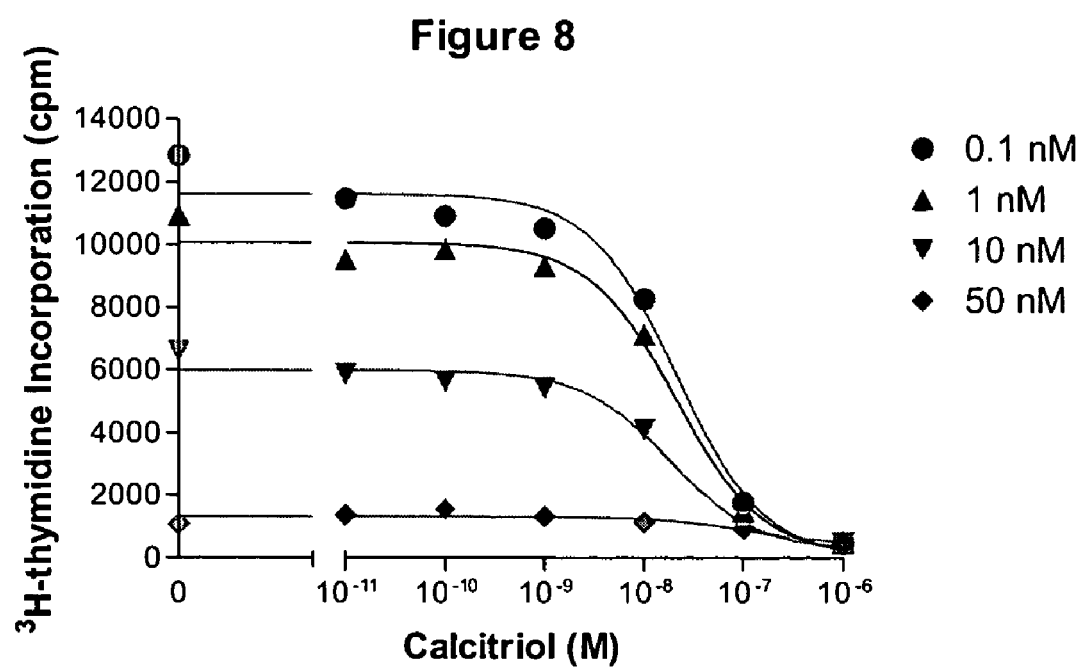
FIG. 8 is a graph showing that compound Ib(v) and calcitriol act to inhibit MCF-7 cells. MCF-7 cells were treated with specified concentrations of calcitriol and compound Ib(v) for three days. Cells were then incubated with [$^3$H]-thymidine for 6 h at 37° C. in a humidified atmosphere containing 5% $CO_2$. Plates were harvested and radioactivity measured. Dose response curves in the absence of Ib(v), 1 nM Ib(v), 10 nM Ib(v) and 50 nM Ib(v) are shown.
Figure 9:
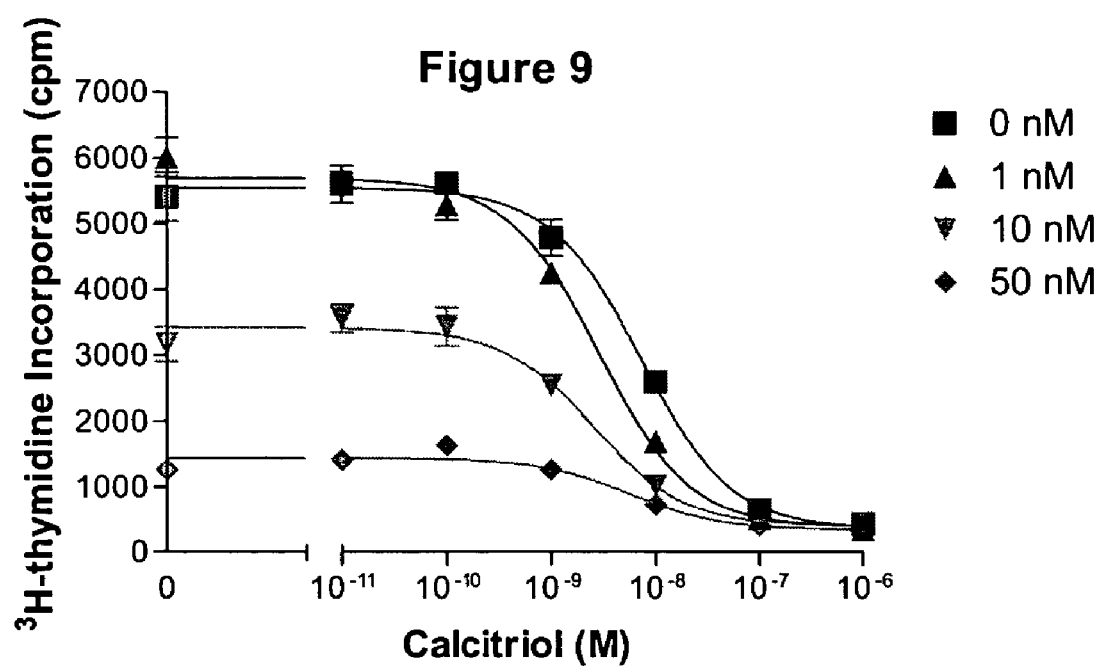
FIG. 9 is a graph showing that compound Ia(xi) and calcitriol act to inhibit MCF-7 cells. MCF-7 cells were treated with specified concentrations of calcitriol and compound Ia(xi) for three days. Cells were then incubated with [$^3$H]-thymidine for 6 h at 37° C. in a humidified atmosphere containing 5% $CO_2$. Plates were harvested and radioactivity measured. Dose response curves in the absence of Ia(xi), 1 nM Ia(xi), 10 nM Ia(xi) and 50 nM Ia(xi) are shown.

Results: See FIGS. 5-9.

Example 31

[³H]-thymidine Proliferation Assay with SCC-25 Cells (i) Materials:
SCC-25 cells
DMEM-F12 supplemented with hydrocortisone and 5% Fetal bovine serum
1α,25(OH)$_2$D$_3$ 1 mM reconstituted in isopropanol
Substrates (1 mM) reconstituted in isopropanol
Trypsin:EDTA solution
1×PBS
75 cm tissue culture flasks
96 well tissue culture plates
Liquid scintillation fluid
96 well filter plate (Millipore)

(ii) Procedure:
1. Preparation of cell suspension
   When SCC-25 cells are 70-80% confluent, aspirate media. Wash the cells with 1×PBS. Trypsinize with trypsin-EDTA from the plate, collect cells from the tissue culture flask, centrifuged (500×g, 5 min) and resuspended in media.
2. Cell plating.
   Count the cells and adjust the cell density to 10,000/ml. Add 200 μl per well in a 96 well plate. Incubate plate for 24 h at 37° C. in a humidified atmosphere plus 5% $CO_2$. Aspirate used media and replace with 150 μl per well with media.
3. Compound addition.
   Add 25 μl of 1α,25(OH)$_2$D$_3$ (final concentration $10^{-6}$ M, $10^{-7}$ M, $10^{-8}$ M, $10^{-9}$ M, $10^{-10}$ M, $10^{-11}$ M) into each designated well. Add 25 μL of Substrate (final concentration $10^{-7}$ M, $5\times10^{-8}$ M, $10^{-8}$ M or $10^{-9}$ M) into each designated well. Incubate plates for 3 days at 37° C. in a humidified atmosphere plus 5% $CO_2$.
4. ³H-Thymidine incorporation.
   Add ³H-thymidine at 0.02 μCi per well and incubate at 37° C. in a humidified atmosphere plus 5% $CO_2$ for 6 h.
5. Plate Harvesting.
   Aspirate all media and wash cells with 1×PBS. Trypsinize cells for 30 min at 37° C. in a humidified atmosphere plus 5% $CO_2$. Harvest cells onto a 96 well filter plate (Millipore) using a Tomtec Cell Harvestor, according to manufacturers instructions.
6. Scintillation Counting.
   Add 25 μl of scintillation fluid per well. Count the plate using a scintillation counter.

Figure 10:
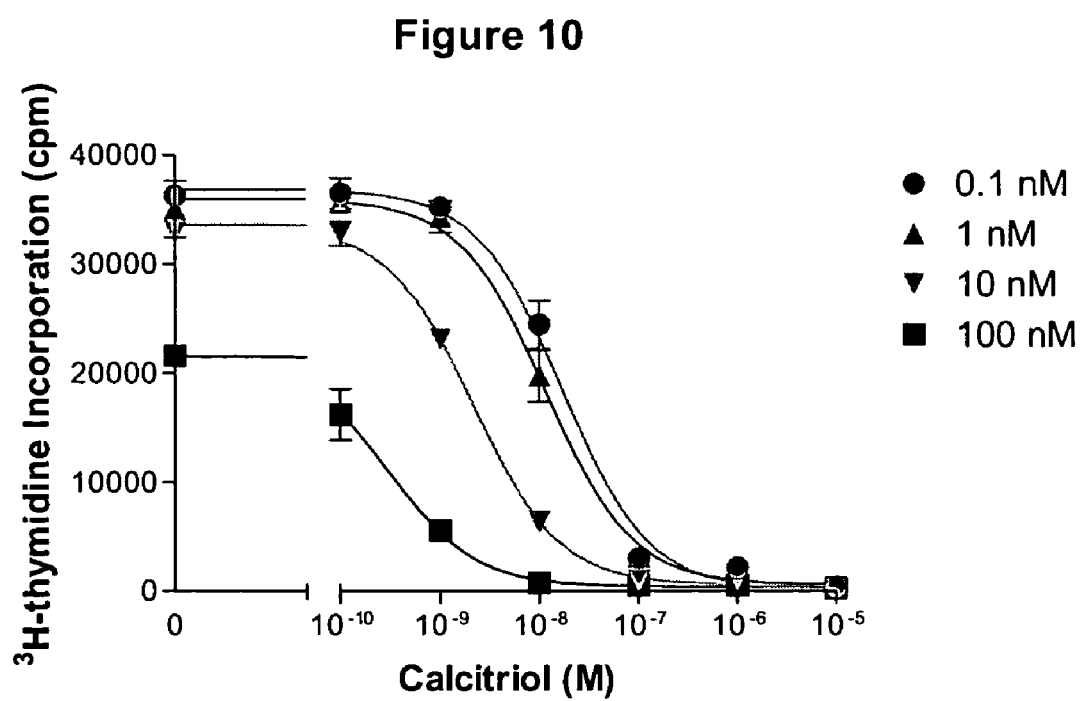
FIG. 10 is a graph showing that compound Va and calcitriol act to inhibit SCC-25 cells. SCC-25 cells were treated with specified concentrations of calcitriol and compound Va for three days. Cells were then incubated with [$^3$H]-thymidine for 6 h at 37° C. in a humidified atmosphere containing 5% $CO_2$. Plates were harvested and radioactivity measured. Dose response curves in the absence of Va, 1 nM Va, 10 nM Va and 50 nM Va are shown.
Figure 11:
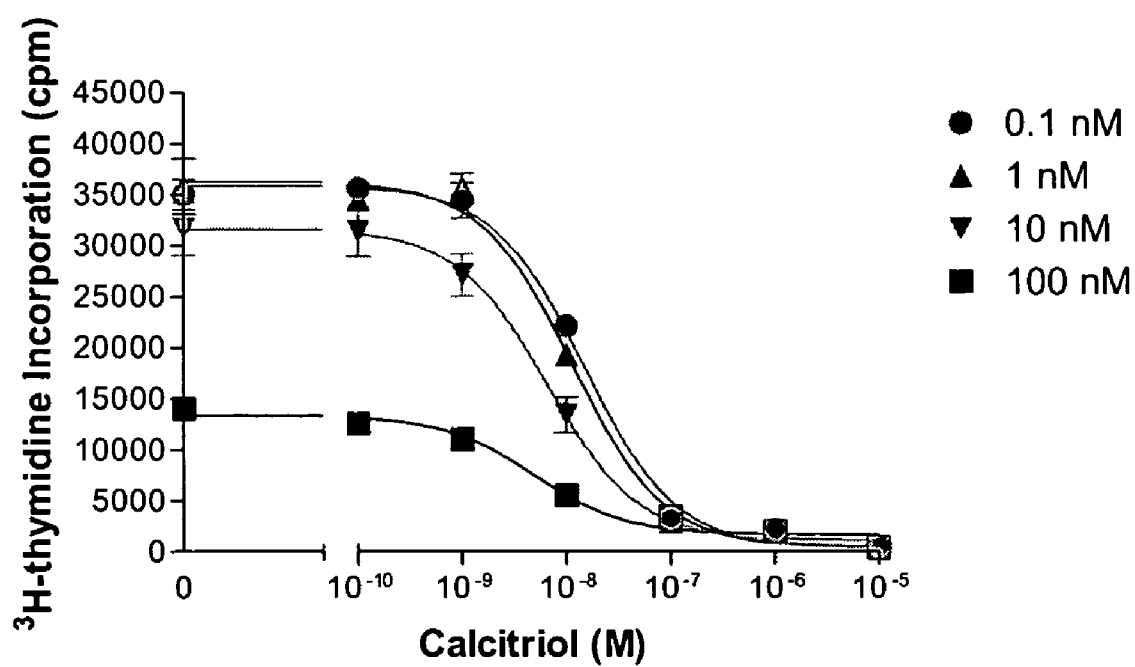
FIG. 11 is a graph showing that compound IIa and calcitriol act to inhibit SCC-25 cells. SCC-25 cells were treated with specified concentrations of calcitriol and compound Ia for three days. Cells were then incubated with [3H]-thymidine for 6 h at 37° C. in a humidified atmosphere containing 5% $CO_2$. Plates were harvested and radioactivity measured. Dose response curves in the absence of IIa, 1 nM IIa, 10 nM IIa and 50 nM IIa are shown.
Figure 12:
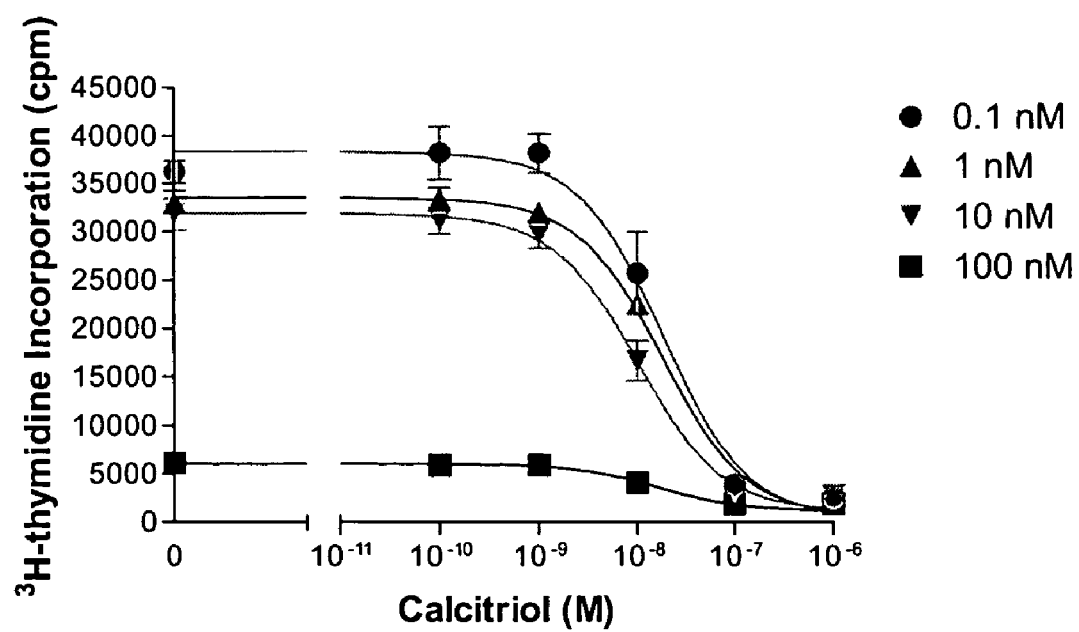
FIG. 12 is a graph showing that compound IVa and calcitriol act to inhibit SCC-25 cells. SCC-25 cells were treated with specified concentrations of calcitriol and compound IVa for three days. Cells were then incubated with [$^3$H]-thymidine for 6 h at 37° C. in a humidified atmosphere containing 5% $CO_2$. Plates were harvested and radioactivity measured. Dose response curves in the absence of IVa, 1 nM IVa, 10 nM IVa and 50 nM IVa are shown.
Figure 13:
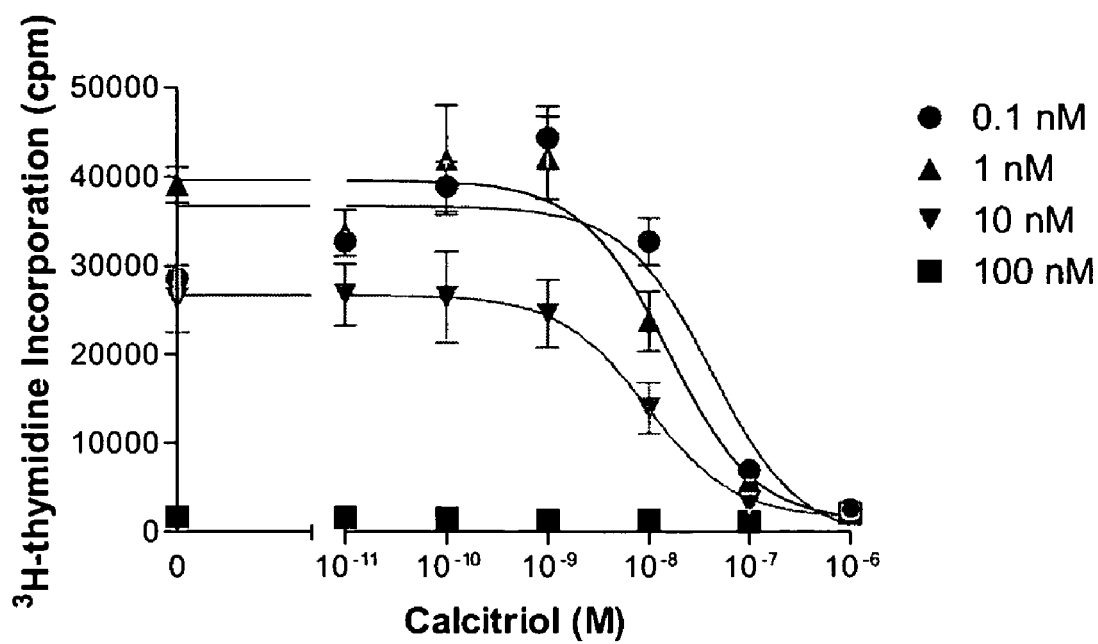
FIG. 13 is a graph showing that compound Ib(v) and calcitriol act to inhibit SCC-25 cells. SCC-25 cells were treated with specified concentrations of calcitriol and compound Ib(v) for three days. Cells were then incubated with [$^3$H]-thymidine for 6 h at 37° C. in a humidified atmosphere containing 5% $CO_2$. Plates were harvested and radioactivity measured. Dose response curves in the absence of Ib(v), 1 nM Ib(v), 10 nM Ib(v) and 50 nM Ib(v) are shown.

Results: See FIGS. 10-13.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

We claim:
1. A compound of Formula Ia or Ib, or a pharmaceutically acceptable salt or prodrug thereof:

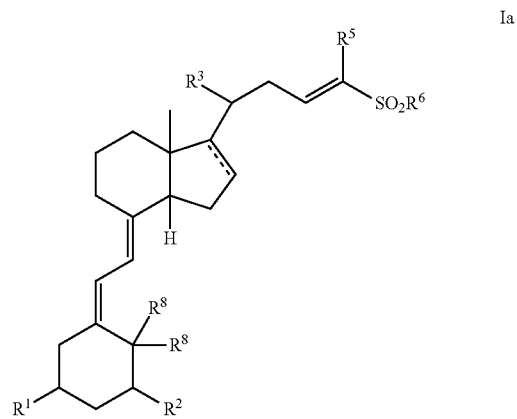

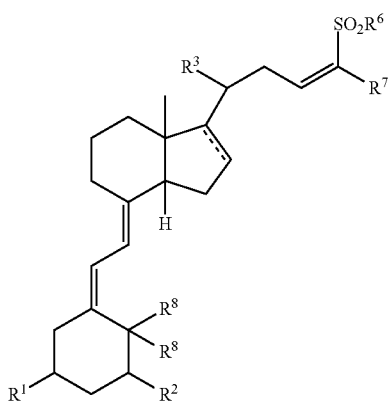

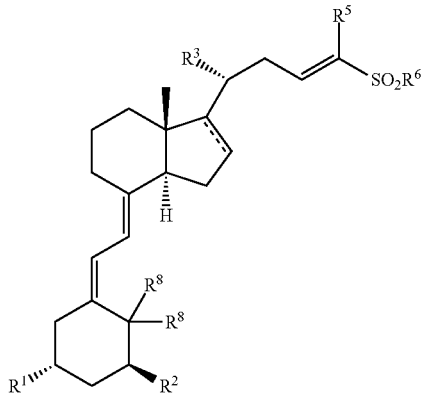

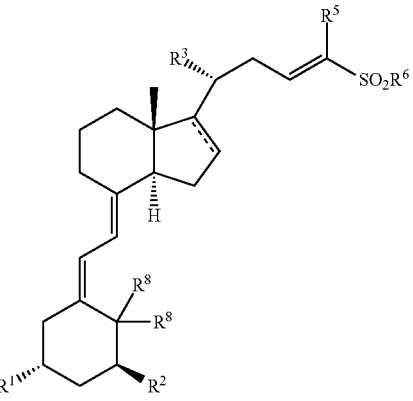

wherein said prodrug is an ester;

$R^1$ and $R^2$ are independently selected from the group consisting of OH, $OC_{1-4}$alkyl, and halo;

$R^3$ is $C_{1-4}$alkyl;

$R^5$ is selected from the group consisting of $C_{1-4}$alkyl, $OC_{1-4}$alkyl, $SC_{1-4}$alkyl, $SO_2C_{1-4}$alkyl, $P(O)(OC_{1-4}$alkyl$)_2$ and SCN;

$R^6$ is selected from the group consisting of $C_{1-4}$alkyl, unsubstituted Ph and Ph substituted with 1-2 groups independently selected from $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl$)(C_{1-4}$alkyl$)$ and CN;

$R^7$ is selected from the group consisting of $C_{1-4}$alkyl, $OC_{1-4}$ alkyl, $SC_{1-4}$alkyl, $SO_2C_{1-4}$alkyl, $P(O)(OC_{1-4}$alkyl$)_2$ and SCN;

$R^8$ are either both H or together form $=CH_2$; and

==== represents a single or a double bond, with the proviso that ==== represents a single bond when $R^5$ is $C_{1-4}$alkyl or when $R^7$ is $C_{1-4}$alkyl.

2. The compound according to claim 1, wherein $R^1$ and $R^2$ are independently selected from the group consisting of OH, $OCH_3$, and fluoro.

3. The compound according to claim 2, wherein $R^1$ and $R^2$ are both OH.

4. The compound according to claim 1, wherein $R^3$ is $CH_3$.

5. The compound according to claim 1, wherein $R^5$ is selected from the group consisting of $CH_3$, $OCH_3$, $SCH_3$ and SCN.

6. The compound according to claim 1, wherein $R^6$ is $C_{1-4}$alkyl or an unsubstituted Ph.

7. The compound according to claim 6, wherein $R^6$ is t-butyl or unsubstituted Ph.

8. The compound according to claim 1, wherein $R^7$ is selected from the group consisting of $CH_3$, $OCH_3$, $SCH_3$, $SO_2CH_3$ and SCN.

9. The compound according to claim 1, wherein $R^8$ together form $=CH_2$.

10. The compound according to claim 1, selected from a compound having relative stereochemistry as follows:

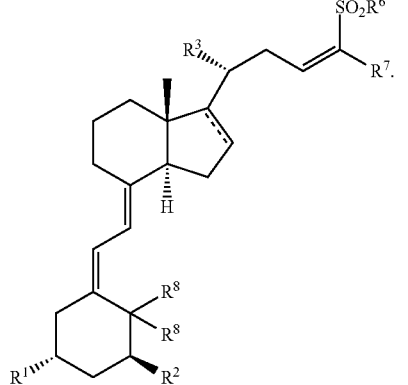

11. The compound of claim 1, wherein the ester is selected from the group consisting of any of a phenyl ester, an aliphatic ($C_8$-$C_{24}$) ester, an acyloxymethyl ester, a carbamate and an amino acid ester.

12. A pharmaceutical composition comprising a compound according to claim 1 and a pharmaceutically acceptable carrier.

13. A method for treating a disease selected from the group consisting of psoriasis, hyperparathyroidism, secondary hyperparathyroidism, osteoporosis, breast cancer, lung cancer, prostate cancer, colon cancer, colorectal cancer, kidney cancer, head and neck cancer, pancreatic cancer, Kaposi's sarcoma, leukemia, skin cancer, pseudohypoparathyroidism, diabetes, medullary carcinoma, wound healing, sarcoidosis, tuberculosis, chronic renal disease, hypophosphatemic vitamin D resistant rickets (VDRR), vitamin D dependent rickets, fibrogenisis imperfecta ossium, osteitis fibrosa cyctica, osteomalacia, osteopenia, osteosclerosis, renal osteodystrophy and rickets, comprising administering an effective amount of a compound of claim 1 to a cell or animal in need thereof.

14. The method according to claim 13, wherein the disease is selected from one or more of breast cancer, lung cancer, prostate cancer, colon cancer, colorectal cancer, kidney cancer, head and neck cancer, pancreatic cancer, Kaposi's sarcoma, leukemia and skin cancer.

15. A method for increasing the efficacy of a vitamin D receptor agonist comprising co-administering an effective amount of a compound of claim 1 and an effective amount of a vitamin D receptor agonist to an animal or cell in need thereof, wherein the vitamin D receptor agonist is 1α,25-dihydroxyvitamin $D_3$ (calcitriol).

16. The method according to claim 15, used to treat a disease selected from the group consisting of breast cancer, lung cancer, prostate cancer, colon cancer, colorectal cancer, kidney cancer, head and neck cancer, pancreatic cancer, Kaposi's sarcoma, leukemia, psoriasis, hyperparathyroidism, secondary hyperparathyroidism and osteoporosis.

17. A method of treating a disease selected from the group consisting of psoriasis, hyperparathyroidism, secondary hyperparathyroidism, osteoporosis, breast cancer, lung cancer, prostate cancer, colon cancer, colorectal cancer, kidney cancer, head and neck cancer, pancreatic cancer, Kaposi's sarcoma, leukemia, skin cancer, pseudohypoparathyroidism, diabetes, medullary carcinoma, wound healing, sarcoidosis, tuberculosis, chronic renal disease, hypophosphatemic vitamin D resistant rickets (VDRR), vitamin D dependent rickets, fibrogenisis imperfecta ossium, osteitis fibrosa cyctica, osteomalacia, osteopenia, osteosclerosis, renal osteodystrophy and rickets, comprising administering an effective amount of a compound according to claim 1 in combination with one or more therapies or therapeutics to treat at least one of said diseases to an animal or cell in need thereof.

18. The method according to claim 17, wherein the disease is selected from the group consisting of breast cancer, lung cancer, prostate cancer, colon cancer, colorectal cancer, kidney cancer, head and neck cancer, pancreatic cancer, Kaposi's sarcoma, leukemia and skin cancer.

19. The method according to claim 18, wherein the one or more therapies or therapeutics to treat cancer are selected from the group consisting of surgery, radiation, chemotherapy and biotherapy.

20. The method according to claim 17, wherein the disease is psoriasis.

21. The method according to claim 20, wherein the one or more therapies or therapeutics to treat psoriasis are selected from the group consisting of ultraviolet B radiation, chemotherapy and biotherapy.

* * * * *

UNITED STATES PATENT AND TRADEMARK OFFICE
CERTIFICATE OF CORRECTION

PATENT NO. : 8,106,035 B2
APPLICATION NO. : 10/738248
DATED : January 31, 2012
INVENTOR(S) : Posner et al.

Page 1 of 1

It is certified that error appears in the above-identified patent and that said Letters Patent is hereby corrected as shown below:

In the Claims

In Column 97, Line 32, in Claim 1, delete "$OC_{1-44}$ alkyl," and insert -- $OC_{1-4}$alkyl, --, therefor.

Signed and Sealed this
Fifth Day of August, 2014

Michelle K. Lee
*Deputy Director of the United States Patent and Trademark Office*